(12) United States Patent
Monsonego

(10) Patent No.: US 10,117,895 B2
(45) Date of Patent: Nov. 6, 2018

(54) T-CELL THERAPY TO NEURODEGENERATIVE DISEASES

(75) Inventor: Alon Monsonego, Moshav Nir-Banim (IL)

(73) Assignee: Ben-Gurion University of the Negev Research and Development Authority, Beer-Sheva (IL)

( * ) Notice: Subject to any disclaimer, the term of this patent is extended or adjusted under 35 U.S.C. 154(b) by 221 days.

(21) Appl. No.: 13/884,980

(22) PCT Filed: Nov. 17, 2011

(86) PCT No.: PCT/IB2011/055144
§ 371 (c)(1),
(2), (4) Date: May 13, 2013

(87) PCT Pub. No.: WO2012/066495
PCT Pub. Date: May 24, 2012

(65) Prior Publication Data
US 2013/0280224 A1    Oct. 24, 2013

Related U.S. Application Data

(60) Provisional application No. 61/414,453, filed on Nov. 17, 2010.

(51) Int. Cl.
*A61K 39/00* (2006.01)
*C12N 5/0783* (2010.01)
*A61K 35/17* (2015.01)
*A61K 35/12* (2015.01)

(52) U.S. Cl.
CPC .......... *A61K 35/17* (2013.01); *A61K 39/0007* (2013.01); *C12N 5/0636* (2013.01); *A61K 2035/124* (2013.01); *A61K 2039/5156* (2013.01); *A61K 2039/5158* (2013.01); *A61K 2039/572* (2013.01); *C12N 2501/24* (2013.01); *C12N 2501/51* (2013.01); *C12N 2501/515* (2013.01); *C12N 2510/00* (2013.01)

(58) Field of Classification Search
CPC .......... A61K 2035/124; A61K 39/0007; A61K 2039/5156; A61K 2039/5158; C12N 2501/24; C12N 2501/51; C12N 2501/515; C12N 5/0636

See application file for complete search history.

(56) References Cited

U.S. PATENT DOCUMENTS

| | | | |
|---|---|---|---|
| 2003/0108528 A1* | 6/2003 | Eisenbach-Schwartz et al. | 424/93.7 |
| 2004/0253218 A1 | 12/2004 | Eisenbach-Schwartz et al. | |
| 2005/0123553 A1* | 6/2005 | Monsonego et al. | 424/185.1 |
| 2005/0226857 A1* | 10/2005 | Bonyhadi et al. | 424/93.7 |
| 2008/0159998 A1 | 7/2008 | Ichim | |
| 2009/0010873 A1* | 1/2009 | Eisenbach-Schwartz | A61K 35/15 514/1.1 |
| 2010/0144868 A1 | 6/2010 | Gozin et al. | |
| 2010/0178276 A1* | 7/2010 | Sadelain et al. | 424/93.7 |
| 2010/0284965 A1* | 11/2010 | Fahmy et al. | 424/85.2 |

FOREIGN PATENT DOCUMENTS

| | | | |
|---|---|---|---|
| WO | WO 2004/035768 | | 4/2004 |
| WO | WO/2009/081395 | * | 2/2009 |
| WO | WO 2009/081395 | | 7/2009 |
| WO | WO 2009/155069 | | 12/2009 |
| WO | WO 2010/099205 | | 9/2010 |
| WO | WO 2012/066495 | | 5/2012 |

OTHER PUBLICATIONS

Fisher et al (PLOS One 2010,5 , e10830.*
Faden et al Critical Rev Neurobiology 1993;7(3-4):175-86.*
Farkas et al (Prog. Brain Res., 2007, 161, 43-59.*
Jackowski British J NeuroSurgery, 1995;9(3):303-17, abstract only.*
Munro Neurosignals 2009;17:311-327.*
Weiner et al Nature Review Immunology , May 2006;6(5):404-16. May 2006;6(5):404-16.*
Kramer et al Nature Med. 1995, 1162-1166.*
Communication Pursuant to Article 94(3) EPC dated Nov. 28, 2014 From the European Patent Office Re. Application No. 11841247.7.
Supplementary European Search Report and the European Search Opinion dated Mar. 21, 2014 From the European Patent Office Re. Application No. 11841247.7.
Farkas et al. "Beta-Amyloid Peptide-Induced Blood-Brain Barrier Disruption Facilities T-Cell Entry Into the Rat Brain", Acta Histochemica, XP004632005, 105(2): 115-125, Jan. 1, 2003. p. 117, l-h col. Para 1, r-h col. Para 1, 2, p. 120, l-h col.-r-h col. Discussion, p. 122.
Fisher et al. "Th1 Polarization of T Cells Injected Into the Cerebrospinal Fluid Induces Brain Immunosurveillance", The Journal of Immunology, XP002721043, 192(1): 92-102, Jan. 1, 2014.
Communication Pursuant to Rules 70(2) and 70a(2) EPC dated Apr. 8, 2014 From the European Patent Office Re. Application No. 11841247.7.
International Search Report and the Written Opinion dated Aug. 31, 2012 From the International Searching Authority Re. Application No. PCT/IB2011/055144.

(Continued)

*Primary Examiner* — Anoop K Singh

(57) ABSTRACT

Provided is a method of treating a pathology associated with neural damage, the method comprising administering non-antigen specific polyclonal activated T cells and/or genetically modified T cells into the brain in a manner which prevents meningoencephalitis in the subject, thereby treating the pathology associated with neural damage. Also provided are devices for intrabrain and intrathecal administration of T cells, which comprise the brain-specific or non-antigen specific polyclonal activated T cells and/or genetically modified T cells and a catheter for intrabrain administration in a manner which prevents meningoencephalitis in a subject.

8 Claims, 29 Drawing Sheets
(18 of 29 Drawing Sheet(s) Filed in Color)
Specification includes a Sequence Listing.

(56) References Cited

OTHER PUBLICATIONS

Invitation to Pay Additional Fees dated May 25, 2012 From the International Searching Authority Re. Application No. PCT/IB2011/055144.
Alam et al. "Strategy for Effective Brain Drug Delivery", European Journal of Pharmaceutical Sciences, 40: 385-403, 2010.
Bakhshi et al. "Implantable Pumps for Drug Delivery to the Brain", Journal of Neuro-Oncology, 26: 133-139, 1995.
Fisher et al. "T Cells Specifically Targeted to Amyloid Plaques Enhance Plaque Clearance in a Mouse Model of Alzheimer's Disease", PLoS One, 5(5): e 10830: 1-11, May 2010.
Furlan et al. "Intrathecal Delivery of IFN-{Gamma} Protects C57BL/6 Mice From Chronic-Progressive Experimentsl Autoimmune Encephalomyelitis by Increasing Apoptosis of Central Nervous System-Infiltrating Lymphocytes", The Journal of Immunology, 167(3): 1821-1829, 2001.
Geiger et al. "Survivable Stereotaxic Surgery in Rodents", Journal of Visualized Experiments, JoVE, p. 1-2, 2008.
Linker et al. "Functional Role of Brain-Derived Neurotrophic Factor in Neuroprotective Autoimmunity: Therapeutic Implications in a Model of Multiple Sclerosis", Brain, 133: 2248-2263, 2010.
Monsonego et al. "Aβ-Induced Meningoencephalitis Is IFN-γ-Dependent and Is Associated With T Cell-Dependent Clearance of Aβ in a Mouse Model of Alzheimer's Disease", Proc. Natl. Acad. Sci. USA, PNAS, 103(13): 5048-5053, Mar. 28, 2006.
Radde et al. "Aβ42-Driven Cerebral Amyloidosis in Transgenic Mice Reveals Early and Robust Pathology", EMBO Reports, 7(9): 940-046, 2006.
Weiner et al. "Immunology and Immunotherapy of Alzheimer's Disease", Nature Reviews Immunology, 6(5): 404-416, May 2006. p. 413, Left col., Para 2.
Wekerle et al. "Beneficial Brain Autoimmunity?", Brain, 133: 2181-2183, 2010.
Zota et al. "HLA-DR Alleles in Amyloid β Peptide Autoimmunity: A Highly Immunogenic Role for the DRB1 1501 Allele", The Journal of Immunology, 183(5): 1-5, Aug. 12, 2009.
International Preliminary Report on Patentability dated May 30, 2013 From the International Bureau of WIPO Re. Application No. PCT/IB2011/055144.
Communication Pursuant to Article 94(3) EPC dated Jun. 18, 2015 From the European Patent Office Re. Application No. 11841247.7.
Office Action dated Apr. 4, 2016 From the Israel Patent Office Re. Application No. 226359 and Its Translation Into English.
Communication Pursuant to Article 94(3) EPC dated Nov. 9, 2015 From the European Patent Office Re. Application No. 11841247.7.
Benilova et al. "The Toxic A[Beta] Oligomer and Alzheimer's Disease: an Emperor in Need of Clothes," Nature Neuroscience 15 (2012): 349-357. Abstract.
Blurton-Jones et al. "Neural Stem Cells Improve Cognition Via BDNF in a Transgenic Model of Alzheimer Disease", Proc. Natl. acad. Sci. USA, PNAS, 106(32): 13594-13599, Aug. 11, 2009.
Citron et al. "Mutant Presenilins of Alzheimer's Disease Increase Production of 42-Residue Amyloid Beta-Protein in Both Transfected Cells and Transgenic Mice," Nature Medicine 3 (1997): 67-72. Abstract.
Cunningham et al. "Microglia and Neurodegeneration: The Role of Systemic Inflammation", GLIA, 61(1): 71-90, Published Online Jun. 6, 2012.
Cusimano et al. "Transplanted Neural Stem/Precursor Cells Instruct Phagocytes and Reduce Secondary Tissue Damage in the Injured Spinal Cord", Brain: A Journal of Neurology, 135(Pt.2): 447-460, Advance Access Jan. 23, 2012.
Fisher et al. "Th1 Polarization of T Cells Injected Into the Cerebrospinal Fluid Induces Brain Immunosurveillance", The Journal of Immunology, 192(1): 92-102, Published Online Dec. 4, 2013.
Haass et al. "Soluble Protein Oligomers in Neurodegeneration: Lessons From the Alzheimer's Amyloid Beta-Peptide", Nature Reviews: Molecular Cell Biology, 8(2): 101-112, Feb. 2007.
Ostenfeld et al. "Human Neural Precursor Cells Express Low Levels of Telomerase In Vitro and Show Diminishing Cell Proliferation With Extensive Axonal Outgrowth Following Transplantation", Experimental Neurology, 164(1): 215-226, Jul. 2000.
Perry et al. "The Impact of Systemic Infection on the Progression of Neurodegenerative Disease," Nature Reviews Neuroscience 4 (2003): 103-112. Abstract.
Pluchino et al. "How Stem Cells Speak With Host Immune Cells in Inflammatory Brain Diseases", GLIA, 61(9): 1379-1401, Published Online Apr. 30, 2013.
Pluchino et al. "Human Neural Stem Cells Ameliorate Autoimmune Encephalomyelitis in Non-Human Primates", Annals of Neurology, 66(3): 343-354, Sep. 2009.
Pluchino et al. "Injection of Adult Neurospheres Induces Recovery in a Chronic Model of Multiple Sclerosis", Nature, 422(6933): 688-694, Apr. 17, 2003.
Pluchino et al. "Neurosphere-Derived Multipotent Precursors Promote Neuroprotection by an Immunomodulatory Mechanism", Nature, 436(7048): 266-271, Jul. 14, 2005.
Pluchino et al. "Persistent Inflammation Alters the Function of the Endogenous Brain Stem Cell Compartment", Brain: A Journal of Neurology, 131(10): 2564-2578, Advance Access Publication Aug. 30, 2008.
Thier et al. "Direct Conversion of Fibroblasts Into Stably Expandable Neural Stem Cells", Cell Stem Cell, 10(4): 473-479, Apr. 6, 2012.
Yamasaki et al. "Neural Stem Cells Improve Memory in an Inducible Mouse Model of Neuronal Loss", The Journal of Neuroscience, 27(44): 11925-11933, Oct. 31, 2007.

\* cited by examiner

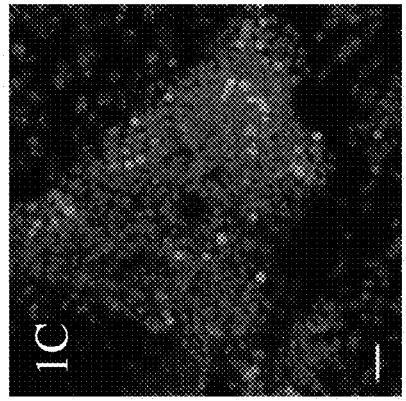
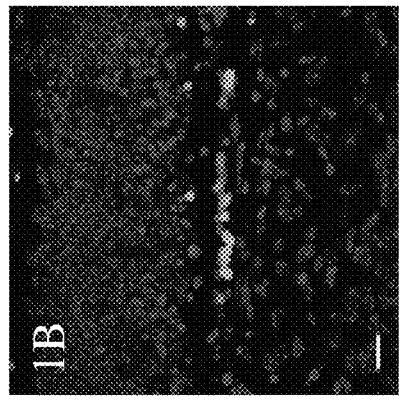
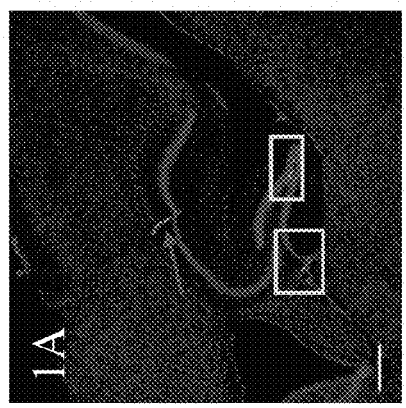
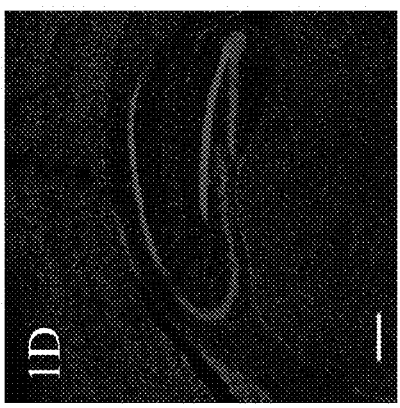

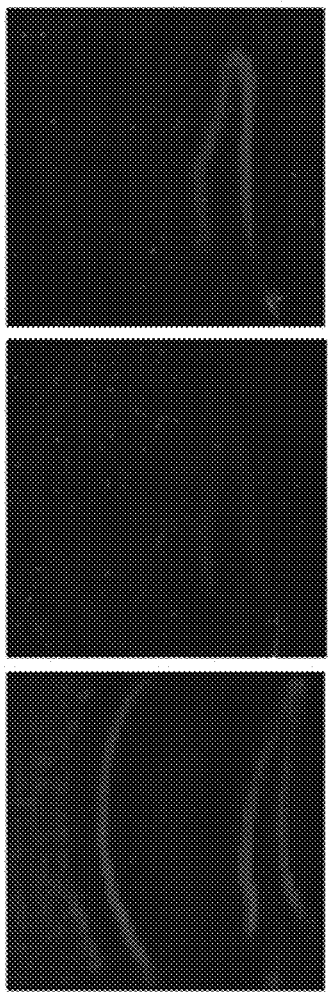
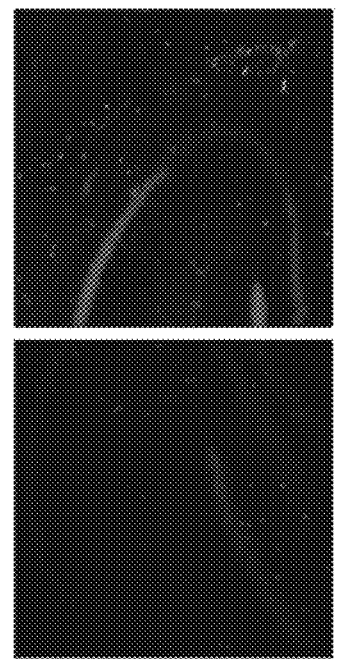
Entry of OVA-specific CD4 T-cells to the brain is IFN-γ-depended
0.005μg/ml OVA  FIG. 3A
0.05μg/ml OVA  FIG. 3B
2μg/ml OVA  FIG. 3C
FIG. 3D
FIG. 3E 5 dpi 14 dpi 27 dpi

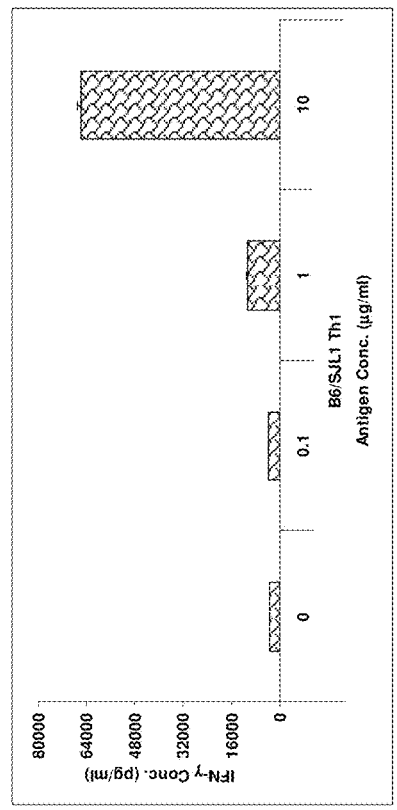
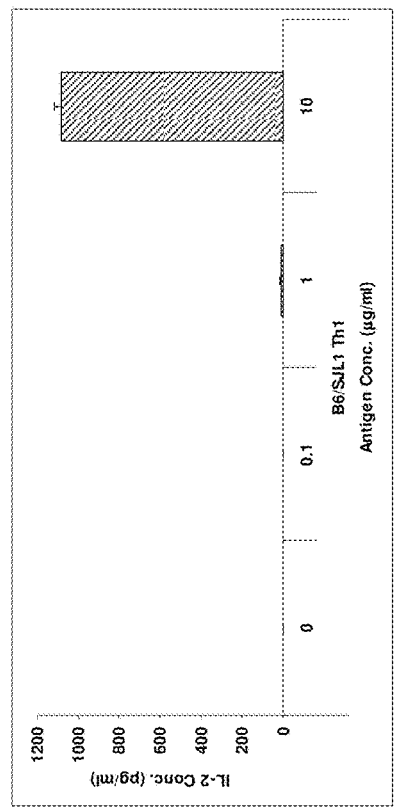
FIG. 5A
FIG. 5B

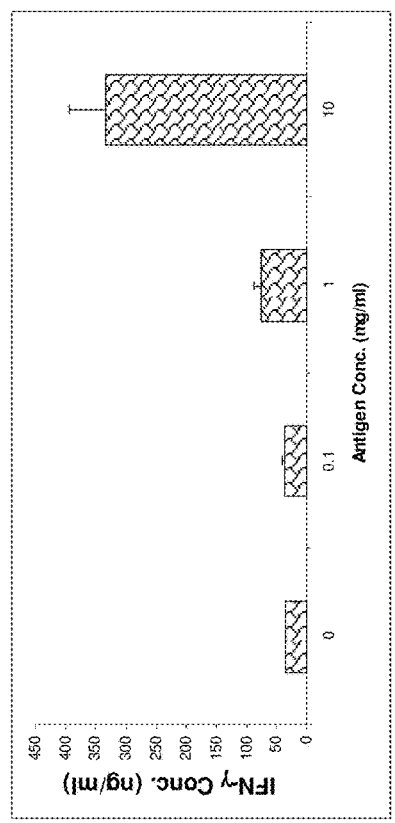
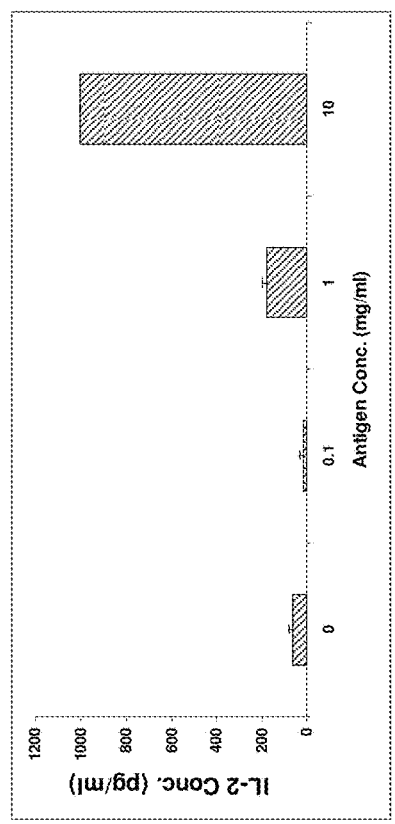
FIG. 7A
FIG. 7B

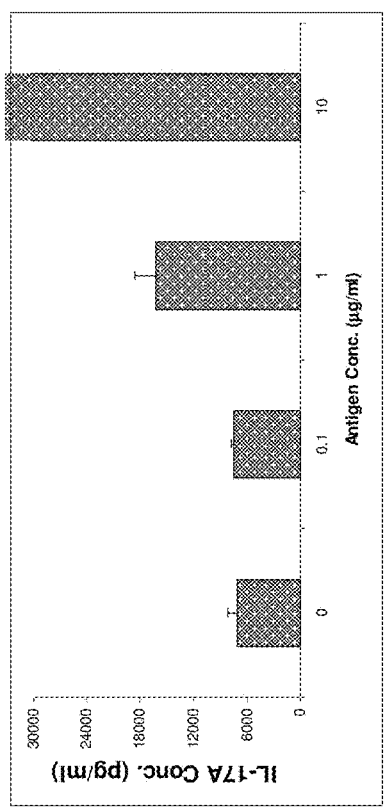
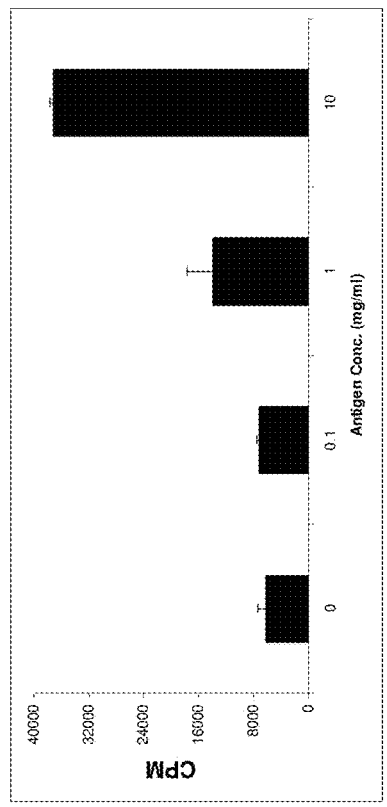
FIG. 7E
FIG. 7F

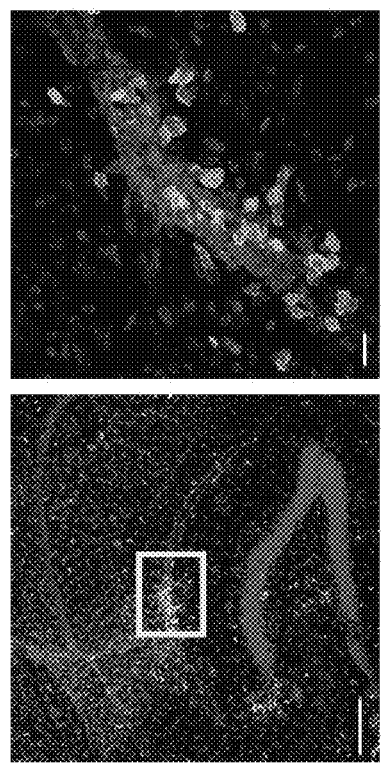

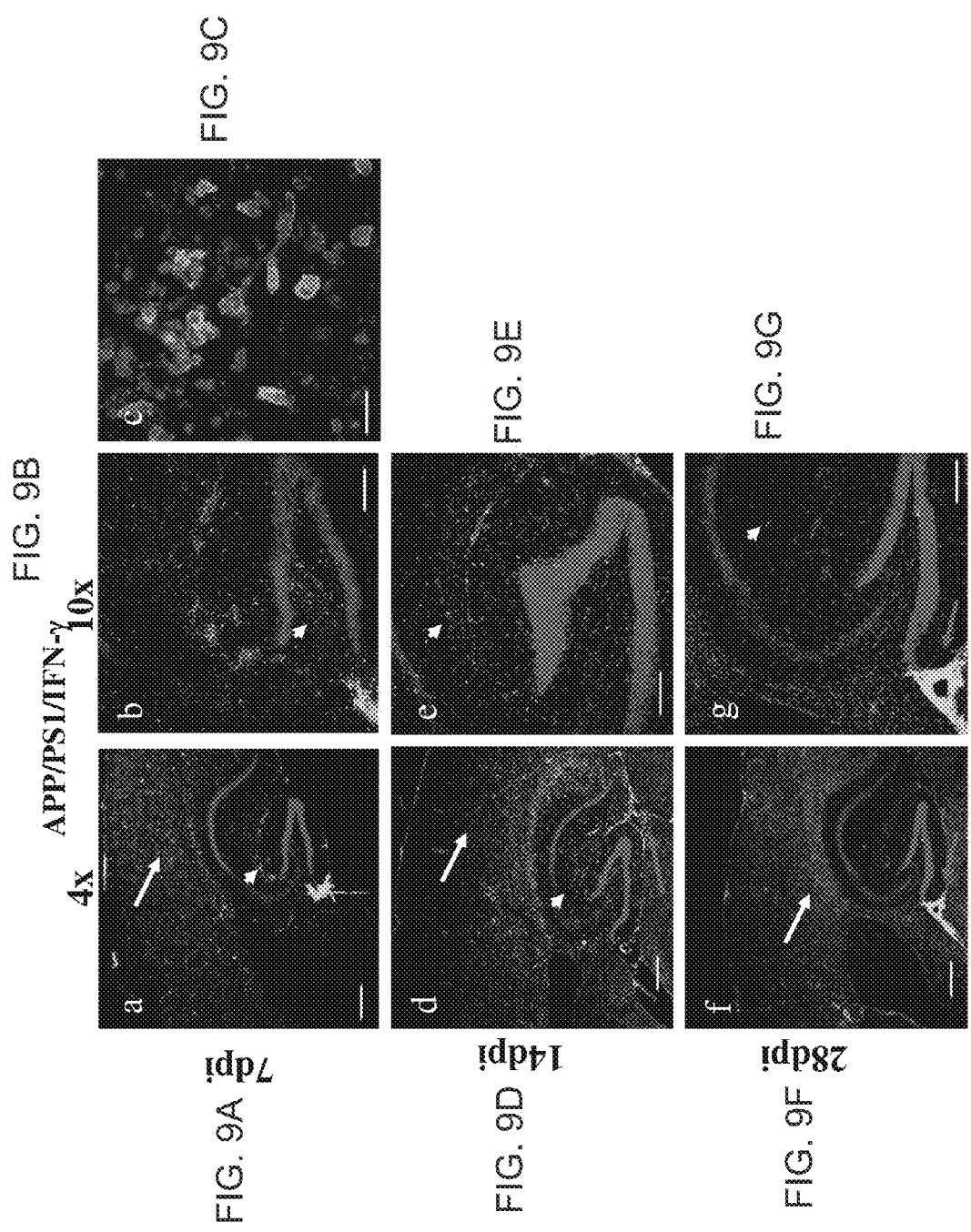

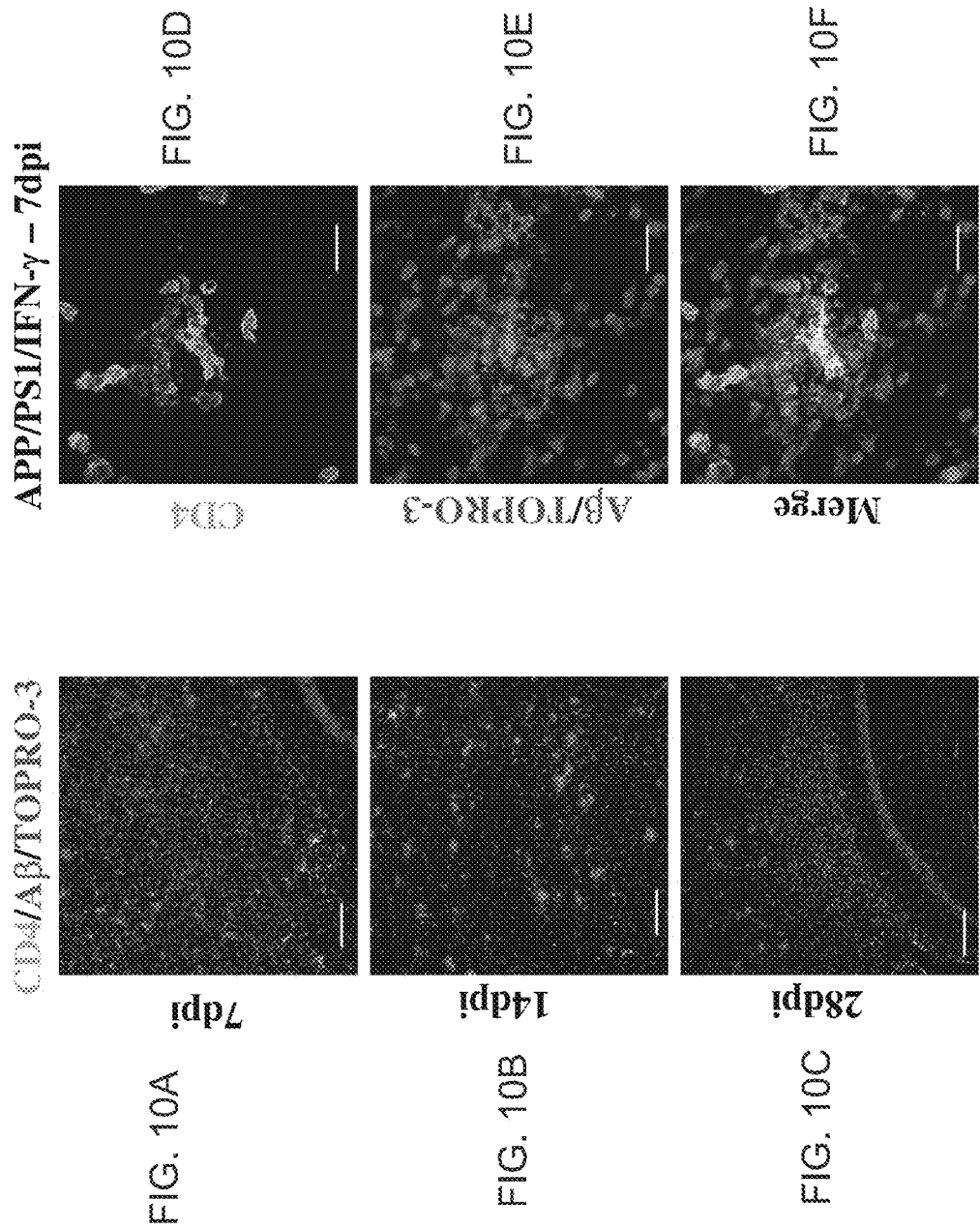

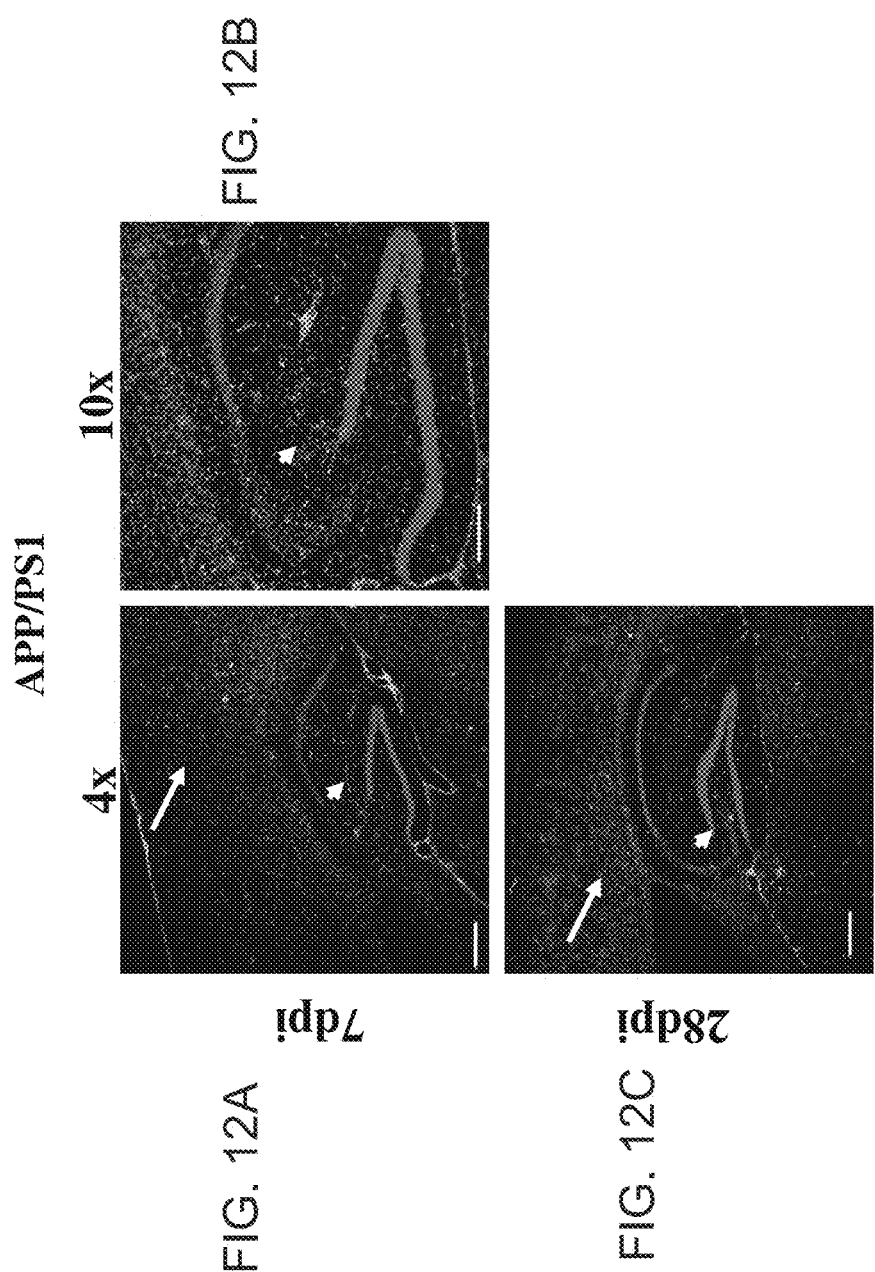

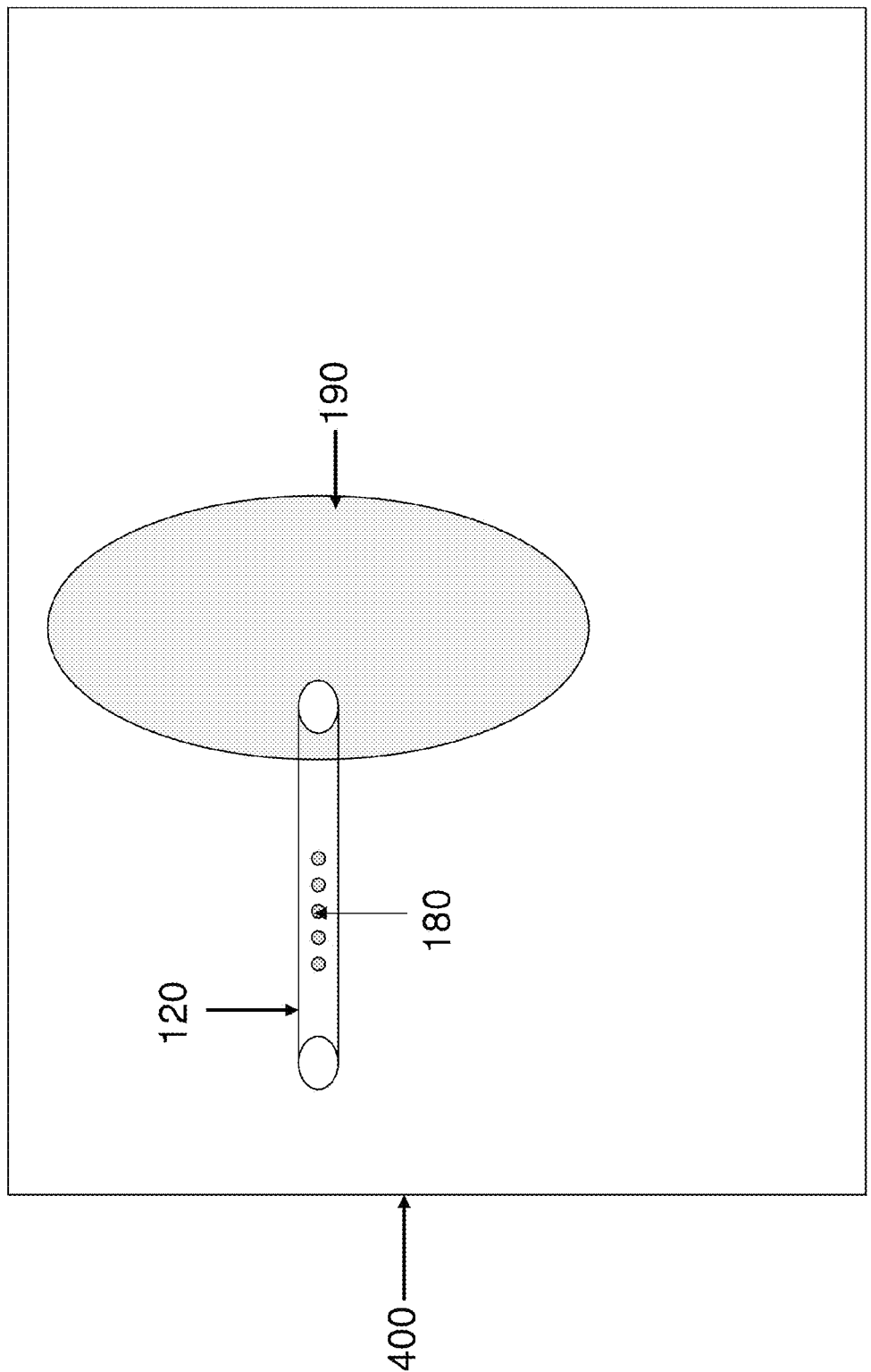

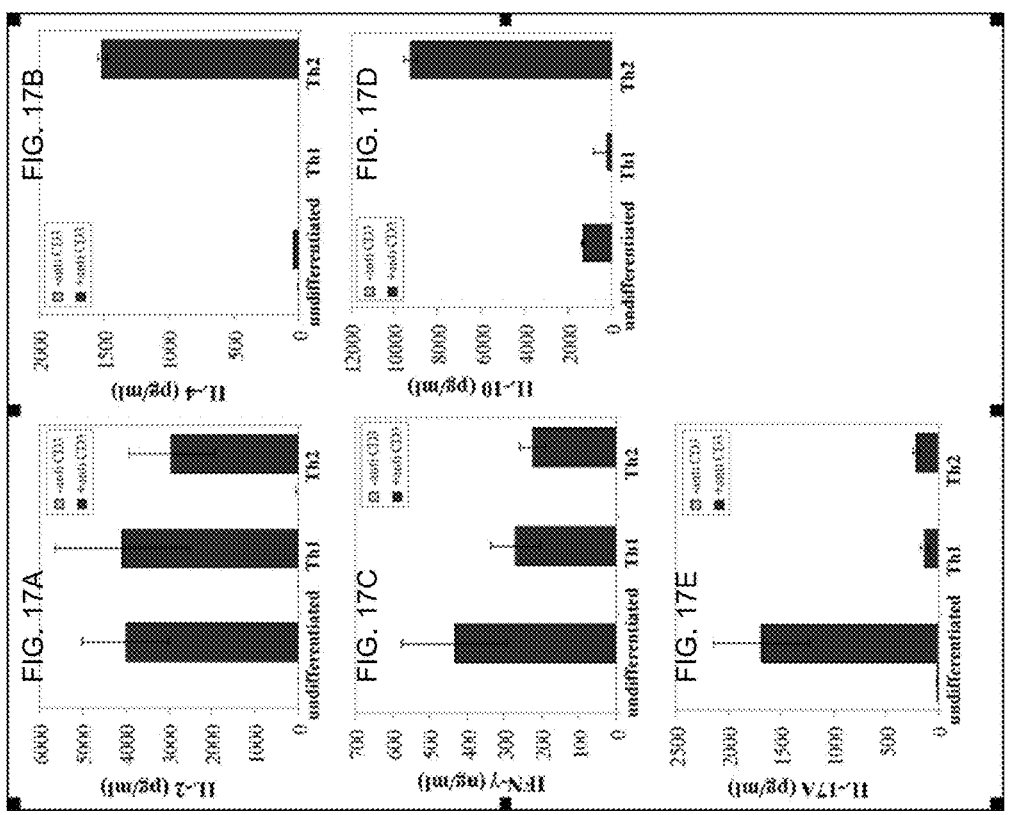

anti-CD3 stimulated infected line anti-CD3CD28 stimulated

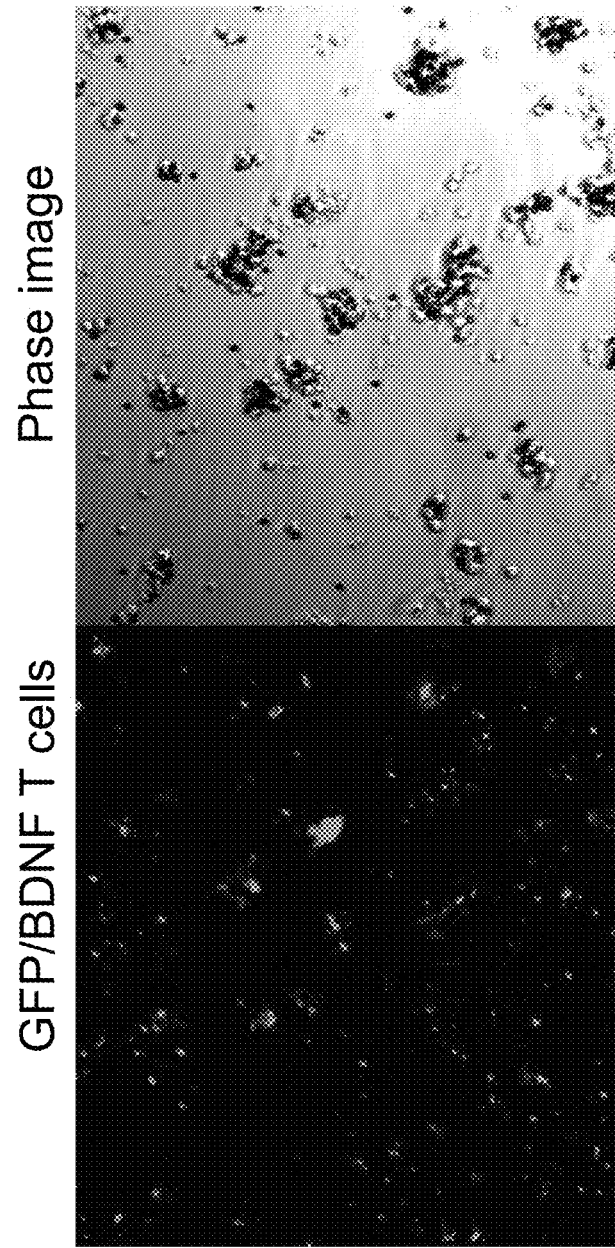

ial filing date of Nov. 17, 2011, which claims the benefit of
T-CELL THERAPY TO NEURODEGENERATIVE DISEASES

RELATED APPLICATIONS

This application is a National Phase of PCT Patent Application No. PCT/IB2011/055144 having International filing date of Nov. 17, 2011, which claims the benefit of priority under 35 USC § 119(e) of U.S. Provisional Patent Application No. 61/414,453 filed on Nov. 17, 2010. The contents of the above applications are all incorporated by reference as if fully set forth herein in their entirety.

SEQUENCE LISTING STATEMENT

The ASCII file, entitled 56538SequenceListing.txt, created on May 1, 2013, comprising 658,428 bytes, submitted concurrently with the filing of this application is incorporated herein by reference.

FIELD AND BACKGROUND OF THE INVENTION

The present invention, in some embodiments thereof, relates to methods and devices for treating pathologies associated with neural damage such as neurodegenerative diseases and to methods of administering a protein-of-interest into a brain of a subject, and more particularly, but not exclusively, to intracranial (IC), intracerebroventricular (ICV) or intrathecal administration of T cells.

Alzheimer disease (AD) is currently considered as the leading cause of dementia among older people and accounts for 60-70% of all dementia cases. It is characterized by a progressive loss of neural cell populations and cognitive decline. Every year, 4.6 million new cases of dementia are reported worldwide. By 2050, it is projected that there will be 100 million people with dementia in the world. The disease is identified by the accumulation of amyloid beta (Aβ) in the hippocampal and cortical areas of the brain, often associated with neurofibrillary tangles caused by hyperphosphorylation of the cytoskeleton protein Tau. The involvement of the immune system in the development and progression of neurodegenerative diseases in general and in AD in particular, is now widely accepted and demonstrated in numerous studies (McGeer, P. L., and E. G. McGeer. 2006; McGeer, P. L., et al., 2006). However, the conventional immunotherapy approaches for AD had only limited clinical results.

Neurogenesis is an intense and dynamic process that maintains the proliferation, migration, and maturation of new neurons. The adult brain contains neural stem cells (NSCs) that self-renew, proliferate and give rise to neural progenitor cells (NPCs) that exhibit partial lineage-commitment. The NSCs differentiate into three major types of central nervous system (CNS) cells: neurons, astrocytes, and oligodendrocytes. Two neurogenic areas are present in the adult brain: the subventricular zone (SVZ) and the dentate gyrus (DG) of the hippocampus, known as the neurogenic niche. With aging, the proliferation and differentiation of NPCs are significantly suppressed, primarily in the DG. It is suggested that the microenvironment of the SVZ and DG provides special conditions which support neurogenesis. Another aspect that may negatively affect neurogenesis is the reduced level of neurotrophic factors, such as brain-derived neurotrophic factor (BDNF) and IGF-1/IGF-2 in the neurogenic niche. BDNF was shown to increase the strength of potentiated synapses and also to promote survival and differentiation of Neural stem cells (NSCs).

Neurogenesis was found to be increased in the brains of patients with AD compared to age-matched control subjects, suggesting that there are mechanisms in the brain directed to overcoming the loss of function. In contrast, different mouse models of AD have shown either reduced or enhanced neurogenesis in the dentate gyrus (DG).

In recent years accumulated evidences have indicated that the neurogenic process is negatively and positively affected by the immune system (Ziv Y, et al. Nat Neurosci. 2006, 9: 268-75; Butovsky O, et al. Mol Cell Neurosci. 2006, 31: 149-60; Baron R, et al. FASEB J. 2008, 22: 2843-52; Aharoni R, et al. J. Neurosci. 2005, 25: 8217-28). In particular, the role of CD4+ T cells in neurogenesis has created considerable interest in light of findings demonstrating that auto-antigen-specific T cells are key players in functional recovery of injured neurons.

It is now believed that the central nervous system (CNS) is not immune privileged and that there is important crosstalk between the CNS and immune cells which is crucial for CNS maintenance and repair. Nonetheless, in slowly progressing diseases of the ageing brain, the immune response required for tissue repair is impaired and needs proper stimulation. It has been shown that in acute CNS damage administration of ex-vivo activated macrophages enhances healing (Shechter, R., A. et al., 2009). This is partially due to the fact that in various acute instances, failure of the blood brain barrier (BBB) enables immune cellular components to infiltrate into the brain. It has been shown that following acute injury to the CNS, certain lymphocytes migrate into the brain and promote recovery (Moalem, G., et al., 1999. Differential T cell response in central and peripheral nerve injury: connection with immune privilege. *Faseb J* 13:1207-1217).

Various studies showed that migration of peripheral immune components to the CNS can be dangerous. Thus, clinical trials showed that immunization with Aβ is associated with menigoencephalitis (Orgogozo, J. M., et al., 2003. Subacute meningoencephalitis in a subset of patients with AD after Abeta42 immunization. *Neurology* 61:46-54.). In addition, immunization of mice with Aβ is associated with entry of cytotoxic CD8 T cells, and brain hemorrhages caused by Aβ antibodies (Gandy, S., and L. Walker. 2004. Toward modeling hemorrhagic and encephalitic complications of Alzheimer amyloid-beta vaccination in nonhuman primates. *Curr Opin Immunol* 16:607-615; Pfeifer, M., et al. 2002. Cerebral hemorrhage after passive anti-Abeta immunotherapy. *Science* 298:1379).

Monsonego, A., J. et al., 2006 (Abeta-induced meningoencephalitis is IFN-{gamma}-dependent and is associated with T cell-dependent clearance of Abeta in a mouse model of Alzheimer's disease. *Proc Natl Acad Sci USA* 103:5048-5053) show that infiltration of T lymphocytes into the CNS in the presence of low level of expression of IFNγ following Aβ immunization of humanized AD Tg-mice is accompanied by meningocephalitis. These T lymphocyte cells specifically targeted Aβ plaques and consequently enhance their removal (Fisher, Y., A. Nemirovsky, R. Baron, and A. Monsonego. T cells specifically targeted to amyloid plaques enhance plaque clearance in a mouse model of Alzheimer's disease. *PLoS One* 5:e10830).

U.S. Patent Application No. 20030108528 (Eisenbach-Schwartz, Michal, et al.) describes a method of treating injury or disease of the central nervous system using non-recombinant activated antiself T-cells that recognize an antigen of the nervous system (NS) or a peptide derived therefrom to promote nerve regeneration or to prevent or inhibit axonal degeneration within the NS.

U.S. Patent Application No. 20040253218 (Eisenbach-Schwartz, Michal, et al.) describes methods of promoting nerve regeneration, conferring neuroprotection and preventing neuronal degeneration within the nervous system by administering a nervous system-specific activated T cells, or a nervous system-specific antigen.

U.S. Patent Application No. 20050123553 (Monsonego, Alon et al.) describes novel compositions containing an amyloid beta peptide and methods of using these compositions for treating and preventing Aβ-protein related (e.g., an amyloid fibril) disorders such as Alzheimer's disease.

U.S. Patent Application No. 20100144868 (Gozin; Michael et al.) describes hybrid compounds having a fullerene core residue, bioavailability enhancing moieties and glutamate receptor ligand residues, whereby the bioavailability enhancing moiety allows the compound to reach an effective concentration in physiological media and pass the blood-brain barrier for the treatment of medical conditions associated with oxidative stress and/or neural damage, such as, for example, neurological diseases, disorders and trauma.

WO 2009/081395 (Monsonego A) describes compositions and methods for treating a subject suffering from a disease of the nervous system, associated with an inflammatory response, the compositions include an agent which increases brain levels of interferon-γ; and an agent which reduces the number of brain T regulatory (Treg) cells, and optionally an agent which suppresses neurotoxic inflammatory brain responses.

CD4 T cells are divided into several sub-populations, characterized by their cytokine secretion profile and their roles in immunity. The most common sub-populations are the Th1, Th2 and Th17 T cells. Th1 cells are inflammatory cells secreting the growth factor IL-2 and the effector cytokine IFN-γ. These cells are known for their role in macrophage stimulation, enhancing their phagocyte activity. Th2 cells are anti-inflammatory cells secreting the growth factors IL-2 and IL-4 and the effector cytokines IL-10 and TGFβ known also as regulatory cytokines. Th2 cells are best known for their role in supporting antibody production from plasma cells. Th17 cells were only recently characterized and they are classified by IL-17A as their effector cytokine. They have been shown to be highly proinflammatory cells and function in eliminating large extra-cellular parasites mainly by recruiting neutrophils.

Monsonego, A. et al., 2003 (Increased T cell reactivity to amyloid beta protein in older humans and patients with Alzheimer disease. *J Clin Invest* 112:415-422) describe a remarkably increased frequency of Aβ-specific T cells in healthy older individuals and in patients with AD.

Additional background art includes Zota V., et al., 2009 [J. Immunol. 183(5):3522-30. Epub 2009 Aug. 12]; Clemons-Miller A R, et al. [Clin Cancer Res. 2001 March; 7(3 Suppl):917s-924s. Intrathecal cytotoxic T-cell immunotherapy for metastatic leptomeningeal melanoma]; Furlan R, et al. [J. Immunol. 2001, 167(3):1821-9]; Penn R D, et al. [Neurosurgery. 1997; 40:94-9]; McAdoo J D, et al. [Neurosci Lett. 2005; 381(3):305-8]; Ruggiero A, et al. 2001. [Paediatr Drugs; 3:237-46]; Wekerle H and Hohlfeld R. [Brain, 2010, 133:2180-2184]; and Linker R A., et al. [2010. Brain 133:2248-2263].

SUMMARY OF THE INVENTION

According to an aspect of some embodiments of the present invention there is provided a method of treating a pathology associated with neural damage, the method comprising administering non-antigen specific polyclonal activated T cells into the brain in a manner which prevents meningoencephalitis in the subject, thereby treating the pathology associated with neural damage.

According to an aspect of some embodiments of the present invention there is provided a method of administering a protein-of-interest into a brain of a subject, the method comprising administering a genetically modified T cell capable of expressing the protein-of-interest into the brain in a manner which prevents meningoencephalitis in the subject, thereby administering the protein-of-interest into the brain of the subject.

According to an aspect of some embodiments of the present invention there is provided a method of treating a pathology associated with neural damage, the method comprising administering the protein-of-interest according to the method of some embodiments of the invention into a brain of a subject in need thereof, wherein the protein-of-interest is capable of treating the pathology associated with neural damage, thereby treating the pathology associated with neural damage.

According to an aspect of some embodiments of the present invention there is provided a method of treating a pathology associated with neural damage, the method comprising administering by intracerebroventricular (ICV) or intrathecal administration a polyclonal activated T cell into the brain, thereby treating the pathology associated with neural damage.

According to an aspect of some embodiments of the present invention there is provided a device for intra brain administration, comprising a catheter and a non-antigen specific polyclonal activated T cell.

According to an aspect of some embodiments of the present invention there is provided a device for intra brain administration, comprising a catheter and a genetically modified T cell.

According to an aspect of some embodiments of the present invention there is provided a device for intracerebroventricular (ICV) or intrathecal administration, comprising a catheter and a polyclonal activated T cell.

According to some embodiments of the invention, the non-antigen specific polyclonal activated T cell expresses interferon gamma.

According to some embodiments of the invention, the non-antigen specific polyclonal activated T cell is genetically modified.

According to some embodiments of the invention, the genetically modified activated T cell is capable of expressing a protein-of-interest.

According to some embodiments of the invention, the protein-of-interest is capable of treating the neurodegenerative disease.

According to some embodiments of the invention, the genetically modified T cell is a non-activated T cell.

According to some embodiments of the invention, the administering is effected by intracranial (IC), intracerebroventricular (ICV) or intrathecal administration.

According to some embodiments of the invention, the intra brain administration is effected by intracranial (IC), intracerebroventricular (ICV) or intrathecal administration.

According to some embodiments of the invention, the T cell accumulates in a hippocampus, cortex and/or cerebellum of the brain.

According to some embodiments of the invention, the T cell accumulates in brain regions affected with neuronal and/or glial damage.

According to some embodiments of the invention, the IC, ICV or intrathecal administration is performed periodically.

According to some embodiments of the invention, the T cell is activated to express the protein-of-interest.

According to some embodiments of the invention, the T cell constitutively expresses the protein-of-interest.

According to some embodiments of the invention, the protein-of-interest is secreted by the T cell.

According to some embodiments of the invention, the activation of the T cell is effected ex-vivo.

According to some embodiments of the invention, the T cell is an autologous T cell of the subject.

According to some embodiments of the invention, the T cell is a non-autologous T cell.

According to some embodiments of the invention, the device is for treating a pathology associated with nervous system damage in a subject.

According to some embodiments of the invention, the pathology associated with nervous system damage comprises a neurodegenerative disease.

According to some embodiments of the invention, the pathology associated with nervous system damage comprises brain injury or stroke.

According to some embodiments of the invention, the neurodegenerative disease is chronic.

According to some embodiments of the invention, the neurodegenerative disease is associated with formation of an amyloid fibril.

According to some embodiments of the invention, the neurodegenerative disease is selected from the group consisting of multiple sclerosis, Lupus eruthromatosis, Alzheimer's disease, Parkinson's Disease, senile dementia, amyotrophic lateral sclerosis, Down's Syndrome, Dutch Type Hereditary Cerebral Hemorrhage Amyloidosis, Reactive Amyloidosis, Familial Mediterranean Fever, Familial Amyloid Nephropathy with Urticaria and Deafness, Muckle-Wells Syndrome, Idiopathic Myeloma, Macroglobulinemia-Associated Myeloma, Familial Amyloid Polyneuropathy, Familial Amyloid Cardiomyopathy, Isolated Cardiac Amyloid, Systemic Senile Amyloidosis, Adult Onset Diabetes, Insulinoma, Isolated Atrial Amyloid, Medullary Carcinoma of the Thyroid, Familial Amyloidosis, Hereditary Cerebral Hemorrhage with Amyloidosis, Familial Amyloidotic Polyneuropathy, Scrapie, Creutzfeldt-Jacob Disease, Gerstmann Straussler-Scheinker Syndrome, Bovine Spongiform Encephalitis, a Prion-mediated disease, and Huntington's Disease.

According to some embodiments of the invention, the activation of the non-antigen specific polyclonal T cell is performed by incubation of a T cell with an anti CD3 antibody, an anti CD28 antibody, phytohaemagglutinin (PHA) and/or Concavalin A.

According to some embodiments of the invention, the activation is antigen-specific activation.

According to some embodiments of the invention, the activation is performed by incubation of the T cell with antigen-presenting cells (APCs).

According to some embodiments of the invention, the activation comprises incubation of the T cell with an anti CD3 antibody, an anti CD28 antibody, phytohaemagglutinin (PHA) and/or Concavalin A.

According to some embodiments of the invention, the antigen-presenting cells (APCs) are loaded with a nervous system specific antigen.

According to some embodiments of the invention, the antigen-presenting cells (APCs) are loaded with a non-nervous system specific antigen.

According to some embodiments of the invention, the activation of the polyclonal activated T cell is non-antigen specific.

According to some embodiments of the invention, the activation of the polyclonal activated T cell is antigen specific.

According to some embodiments of the invention, the activation of the polyclonal activated T cell is a specific activation by a brain-specific antigen.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

The patent or application file contains at least one drawing executed in color. Copies of this patent or patent application publication with color drawing(s) will be provided by the Office upon request and payment of the necessary fee.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 1A-D are images of fluorescence confocal microscopy depicting brain sections following IC injection of naïve non-stimulated CD4 T cells. CD4 T-cells were isolated from the spleen of green fluorescence protein (GFP) transgenic (Tg)-mice (C57BL/6) by negative selection as described in the General Materials and Experimental Methods of the Examples section which follows. Three-month-old wild type (wt) C57BL/6 mice were injected with $2.5 \times 10^5$ naive CD4 GFP T-cells per hemisphere as described in the General Materials and Experimental Methods of the Examples section which follows. The T cells express GFP since they are obtained from the GFP transgenic mice). Mice were killed at different time points after IC injection and analyzed by confocal microscopy. FIG. 1A—Low magnification image of the injected brain three hours post injection. Note limited amounts of T cells (green fluorescence signal) at the site of injection (marked with a red arrow) and the dentate gyrus (right yellow square). FIG. 1B—Higher magnification of the dentate gyrus area. Note presence of T cells (green fluorescence signal) in the dentate gyrus. FIG. 1C—High magnification of the meninges area. Note presence of T cells (green fluorescence signal) in the meninges. FIG. 1D—Low magnification of the injected brain three days post injection. Note that absence of GFP CD4 T cells in the brain of injected mice following three days of injection. Magnifications: FIG. 1A—4×, FIGS. 1B and 1C—40×. FIG. 1D—10×.

Figure 2A:
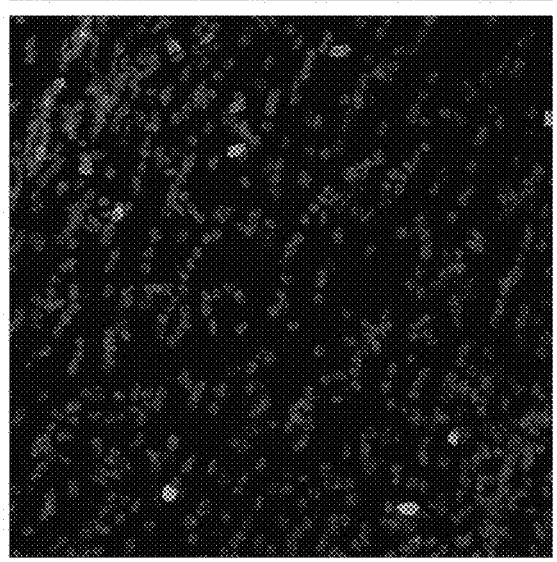
Figure 2B:
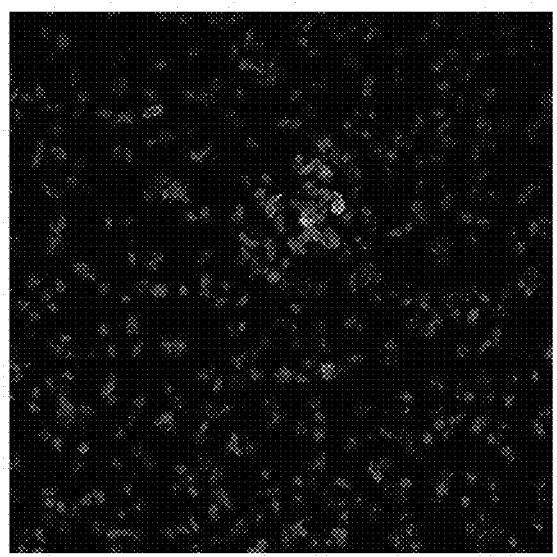
Figure 2C:

FIGS. 2A-C are images of fluorescence microscopy depicting entry of OVA-specific CD4 T-cells to the brain of C57BL/6 mice. CD4 T-cells were isolated from C57BL/6 OT-II Tg mice by negative selection. Cells were activated none-specifically by αCD3/αCD28 stimulation for 48 hours. Three months old wild type C57BL/6 mice were ICV injected with $2.5 \times 10^5$ stimulated CD4 T-cells per hemisphere. Brain sections were removed 5 days post injection (dpi) and were immuno-stained for CD4 T-cells using a green-labeled anti CD4 antibody and counter-stained with TOPRO-3 (blue) for cell nuclei. FIG. 2A—5 dpi, brain parenchyma, magnification 20×; FIG. 2B—5 dpi, brain parenchyma, magnification 20×; FIG. 2C—5 dpi, Low magnification (4×) of the injected brain. Cells are detected around the injection site 5 days after the injection.

FIGS. 3A-E are images of confocal microscopy depicting entry of OVA-specific CD4 T-cells to the brain of C57BL/6 mice following stimulation in-vitro by different concentrations of an OVA peptide [ISQAVHAAHAEINEAGR (SEQ ID NO:118)]. CD4 T-cells were isolated from C57BL/6 OT-II Tg mice by negative selection. Cells were activated specifically by 0.005, 0.05 or 2 µg/ml OVA peptide for 48 hours. Two months old wild type C57BL/6 mice were ICV injected with $2.5 \times 10^5$ stimulated CD4 T-cells per hemisphere. Brain sections were removed 5 days post injection (dpi) and were immuno-stained for CD4 T-cells using a green-labeled anti CD4 antibody and counter-stained with TOPRO-3 (blue) for cell nuclei. FIG. 3A—T cells stimulated ex vivo with 0.005 µg/ml OVA prior to injection into the brain. FIGS. 3B and 3D—T cells stimulated ex vivo with 0.05 µg/ml OVA prior to injection into the brain. FIGS. 3C and 3E—T cells stimulated ex vivo with 2 µg/ml OVA prior to injection into the brain. Note the green fluorescent signal in the hippocampus, cortex and meninges of mice injected with 0.05 µg/ml or 2 µg/ml demonstrating entry of CD4 T cells to the hippocampus, cortex and meninges following OVA activation. Brains from mice injected with cells stimulated with 0.005 µg/ml OVA peptide were completely devoid of CD4 T cells.

Figure 3F:
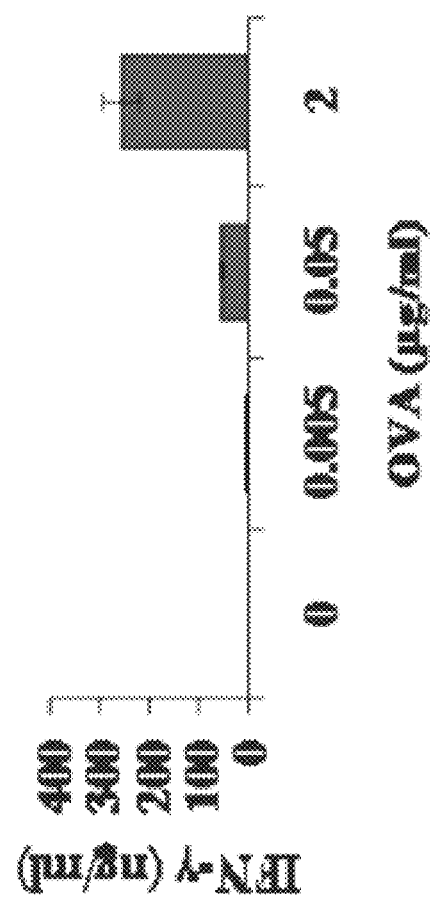

FIG. 3F is a histogram depicting IFN-γ levels secreted by un-stimulated T-cells or by T cells stimulated with 0.005 µg/ml, 0.05 µg/ml or 2 µg/ml OVA peptide in-vitro. Note that while un-stimulated cells did not secret IFN-γ, the OVA-activated T cells secreted IFN-γ in a dose-dependent manner. The levels of IFN-γ detected by ELISA were 5.14±0.73, 56.81±4.04 and 260.63±38.19 ng/ml, respectively.

Figure 4B:
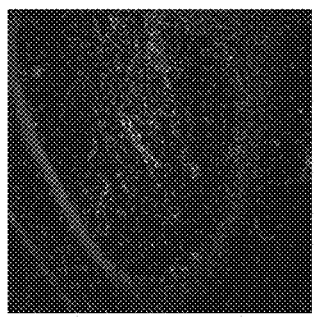
Figure 4D:
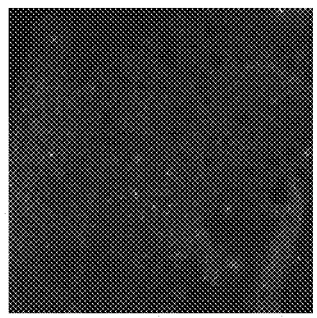
Figure 4A:
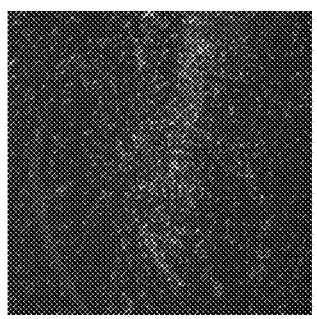
Figure 4C:
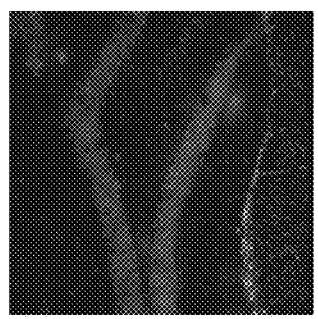
Figure 4E:
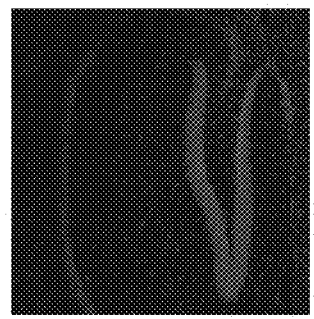
Figure 4F:
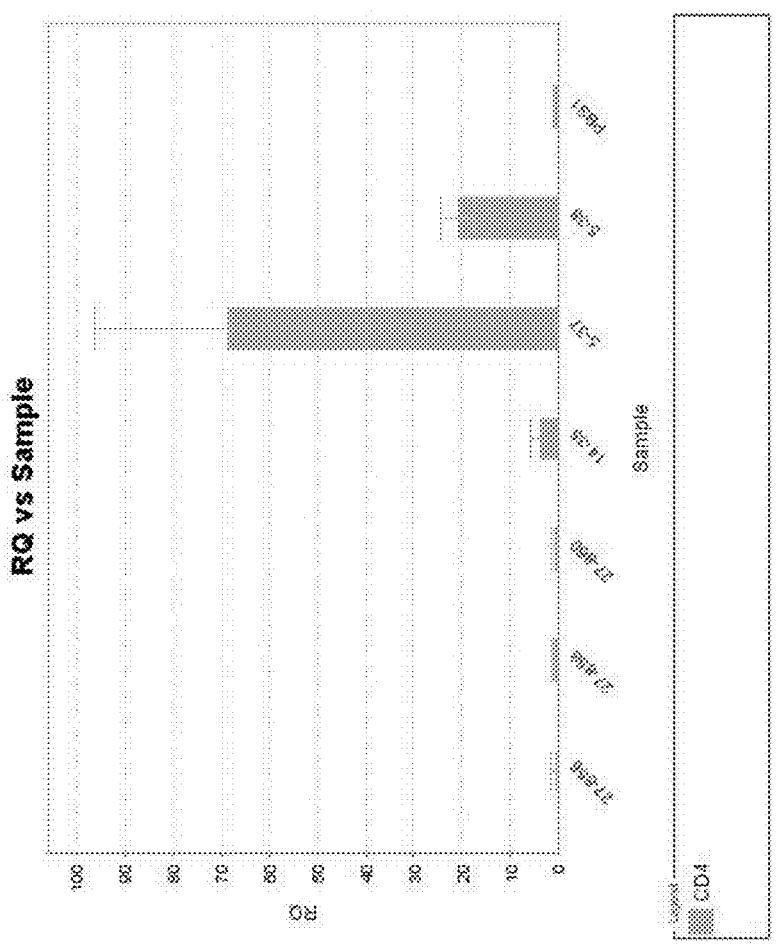
Figure 4H:
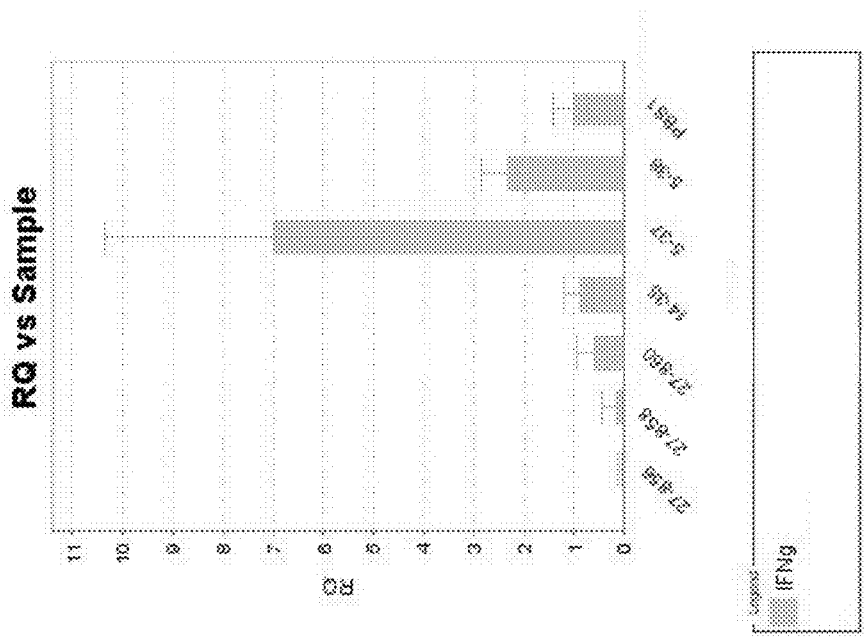
Figure 4G:
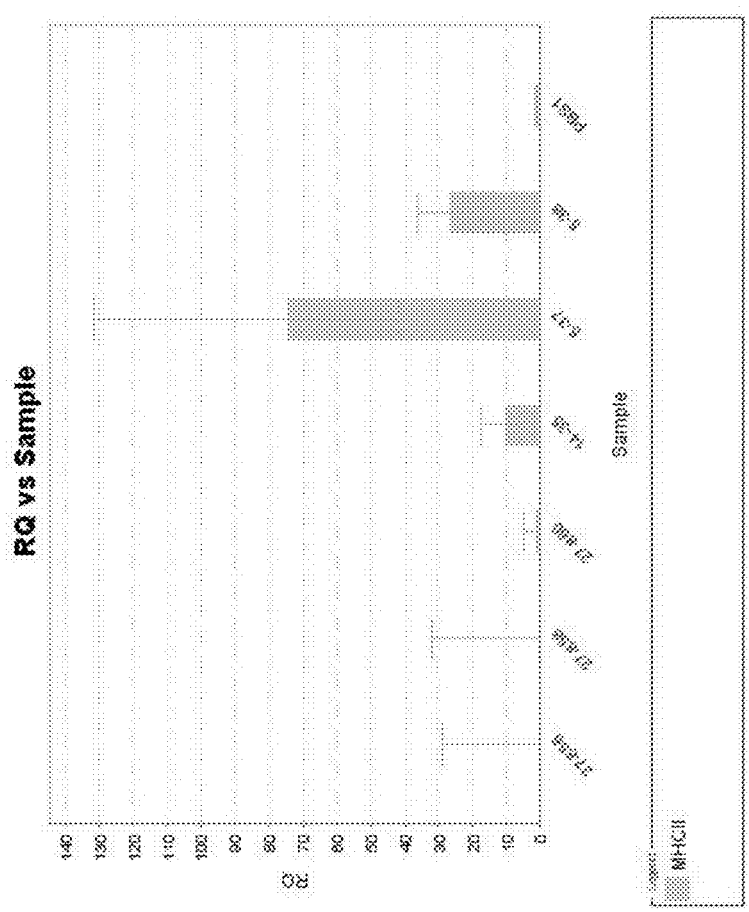

FIGS. 4A-H demonstrate entry of polyclonal-activated Aβ-specific CD4 T-cells to the brain of B6/SJL mice in the absence of specific stimulation. Aβ-specific CD4 T-cells were activated none-specifically by αCD3/αCD28 antibodies for 48 hours. WT (B6/SJL) mice were ICV injected with $2.5 \times 10^5$ stimulated CD4 T-cells per hemisphere. FIGS. 4A-E are images of fluorescence microscopy of brain sections. Brains were removed 5 (FIGS. 4A-B, dentate gyrus and cortex regions, magnification 10×), 14 (FIGS. 4C-D, dentate gyrus and meningial regions, magnification 10×) in C and D) and 27 (FIG. 4E, dentate gyrus and cortex regions, magnification 10×) days post injection (dpi) and the brain sections were immuno-stained for CD4 T-cells using a green-labeled anti CD4 antibody and counter-stained with TOPRO-3 (blue) for cell nuclei. Note that numerous CD4 cells were detected at the brain parenchyma 5 dpi (FIGS. 4A-B). The residual CD4 cells detected at 14 dpi were located mainly in the ventricle and meningial regions of the brains (FIGS. 4C-D). 27 dpi no CD4 T-cells were detected (FIG. 4E). The results show that stimulated Ab-specific CD4 T cells enter the brain parenchyma of WT Mice. FIGS. 4F-H—are histograms depicting RT-PCR analyses of CD4 (FIG. 4F), CD74 (MHC class II; FIG. 4G) and IFN-γ (FIG. 4H) expression in brains, demonstrating the kinetics of CD4, MHC class II and IFN-γ expression in the brains of mice injected with CD4 Aβ-Specific T Cells. Mice were injected with activated T-cells or PBS, sacrificed 5 (samples 5-37 and 5-38), 14 (sample 14-35) or 27 (sample 27-856, 27-858, or 27-860) days post injection, and the expression level of CD4, CD74 and IFN-γ was measured in the activated T-cell-injected mice relative to mice injected with PBS only (sample PBS1). Note that the high level of expression of the CD4, CD74 and IFN-γ detected at 5 dpi is evidently decreasing 14 and 27 dpi. The results show that stimulated Ab-specific CD4 T cells enter the brain parenchyma of WT Mice.

Figure 5C:
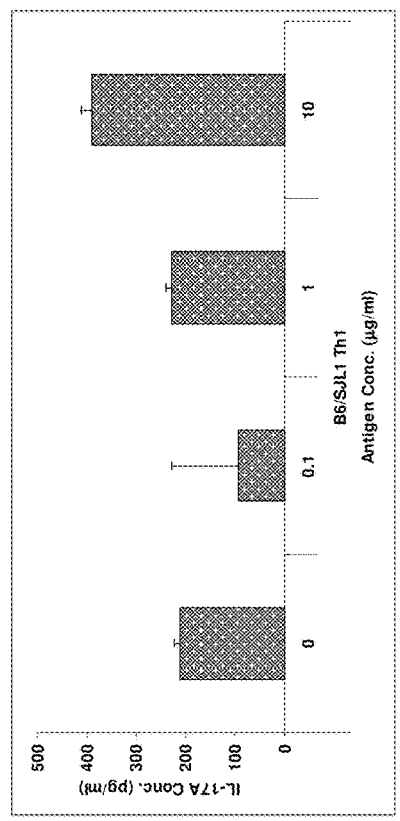
Figure 5D:
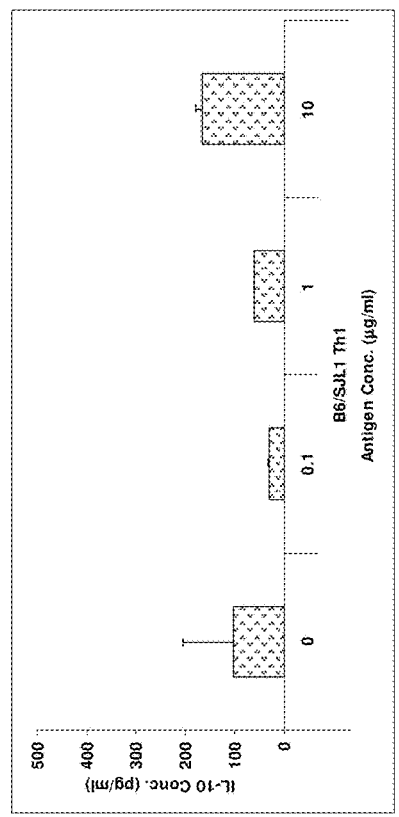
Figure 5E:
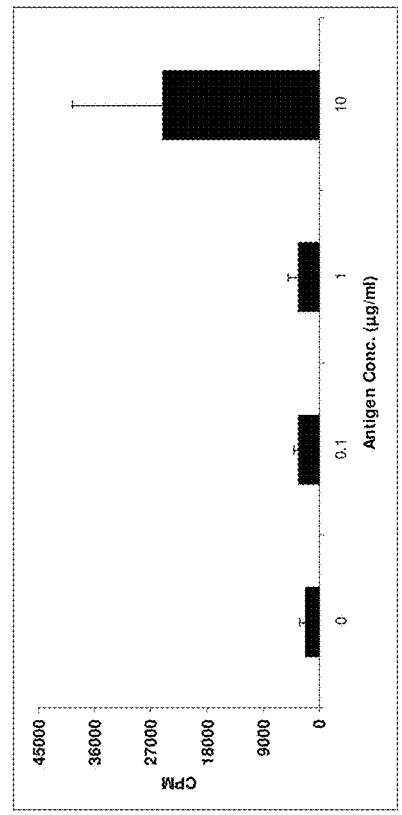

FIGS. 5A-E depict generation of Aβ-specific Th1 T-cells. Cultured T-cells isolated from $Aβ_{1-42}$ immunized B6SJLF1 mice were subjected to Th1 stimulation. Supernatants from cultured cells were collected and analyzed by ELISA for cell specificity as described under General Materials and Experimental Methods in the Examples section which follows. FIGS. 5A-D—histograms depicting secretion of cytokines from T-cells. T-cells were cultured without antigen or stimulated with increasing concentrations of Aβ (0.1, 1 and 10 µg/ml) and secretion of cytokines was measured: FIG. 5A—IL2, measured after 24 hours in culture; FIG. 5B—IFN-γ, measured after 48 hours; FIG. 5C—IL-10, measured after 48 hours in culture; FIG. 5D—IL-17A, measured after 72 hours in culture. IL-4 secretion was measured after 24 hours in culture, however, no protein was detected (data not shown). FIG. 5E—a histogram depicting cell proliferation. $^{3-[H]}$-Thymidine incorporation assay (assessment of cell proliferation). Cells show a typical Th1 phenotype with secretion of primarily IL-2 and IFN-γ with little to no secretion of IL-4, IL-10 or IL-17A.

Figure 6B:
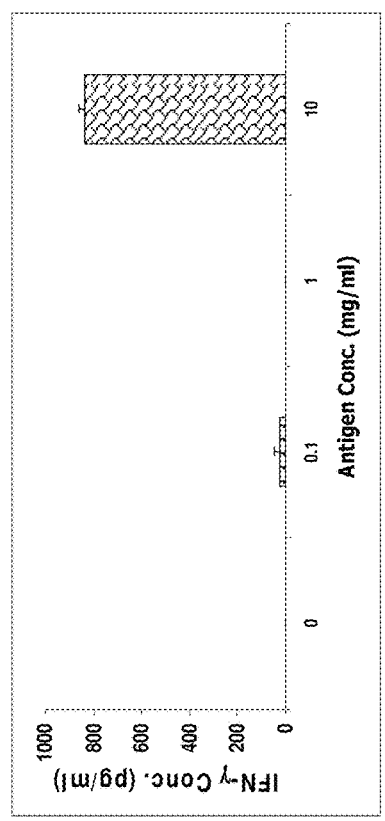
Figure 6A:
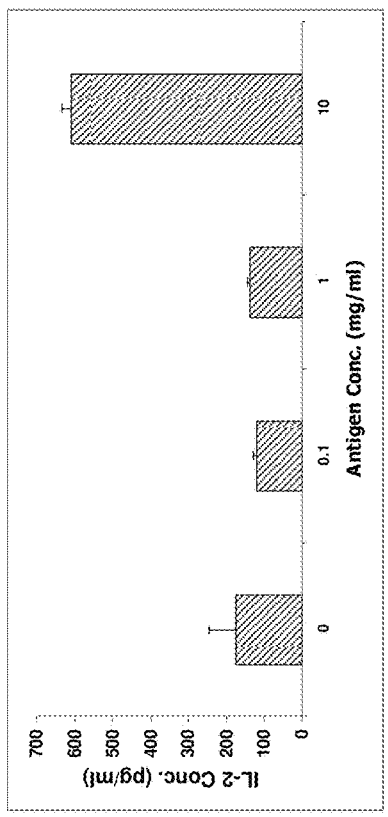
Figure 6D:
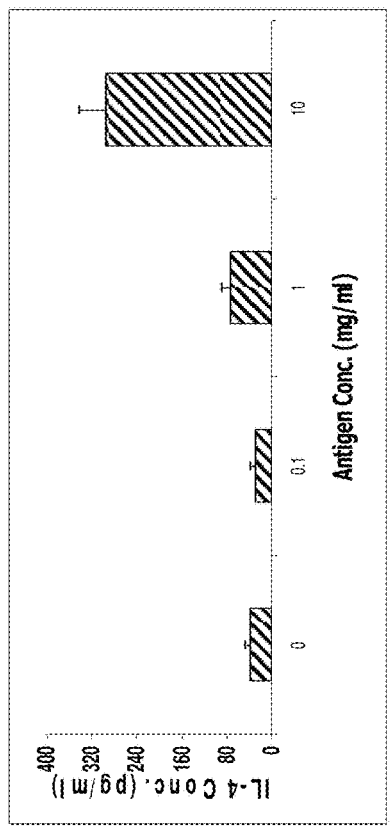
Figure 6C:
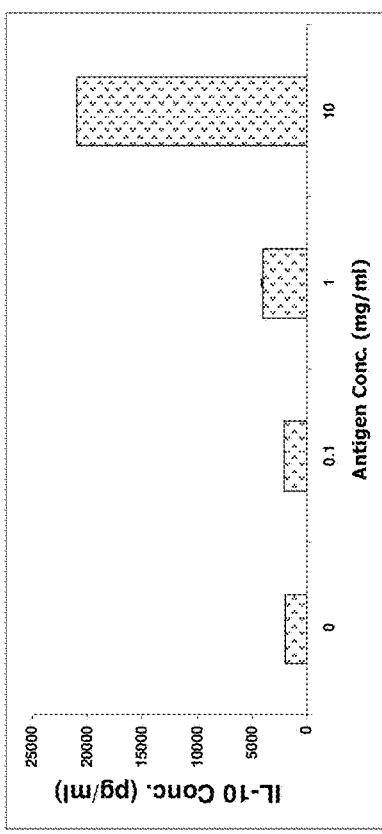
Figure 6E:
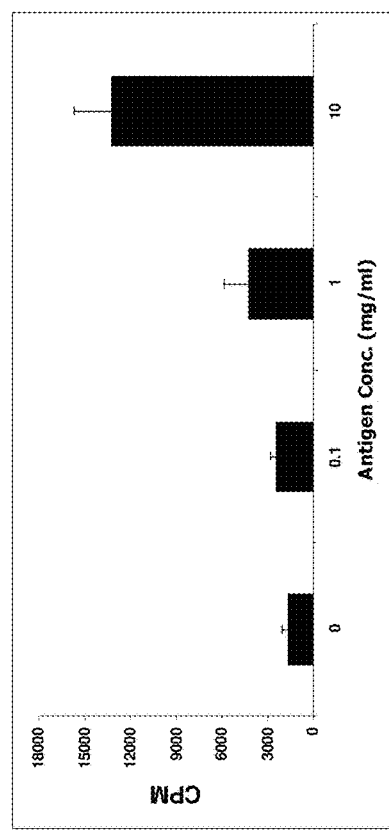

FIGS. 6A-E demonstrate generation of Aβ-specific Th2 T-cells. Cultured T-cells isolated from $Aβ_{1-42}$ immunized B6SJLF1 mice were subjected to Th2 stimulation. Supernatants from cultured cells were collected and analyzed by ELISA for cell specificity as described in General Materials and Experimental Methods. FIGS. 5A-D—histograms depicting secretion of cytokines from T-cells. T-cells were cultured without antigen or stimulated with increasing concentrations of Aβ (0.1, 1 and 10 μg/ml) and secretion of the following cytokines was measured: FIG. 6A—IL-2, measured after 24 hours in culture; FIG. 6B—IFN-γ, measured after 48 hours; FIG. 6C—IL-10, measured after 48 hours in culture; FIG. 6D—IL-4, measured after 24 in culture; IL-17A measured after 72 hours was not detected (data not shown). FIG. 6E—a histogram depicting cell proliferation. $^{3\text{-}[H]}$-Thymidine incorporation assay was conducted to asses cell proliferation. Cells show a typical Th2 phenotype with secretion of primarily IL-2, IL-4 and IL-10 with little to no secretion of IFN-γ or IL-17A.

Figure 7D:
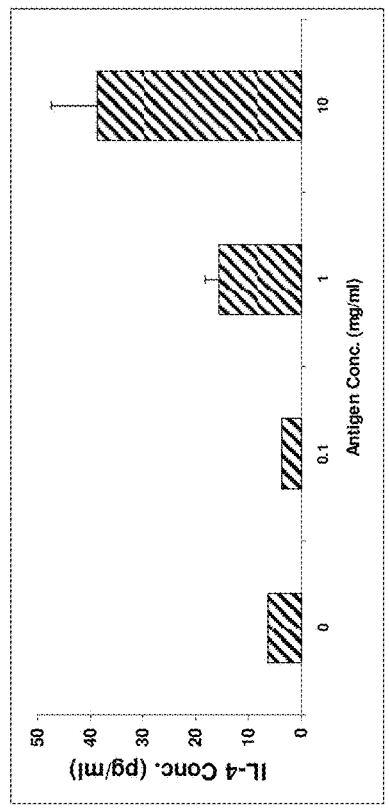
Figure 7C:
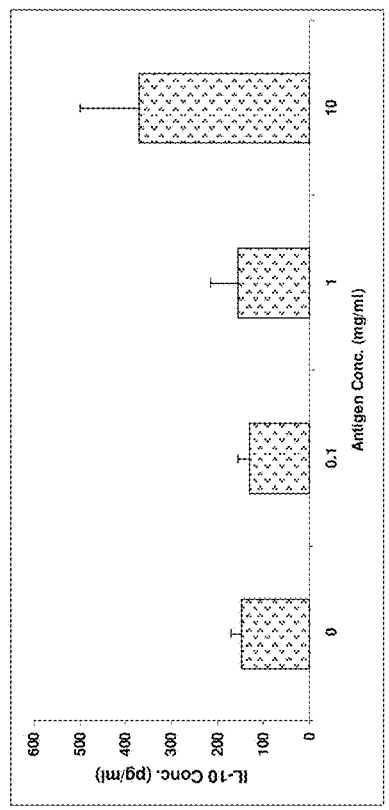

FIGS. 7A-F demonstrate generation of Aβ-specific Th17 T-cells. Cultured T-cells isolated from $Aβ_{1\text{-}42}$ immunized B6SJLF1 mice were subjected to Th17 stimulation. Supernatants from cultured cells were collected and analyzed by ELISA for cell specificity as described in General Material and Experimental Methods. FIGS. 7A-E—histograms depicting secretion of cytokines from T-cell. T-cells were cultured without antigen or stimulated with increasing concentrations of Aβ (0.1, 1 and 10 μg/ml) and secretion of the following cytokines was measured: FIG. 7A—IL-2, measured after 24 hours in culture; FIG. 7B—IFN-γ, measured after 48 hours in culture; FIG. 7C—IL-10, measured after 48 hours in culture; FIG. 7D—IL-4, measured after 24 hours in culture; FIG. 7E—IL-17A, measured after 72 hours. in culture. FIG. 7F—a histogram depicting cell proliferation. $^{3\text{-}[H]}$-Thymidine incorporation assay was conducted to asses cell proliferation status. Cells show a typical Th1/Th17 phenotype with secretion of primarily IL-2, IFN-γ and IL-17A with little to no secretion of IL-4 and IL-10.

FIGS. 8A-B are images of fluorescence microscopy demonstrating that injected Aβ-specific CD4 Th1 cells migrate within the brain parenchyma of APP Tg mice. APP Tg mice were ICV injected with 2.5×10$^5$ Aβ-specific CD4 Th1 cells. Immunohistochemistry (IHC) was carried out on brain sections of mice sacrificed 7 days post injection (7 dpi). Brain sections were stained with specific antibodies for T-cells (anti-CD4 antibody, labeled with green fluorescence) and microglia (anti IBA-1 antibody labeled with red fluorescence. Nuclei counter staining was performed using TOPRO-3. FIG. 8A-Low magnification of a brain section (size bar—200 μm). Note numerous CD4 T cells (green) in close association with resident microglia (IBA-1 in red). Nuclei are stained with TOPRO-3 (blue). FIG. 8B-High magnification of T-cells from a selected area (yellow box shown in FIG. 8A) in the hippocampus size bar—20 μm).

FIGS. 9A-G are images of fluorescence microscopy demonstrating migration and retention of CD4 Th1 Aβ-specific T-cells within the brain tissue of APP Tg mice during 28 days post injection. One-year-old APP Tg mice were ICV injected with Aβ-specific CD4 Th1 cells as described in FIGS. 2A-C above. Mice were sacrificed at 7 (FIGS. 9A-C), 14 (FIGS. 9D-E) and 28 (FIGS. 9F-G) days point injection and IHC was carried out to assess cell location and density. Brain sections were stained for CD4 (green) and counterstained with TOPRO-3 (blue) for cell nuclei. FIG. 9A—brain section, 4× magnification. Note CD4 T cells throughout the cortex (white arrows). FIG. 9B—brain section, 10× magnification. Note CD4 T cells in the hippocampus (white arrow); FIG. 9C—high magnification (100×, bar representing 20 μm) showing a group of CD4 T cells. FIG. 9D—brain section 4× magnification. Note CD4 T cells are still abundant in the cortex/hippocampus (white arrows) and in the meninges (red arrow); FIG. 9E—brain section, 10× magnification. Note CD4 T cells at the hippocampus area. FIG. 9F—brain section, 4× magnification. FIG. 9G—brain section, 10× magnification. Note that 28 days post injection most CD4 T cells have left the parenchyma of APP/PS1 Tg mice and are concentrated in the meninges. Size bars in FIGS. 9A, 9D and 9F—400 μm; Size bars in FIGS. 9B, 9E and 9G—200 μm; Size bar in FIG. 9C—20 μm.

FIGS. 10A-F are images of fluorescence microscopy demonstrating that ICV injected CD4 T cells are targeted to amyloid plaques in the brain of APP Tg mice. Tg mice were injected with Aβ-specific Th1 cells as described in FIGS. 2A-C above and were killed at 7 (FIGS. 10A, 10D, 10E and 10F), 14 (FIG. 10B) and 28 (FIG. 10C) days post injection. IHC on brain sections was carried out to view the localization pattern of CD4 T cells in relation to the amyloid beta plaques. FIG. 10A-C—immuno-staining with anti-CD4 antibody (labeled with green), anti-Aβ antibody (labeled with red) and counterstaining of cell nuclei with TOPRO-3 (blue). FIG. 10D—immuno-staining with anti CD4 antibody (green); FIG. 10E-immuno-staining with anti-Aβ antibody (red) and counterstaining with TOPRO-3 of the cell nuclei (blue); FIG. 10F—merged image of FIGS. 10D and 10E. Note that at all time points tested, CD4 T-cells (green) were seen co-localized with amyloid beta plaques (red) throughout the hippocampus and cortex areas (FIGS. 10A-C). High magnification of such co-localization is seen in brain sections of Tg mouse killed at 7 dpi (FIGS. 10D-F). CD4 T cells (green, FIG. 10D) surround the core of an amyloid plaque (red and nuclei in blue, FIG. 10E) and the merged image shows that CD4 T-cells (green) co-localizes with Aβ plaques (red). Size bars in FIGS. 10A-C—200 μm); Size bars in FIGS. 9D-F—20 μm.

Figures 11A, 11B, 11C:
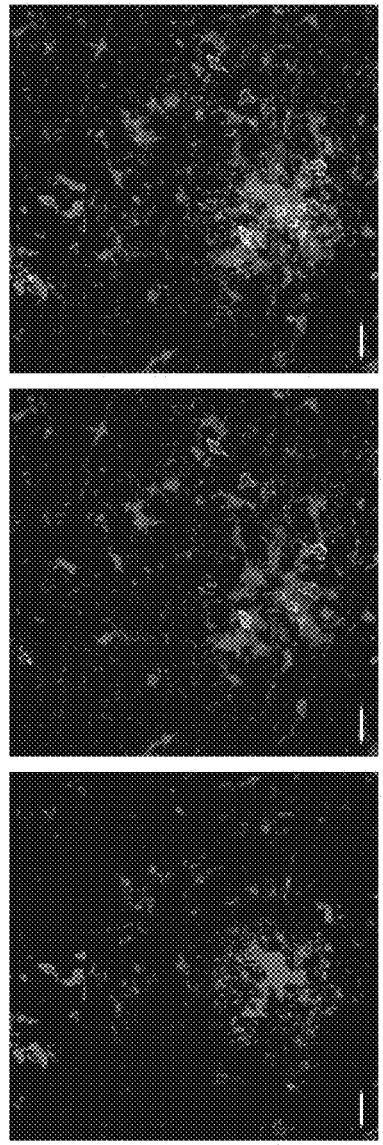

FIGS. 11A-C—are images of fluorescence microscopy demonstrating CD4 T-cell interactions with brain-resident microglia in APP Tg mice. Tg mice were injected with Aβ-specific Th1 cells as described in FIGS. 2A-C above. IHC was carried out on brain sections of mice killed 14 dpi in order to assess CD4-microglia interactions near the amyloid plaques. FIG. 11A—immuno-staining with anti-Aβ (red fluorescence, specific for Aβ plaques); FIG. 11B-immuno-staining with anti-CD4 (green fluorescence, specific for T cells) and anti-IBA-1 (blue fluorescence, specific for microglia); FIG. 11C—merged image of FIGS. 11A and 11B. Note the amyloid plaque (FIG. 11A, labeled in red), surrounded by microglia and CD4 T cells (FIG. 11B, blue and green, respectively) and the merged image (FIG. 11C). Size bars in FIGS. 11A-C—20 μm.

FIGS. 12A-C are images of fluorescence microscopy demonstrating that migration of Aβ-specific CD4 Th1 cells in the brain is independent of IFN-γ expression by brain-endogenous cells. Tg mice were injected with 2.5×10$^5$ Aβ-specific CD4 Th1 as described in FIGS. 2A-C and killed at different time points (7 dpi, FIGS. 12A-B; and 28 dpi, FIG. 12C) to asses cell location and density. Brain sections were stained for CD4 (green fluorescence) and counterstained with TOPRO-3 (blue fluorescence) for cell nuclei. Note that at 7 dpi CD4 T cells were observed throughout the cortex (FIG. 12A, white arrows), and throughout the hippocampus (FIG. 12B, white arrowheads). CD4 T cells remain in lower numbers in the brain at 28 dpi (FIG. 12C). Size bars in FIGS. 12A and C—400 μm; Size bar in FIG. 12B—200 μm.

Figure 13:
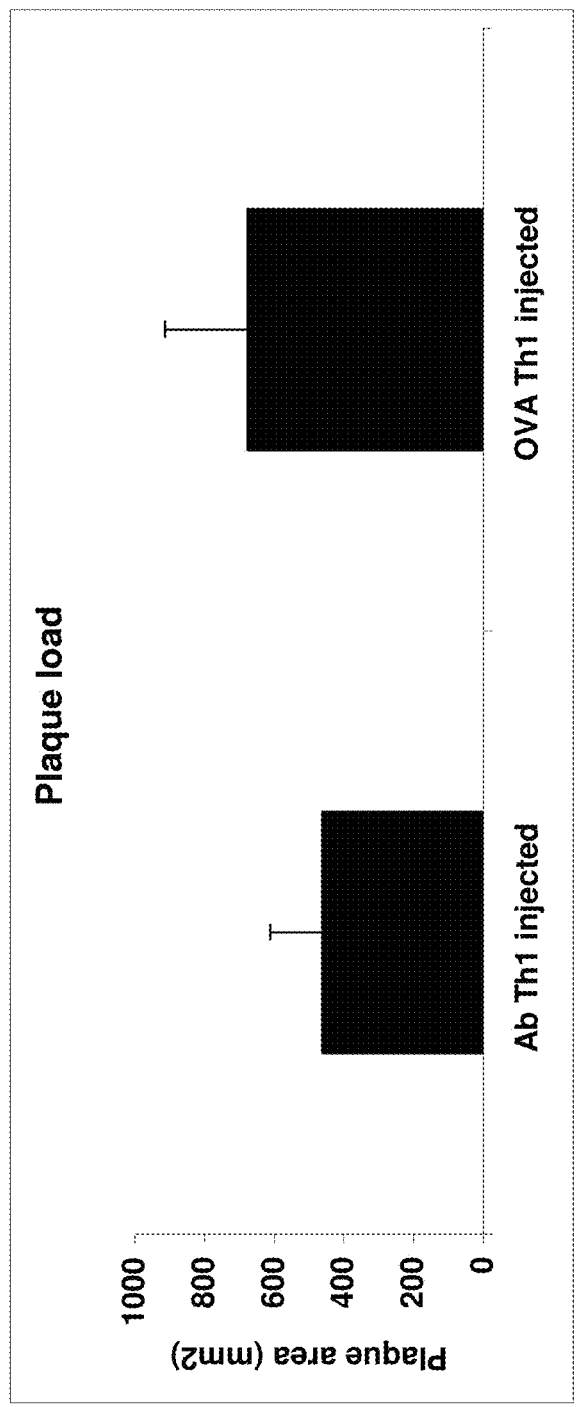

FIG. 13 is a histogram depicting the area of plaques in Aβ Th1 injected brains or OVA Th1 injected brains. APP Tg mice were injected ICV with either 2.5×10$^5$ Aβ-specific or OVA-specific CD4 Th1 cells as described in FIGS. 2A-C above. Animals were killed 28 days after injection and IHC was carried for Aβ plaques. At least 4 sections per brain were stained and amyloid load was quantified using the Volocity image analysis software as described in General Materials and Experimental Methods. Note the significant reduction in plaque area in brains of mice treated by Aβ specific Th1, demonstrating that Aβ-specific Th1 cells reduce amyloid burden in the brains of AD mouse model.

Figure 14A:
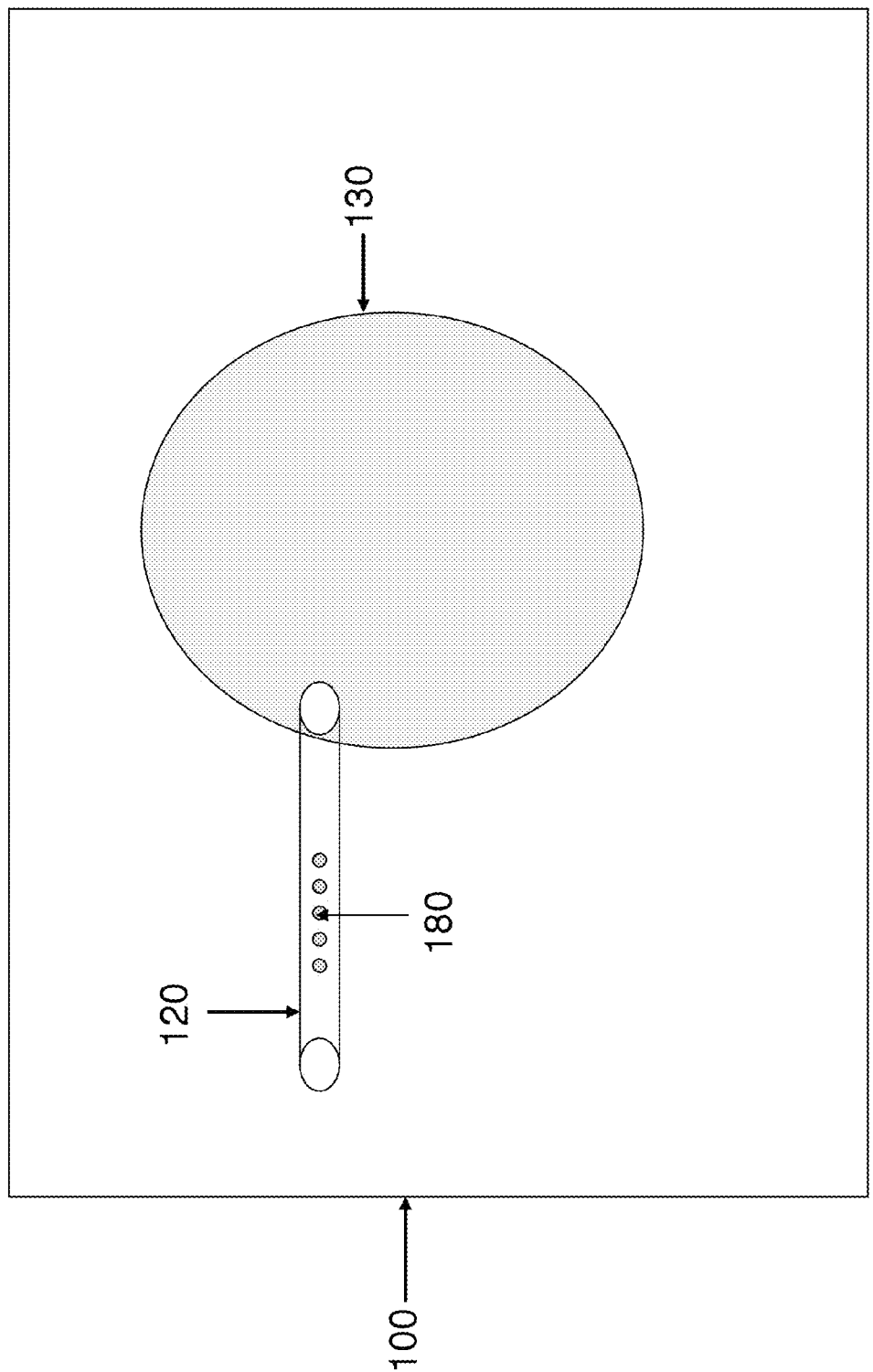

FIG. 14A depicts a device according to some embodiments of the invention. Device 100 comprises catheter 120 for delivery of T cells 180 (blue filled circles) into brain 130 of a subject.

FIG. 14B depicts a device according to some embodiments of the invention. Device 400 comprises catheter 120 for delivery of T cells 180 (blue filled circles) intrathechally to cerebrospinal fluid 190 of a subject. According to some embodiments of the invention, cerebrospinal fluid 190 and is accessed via an injection or infusion into the spinal canal near the subject's waist.

Figure 15:
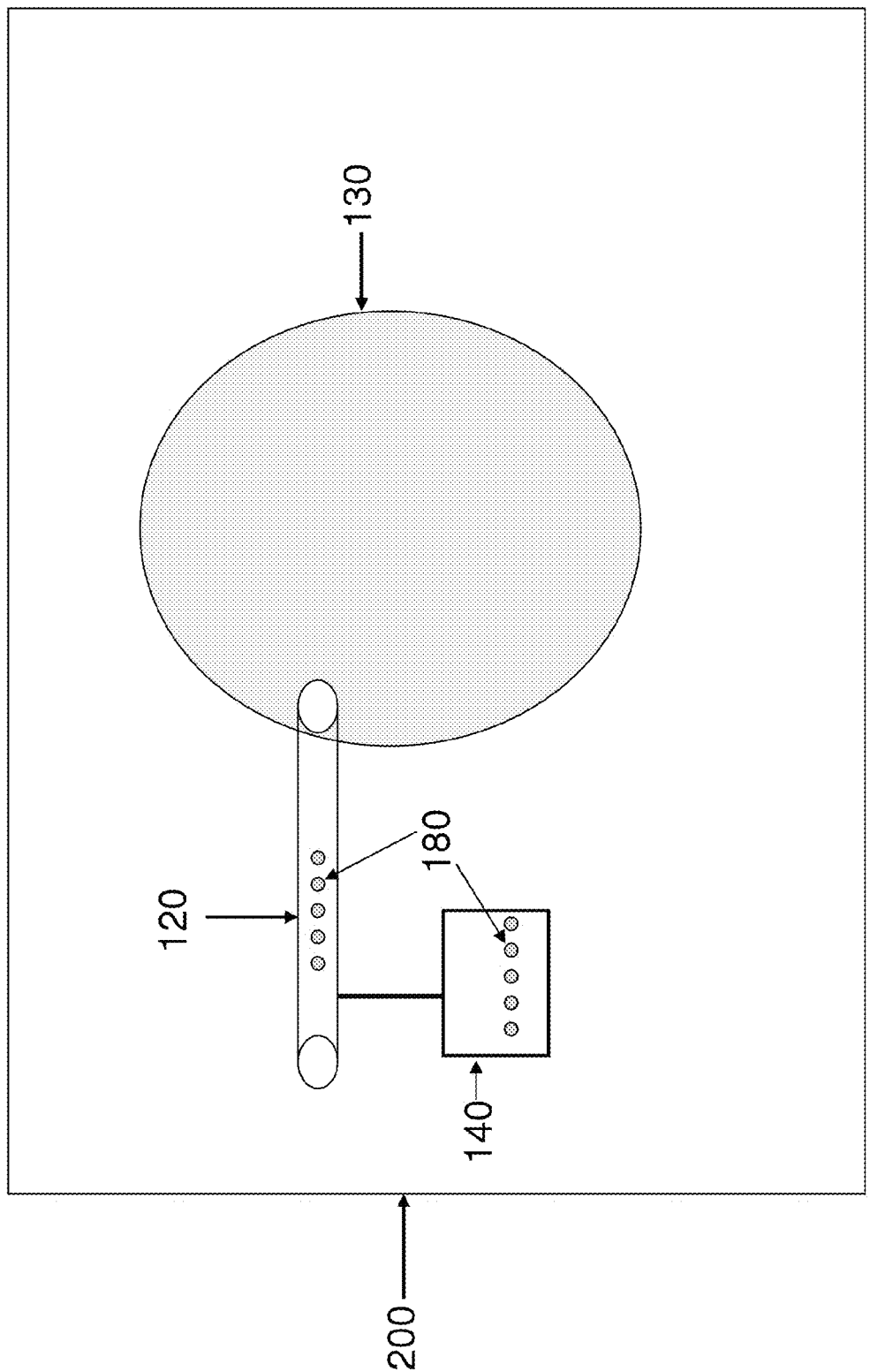

FIG. 15 depicts a device according to some embodiments of the invention. Device 200 comprises catheter 120 for delivery of T cells 180 into brain 130 of a subject and reservoir 140 which comprises the T cells 180 (blue filled circles).

Figure 16:
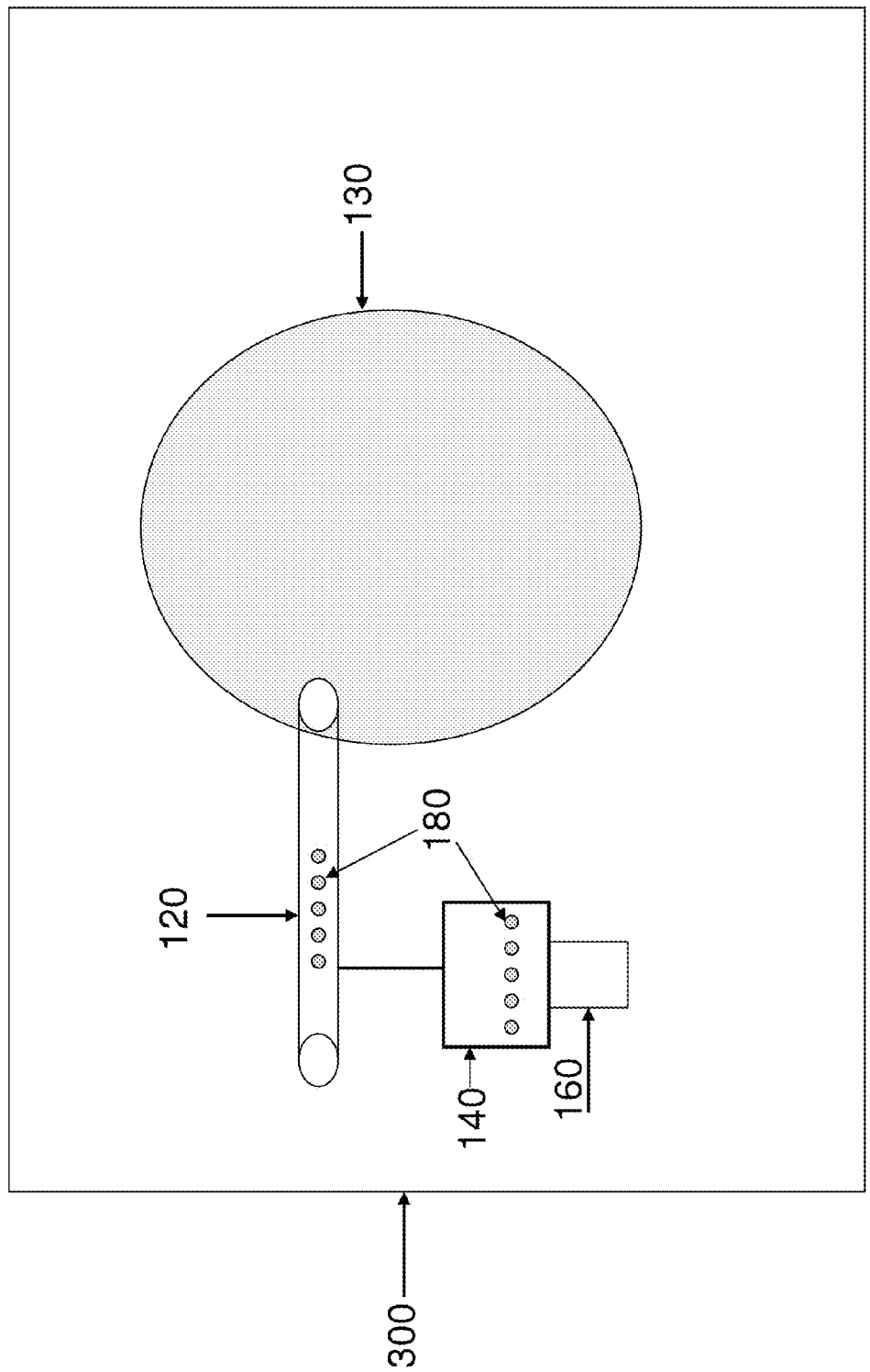

FIG. 16 depicts a device according to some embodiments of the invention. Device 300 comprises catheter 120 for delivery of T cells 180 into brain 130 of a subject, reservoir 140 which comprises the T cells of some embodiments of the invention and pump 160 for releasing T cells 180 (blue filled circles) from reservoir 140 into brain 130 of the subject.

FIGS. 17A-E are histograms depicting IL-2, IL-4, IFN-γ, IL-10 and IL-17A secretion demonstrating in vitro differentiation of primary splenocytes to Th1 and Th2 phenotypes. Splenocytes were isolated in order to differentiate the naïve $T_H$ population into $T_H1$ or $T_H2$ subtypes following polyclonal stimulation by anti CD3 antibody. The splenocytes were seeded ($2.5 \times 10^6$) in tissue culture wells coated with 0.5 µg/ml anti-CD3 antibody for one week. Differentiation of the cells into $T_H1$ or $T_H2$ was induced by addition of 20 ng/ml IL-12 and 20 µg/ml anti-IL-4 antibody or 4 ng/ml IL-4 and 20 µg/ml anti-IL-12 antibody, respectively, to the culture medium for two days. After one week the cells were collected and seeded in tissue culture wells coated with 0.1 µg/ml anti-CD3 antibody. Supernatants were collected after 24, 48 and 72 hours for analysis of IL-2, IL-4, IFN-γ, IL-10 and IL-17A secretion by sandwich ELISA. Note that undifferentiated and differentiated cells express IL-2. $T_H1$ cells express high levels of IFN-γ and very low levels of IL-10 and IL-17A, while $T_H2$ cells express high levels of the $T_H1$ cytokine, IFN-γ, and the $T_H2$ cytokines IL-10 and IL-4 and very low levels of IL-17A.

Figure 18B:
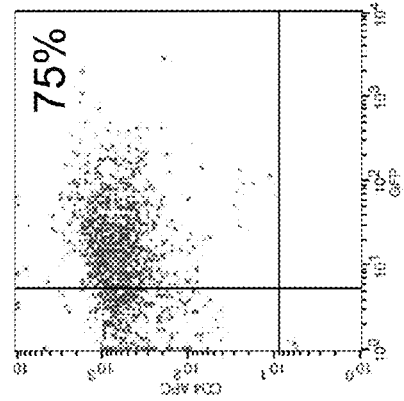
Figure 18D:
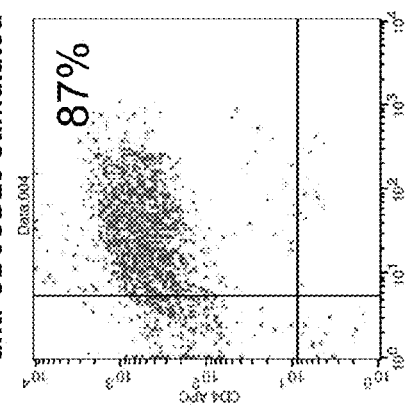
Figure 18A:
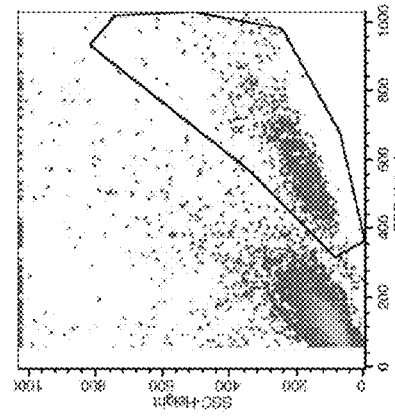
Figure 18C:
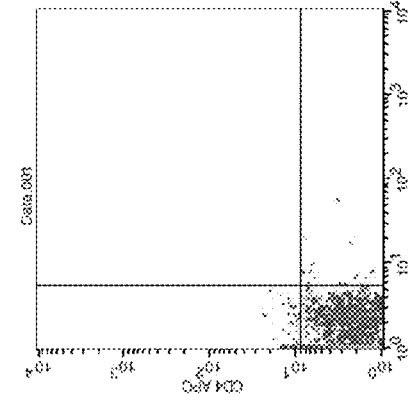

FIGS. 18A-D are FACS analyses depicting infection efficiency of T cells with lentivirus. T cells were stimulated with anti-CD3 (FIG. 18B) or anti-CD3/CD28 (FIG. 18D) and were then infected with lentivirus (FIGS. 18B and 18D) or remained uninfected (FIG. 18C). FIG. 18A—side scatter (SSC) and forward scatter (FSC) dot plot analysis; FIG. 18B-D—Allophycocyanin (APC)-labeled CD4 (Y-axis) and GFP-labeled (X-axis). Cells at the upper right quadrant are CD4 T cells infected with lentivirus. Note the infection efficiency of 75% and 87% for anti-CD3 and anti-CD3/CD28 beads, respectively.

FIGS. 19A-B are microscopic images depicting T cells infected by lentivirus which express GFP/BDNF. FIG. 19A—fluorescent image showing GFP expression by green fluorescence; FIG. 19B—phase contrast of the same cells (same microscopic field) showing the contour of the T cells.

Figure 20:
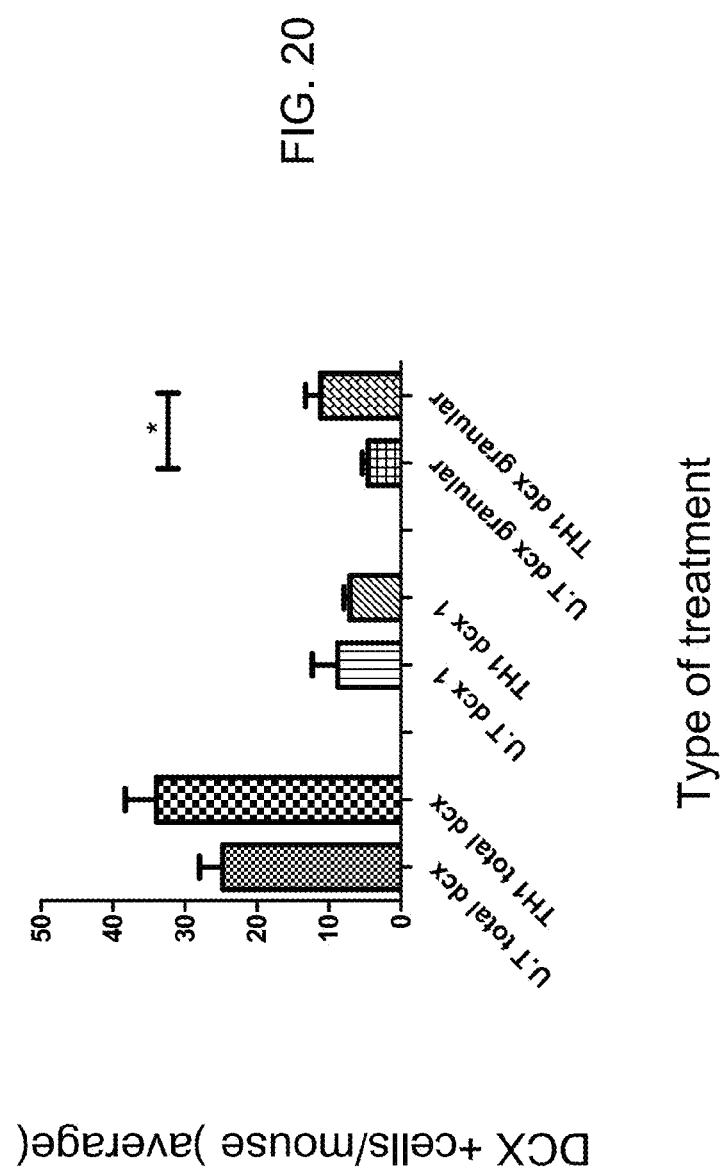

FIG. 20 is a histogram depicting the effect of ICV injection of activated T cells on hippocampal neurogenesis. Graph bars represent means of cell number per mouse in each group (n=3-4)±SEM. P values were calculated using the Student's t-test (*–p<0.05, **–p<0.005). Note that neurogenesis measured by total DCX-positive cells in the DG, as well as neuroblasts in the granular area of the DG, which includes differentiating neuroblasts, is enhanced following injection of Th1 cells.

Figure 21:
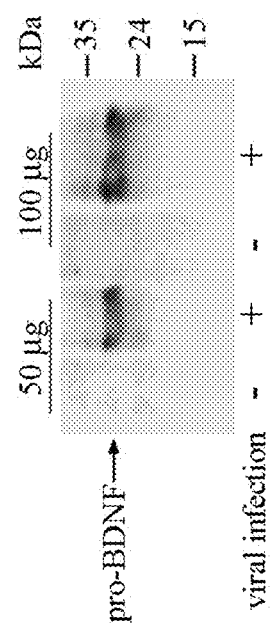

FIG. 21 is an image depicting Western blot analysis of pro-BDNF in 293T cells. 293T cells were infected with lenti virus encoding pro-BDNF, and protein extracted from the cells was subject to immunoblot analysis using an anti-BDNF antibody. Note the induction of pro-BDNF expression in 293T cells infected with lenti virus encoding pro-BDNF.

DESCRIPTION OF SPECIFIC EMBODIMENTS OF THE INVENTION

The present invention, in some embodiments thereof, relates to methods and devices for treating conditions associated with neural damage such as neurodegenerative diseases using activated T-cells such as non-antigen specific polyclonal activated T-cells, non-nervous system antigen-activated T-cells and/or genetically modified T-cell, and, more particularly, but not exclusively, to intracranial, intracerebroventricular and/or intrathecal administration of the activated and/or genetically modified T-cells for delivery of a polypeptide-of-interest and/or treatment of conditions associated with neuronal damage such as neurodegenerative diseases.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

The present inventor has uncovered that administration of T-cells into the CNS can be beneficial to patients suffering from slowly progressing neurological disorders; that activated CD4 T-cell can migrate and reside in the brain for a limited amount of time; and that once these cells enter the brain they are targeted to the site of lesion and assist in the removal of Aβ plaques; and that these cells leave the CNS with no impairment of any cognitive function.

Thus, as shown in the Examples section which follows, while intra-brain administration of naïve CD4 T cells results in no penetration into the parenchymal tissue of the brain (Examples 1, FIGS. 1A-D), following stimulation of the T cells, by either a polyclonal non-specific stimulation (e.g., using αCD3 and αCD28 antibodies; Example 2, FIGS. 2A-C; FIGS. 4A-E) or a specific stimulation (e.g., OVA-specific; Example 2, FIGS. 3A-E) the T cells migrate through the parenchymal tissue of the brain in a manner which is dependent on interferon-gamma secretion by the T cells. In addition, as shown in Example 5 of the Examples section which follows, migration of T-cells in the brain does not require endogenous pre-expression of interferon-gamma in the brain (Example 5, FIGS. 12A-C). The T-cells can be manipulated to secrete specific polypeptides such as cytokines and drugs by directed ex-vivo stimulation (Example 3, FIGS. 5A-E, 6A-E and 7A-F). The stimulated T cells can migrate within the brain and secrete a polypeptide-of-interest to target locations and cells, and to associate with amyloid plaques and microglia (Example 6, FIGS. 10A-F, FIGS. 11A-C). Thus, the intra-brain administration of Aβ-specific Th1 T-cells resulted in a significant plaque clearance in brain of Alzheimer's disease mice, demonstrating the therapeutic application of intra-brain administration of T-cells. Moreover, as shown in Example 4 of the Examples section which follows, following 28 days from injection the T cells are cleared from the brain (Example 4, FIGS. 6A-E, 8A-B, 9A-G), thus preventing any prolong adverse immune response. The present inventor has demonstrated the in vitro polarization of primary splenocytes into Th1 and Th2 phenotypes by a combination of IL-12 and anti-IL-4 antibody (for induction of polarization into $T_H1$ cells) or a combination of IL-4 and anti-IL-12 antibody (for induction of polarization into $T_H2$ cells) (Example 8, FIGS. 17A-E). In addition, the present inventor has demonstrated the feasibility of genetically modifying T-cells by Lentiviral infection in order to express a neurotrophic marker such as BDNF (Example 9, FIGS. 18A-D and 19A-B), and showed that administration of such cells into the brain results in increased neurogenesis in the dentate gyrus (DG) and in particular, in the granular area of the DG (FIG. 20, Example 10). Altogether, these results demonstrate that intrabrain administration of activated T-cells can be used for the treatment of pathologies associated with neural damage, neurological conditions associated with damage of neuronal cells such as neurodegenerative diseases and acute brain injury by activating the T-cells to secrete interferon or genetically modify them to secrete any therapeutic polypeptides or factors which induce expression of therapeutic factors into the brain while preventing peripheral and meninginal side effects.

Thus, according to an aspect of some embodiments of the invention, there is provided a method of treating a pathology associated with neural damage. The method is effected by administering a non-antigen specific polyclonal activated T cell into the brain in a manner which prevents meningoencephalitis in the subject, thereby treating the pathology associated with neural damage.

The term "treating" refers to inhibiting, preventing or arresting the development of a pathology (disease, disorder or condition) and/or causing the reduction, remission, or regression of a pathology. Those of skill in the art will understand that various methodologies and assays can be used to assess the development of a pathology, and similarly, various methodologies and assays may be used to assess the reduction, remission or regression of a pathology.

As used herein, the term "subject" includes mammals, preferably human beings at any age which suffer from the pathology. Preferably, this term encompasses individuals who are at risk to develop the pathology.

As used herein the phrase "pathology associated with neural damage" refers to any disease, disorder or condition which is characterized by an acute and/or progressive damage and/or loss of neuronal cells and/or glial cells.

According to some embodiments of the invention, the pathology associated with neural damage affects neuronal and/or glial cells in the central nervous system.

Non-limiting examples of pathologies caused by an acute or sudden damage to neural cells include brain injury, spinal injury, head injury, and stroke [cerebrovascular accident (CVA)].

According to some embodiments of the invention, the pathology associated with neural damage is cancer. Non-limiting examples of cancers which affect the neuronal and glial cells include glioblastoma, neuroblastoma, adenocarcinoma of the brain, as well as metastases of a distant cancers such as breast cancer, lung cancer, and the like.

According to some embodiments of the invention, the pathology associated with neural damage is chronic.

According to some embodiments of the invention, the pathology associated with neural damage is a neurodegenerative disease.

Non-limiting examples of neurodegenerative diseases which can be treated according to the present teachings include multiple sclerosis, Lupus eruthromatosis, Alzheimer's disease, Parkinson's Disease, senile dementia, amyotrophic lateral sclerosis, Down's Syndrome, Dutch Type Hereditary Cerebral Hemorrhage Amyloidosis, Reactive Amyloidosis, Familial Mediterranean Fever, Familial Amyloid Nephropathy with Urticaria and Deafness, Muckle-Wells Syndrome, Idiopathic Myeloma, Macroglobulinemia-Associated Myeloma, Familial Amyloid Polyneuropathy, Familial Amyloid Cardiomyopathy, Isolated Cardiac Amyloid, Systemic Senile Amyloidosis, Adult Onset Diabetes, Insulinoma, Isolated Atrial Amyloid, Medullary Carcinoma of the Thyroid, Familial Amyloidosis, Hereditary Cerebral Hemorrhage with Amyloidosis, Familial Amyloidotic Polyneuropathy, Scrapie, Creutzfeldt-Jacob Disease, Gerstmann Straussler-Scheinker Syndrome, Bovine Spongiform Encephalitis, a Prion-mediated disease, and Huntington's Disease.

According to some embodiments of the invention, the neurodegenerative disease is associated with formation of an amyloid fibril.

As used herein, the phrase "amyloid fibril" refers to the intra- or extracellular tissue deposits, in one or more tissue or organs, of fibril protein material which is generically termed amyloid. Amyloid fibrils are formed by conformation changes which lead to misfolding of the amyloid precursor protein, such as a conformation conversion from an α-helix configuration to a β-pleated sheet structure. Thus, amyloid fibrils initiate from an innoculum of misfolded proteins which further facilitates fibril formation around it (Reviewed in Lachmann H J and Hawkins P N, 2003. Nephron Clin. Pract. 94: c85-8).

Non-limiting examples of protein precursors which can result in amyloid fibrils include, Amyloid beta protein, Transthyretin, Procalcitonin, IAPP (Amylin), amyloid light chain (AL), non-immunoglobulin amyloid associated (AA), non-immunoglobulin amyloid associated serum precursor (SAA), α-synucleic protein, ataxin and huntingtin.

T-cells are lymphocyte cells which play a central role in cell-mediated immunity and which are distinguished from other lymphocyte types, such as B cells and natural killer cells (NK cells) by the presence of a T cell receptor (TCR).

As used herein the phrase "T-cell" refers to a non-cytotoxic T lymphocyte cell.

According to some embodiments of the invention the T-cell is a CD4+ T-cell or a non-cytotoxic CD8+ T cell. The T cells can be of effector and/or regulatory phenotype.

The T-cells used by specific embodiments of the invention can be primary T-cells or a T-cell line.

The T-cells can be obtained from a biological sample of a subject such as a blood sample, a spleen sample and a lymph node sample. T-cells can be isolated and purified according to methods known in the art [e.g., as described in Mor and Cohen, 1995, J. Immunol. 155:3693-3699; Monsonego, A., V. Zota, A. Karni, J. I. Krieger, A. Bar-Or, G. Bitan, A. E. Budson, R. Sperling, D. J. Selkoe, and H. L. Weiner. 2003. Increased T cell reactivity to amyloid beta protein in older humans and patients with Alzheimer disease. J Clin Invest 112:415-422; each of which if fully incorporated herein by reference].

As used herein the term "isolated" refers to at least partially separated from the natural environment e.g., the human body.

The T-cells can be syngeneic (or syngenic) T cells (i.e., genetically identical, or sufficiently identical and immunologically compatible T cells so as to allow for transplantation; e.g., self T cells derived from the subject in which the T-cells are administered; or from an identical twin having a compatible immunological pattern) or non-syngeneic e.g., semi-allogeneic or semi-autologous T-cells derived from related or partially matched donors (i.e., donors that share at least some of the HLA alleles of the treated subject), e.g. siblings, parents, children, or HLA-matched or partially matched subjects; or fully allogeneic T cells which are derived from non-related donors. The activated T cells are characterized by CD4 and/or CD8 phenotypes.

According to some embodiments of the invention, the activated T-cells are non-attenuated, although attenuated activated T-cells may be used. T-cells may be attenuated using methods well known in the art, including but not limited to, by gamma-irradiation, e.g. 1.5-10.0 Rads [e.g., as described in Ben-Nun, A., Wekerle, H. and Cohen, I. R., Nature 292:60-61 (1981); Ben-Nun, A. and Cohen, I. R., J. Immunol. 129:303-308 (1982), each of which is fully incorporated herein by reference in its entirety]; and/or by pressure treatment, for example as described in U.S. Pat. No. 4,996,194 (Cohen et al., which is fully incorporated herein by reference in its entirety); and/or by chemical cross-linking with an agent such as formaldehyde, glutaraldehyde and the like, for example as described in U.S. Pat. No. 4,996,194 (Cohen et al.); and/or by cross-linking and photoactivation with light with a photoactivatable psoralen compound, for example as described in U.S. Pat. No. 5,114,721 (Cohen et al., which is fully incorporated herein by reference in its entirety); and/or by a cytoskeletal disrupting agent such as cytochalsin and colchicine, for example as described in U.S. Pat. No. 4,996,194 (Cohen et al.).

As used herein the phrase "non-antigen specific polyclonal activated T-cells" refers to a pool of T cells isolated from a subject and stimulated in the absence of antigen.

According to some embodiments of the invention, the T cell is activated ex-vivo.

According to some embodiments of the invention, the non-antigen specific polyclonal activated T-cells are obtained by exposure of T-cells to various molecules such as protein(s) (e.g., various antibodies, cytokines, chemokines), Toll-like receptor (TLR) ligand(s), lectin(s) [e.g., concavalin A, phytohaemagglutinin] and ionomycin, which bind and activate the T-cell receptor. Methods of generating non-antigen specific polyclonal activated T-cells are known in the art and are described for example, in Curtsinger J M, Mescher M F. 2010. "Inflammatory cytokines as a third signal for T cell activation". Curr. Opin. Immunol. 22(3): 333-40. Epub 2010 Apr. 2; Moretta A., et al. "Surface molecules involved in the activation and regulation of T or natural killer lymphocytes in humans". Immunol Rev. 1989. 111: 145-75; Sleasman J W., et al. 1991. "Con A-induced suppressor cell function depends on the activation of the CD4+CD45RA inducer T cell subpopulation". Cell Immunol. 133: 367-78; Chin C S., et al. 2004. "Bryostatin 1/ionomycin (B/I) ex vivo stimulation preferentially activates L selectin low tumor-sensitized lymphocytes". Int. Immunol. 16: 1283-94; each of which is fully incorporated herein by reference in its entirety.

According to some embodiments of the invention, activation of the non-antigen specific polyclonal T cell is performed by incubation of a T cell with an anti CD3 antibody, an anti CD28 antibody, phytohaemagglutinin (PHA), and/or Concavalin A, and/or any combination thereof.

For example, activation of T-cells can be achieved by interacting the T cells with a combination of anti-CD3 and anti-CD28 antibodies the T cells, which stimulate both the primary and co-stimulatory signals that are required for activation and expansion of T cells.

The antibody can be attached to a surface such as beads, e.g., magnetic beads (e.g., Dynabeads® coupled to the antibodies, available from Invitrogen, Carlsbad, Calif., USA).

Following is a non-limiting description of non-antigen specific polyclonal activation of T-cells. Purified T cells (e.g., $1$-$1.5 \times 10^6$ cells) are placed in a tissue culture vessel (e.g., a 24-well tissue culture plate) in the presence of a medium and beads which are attached to the anti-CD28 and anti-CD3 antibodies. For example, the T-cells can be incubated in the Biotarget culture medium (Catalogue number 05-080-1, Biological Industries, Beit-Haemek, Israel) supplemented with 1% Pen/Strep/Nystatin, 40 mM L-glutamine. Dynabeads® Human T-Activator CD3/CD28 for cell expansion and activation (Invitrogen, Carlsbad, Calif., USA; Cat. No. 111-31D) are added to the culture medium at a bead-to-cell ratio of 1:1 followed by the addition of 30 U/ml recombinant interleukin-2 (rIL-2). The T cells are then incubated in a humidified $CO_2$ incubator at 37° C., and can be examined daily, noting cell size and shape. Cell shrinking and reduced proliferation rate is typically observed in exhausted cell cultures. When the cell density exceeds $2.5 \times 10^6$ cells/ml or when the medium turns yellow the cultures are split to a density of $0.5$-$1 \times 10^6$ cells/ml in Biotarget culture medium containing 30 U/ml rIL-2. Typically activation of the T-cells occurs within 2 days in the described culture conditions. Activated T cells can be then injected into a brain of a subject in need thereof.

According to some embodiments of the invention, the T cells are activated to express a protein-of-interest (e.g., a factor such as a neurotrophic factor, a cytokine, a chemokine and the like).

According to some embodiments of the invention, the activated T cells are stimulated to express a protein-of-interest without the need of further genetic modification of the T-cells.

Methods of controlling the secretion of the factor-of-interest from an activated T cell are known in the art and described, for example, in FIGS. 5A-E, 6A-E and 7A-F, and Example 3 of the Examples section which follows and in Fitch F W, et al., 2007, Curr. Protoc. Immunol. Chapter 6: Unit 6.25, "Measurement of interleukin-17"; and in Pappu B P, et al., 2006. Protoc. Immunol. Chapter 3: Unit 3.13, "Production of TH1 and TH2 cell lines and clones", each of which is fully incorporated herein by reference in its entirety. Briefly, specific T-cells can be generated using T-cells removed from a given individual followed by several rounds of ex-vivo stimulation using an endogenous antigen. The ex-vivo stimulation can result in generation of well characterized T-cell sub-populations, such as Th1, Th2, Th17, CD4+CD25+FOXP3+ regulatory T cells or Tr1 regulatory T cells. Using a cocktail of antibodies and recombinant cytokines, it is possible to generate antigen-specific Th1, Th2 and Th17 T-cell lines for further usage in injection experiments. A T-cell line secreting a mixed profile of Th1 or Th2 for example can also be generated.

According to some embodiments of the invention, the activated T-cell secretes a cytokine capable of immuno-regulation or immuno-modulation. Non-limiting examples of cytokines include interferon-gamma, interleukin-4, interleukin 10, interleukin-2, transforming growth factor beta (TGFβ), leukemia inhibitory factor (LIF) and GM-CSF (colony stimulating factor 2 (granulocyte-macrophage).

According to some embodiments of the invention, the activated T-cell expresses interferon-gamma.

As shown in the Examples section which follows, the present inventors have uncovered that expression of interferon gamma (e.g., secretion) by the T cells enables migration of the T cells within the brain from the site of administration to the target site, e.g., via the brain parenchyma. Thus, expression of interferon-γ by the T-cells not only has a therapeutic effect but also has an advantageous effect on the mobility of the T-cells within the brain parenchyma.

In addition, the interferon-gamma which is secreted by the T-cell can activate microglia.

According to some embodiments of the invention, the activated T-cell does not secrete interleukin 17 (IL-17) or interleukin 12 (IL-12).

According to some embodiments of the invention, the activated T-cell secretes a neurotrophic and/or a neuroprotective factor. Non-limiting examples of neurotrophic and/or a neuroprotective factor brain-derived neurotrophic factor (BDNF), insulin-like growth factor 1, Neurotrophic Factor, basic fibroblast growth factor, and Ciliary neurotrophic factor.

According to some embodiments of the invention, the activated T-cell secretes a chemokine, capable of stimulating migration of monocytes into the brain. Non-limiting examples of chemokines include MCP-1, RANTES, IP-10, and fractalkine.

According to some embodiments of the invention, the activated T-cells are genetically modified.

According to some embodiments of the invention, the activated T-cells and/or the genetically modified T-cells are purified i.e., make up about 95% or 100% of the administered cells.

According to an aspect of some embodiments of the invention, there is provided an isolated population of cells comprising at least about 70%, at least about 80%, at least about 85%, at least about 90%, at least about 91%, at least about 92%, at least about 93%, at least about 94%, at least about 95%, at least about 96%, at least about 97%, at least about 98%, at least about 99%, e.g., 100% of activated T-cells (either by non-antigen specific activation or by antigen specific activation) and/or genetically modified T-cells.

As used herein the term "isolated" refers to at least partially separated (e.g., removed) from the natural environment e.g., the population of cells present in the body (e.g., human body).

As used herein the phrase "genetically modified" refers to being transformed to exogenously express a polynucleotide-of-interest and optionally a polypeptide-of-interest. The polynucleotide may be included in a nucleic acid construct under the regulation of a promoter.

Methods of genetically modifying cells to express a polynucleotide-of-interest are well known in the art [e.g., Linker et al Brain 2010: 133; 2248-2263, "Functional role of brain-derived neurotrophic factor in neuroprotective autoimmunity: therapeutic implications in a model of multiple sclerosis"; which is fully incorporated herein by reference in its entirety] and are further described hereinunder.

According to some embodiments of the invention, the genetically modified activated T cell is capable of expressing a protein-of-interest. For example, the polynucleotide-of-interest can encode the polypeptide-of-interest. It should be noted that genetic modification of the T-cell can result in a constitutive or inductive expression of a polypeptide-of-interest.

According to some embodiments of the invention, the T cells constitutively express the protein-of-interest.

The protein-of-interest may be a secreted factor or an intracellular protein such as a transcription factor which induces expression of a secreted factor (e.g., an endogenous cytokine) by the T cell.

According to some embodiments of the invention, the protein-of-interest is secreted by the T cell.

According to some embodiments of the invention, the polypeptide-of-interest is a cytokine capable of immuno-regulation or immuno-modulation. Examples include, but are not limited to interferon gamma [IFNG; GenBank Accession NOs. NM_000619.2 (SEQ ID NO:1) and NP_000610.2 (SEQ ID NO:2)], interleukin-4 [IL4; interleukin-4 isoform 1 precursor GenBank Accession NOs. NM_000589.2 (SEQ ID NO:3) and NP_000580.1 (SEQ ID NO:4); interleukin-4 isoform 2 precursor GenBank Accession Nos. NM_172348.1 (SEQ ID NO:5) and NP_758858.1 (SEQ ID NO:6)], interleukin 10 [IL10; GenBank Accession Nos. NM_000572.2 (SEQ ID NO:7) and NP_000563.1 (SEQ ID NO:8)], IL-2 [interleukin 2, also known as TCGF; lymphokine; GenBank Accession Nos. NM_000586.3 (SEQ ID NO:9) and NP_000577.2 (SEQ ID NO:10)], TGFβ [e.g., transforming growth factor beta 1, also known as AP; DPD1; TGFB; GenBank Accession Nos. NM_000660.4 (SEQ ID NO:119) and NP_000651.3 (SEQ ID NO:11)], leukemia inhibitory factor [LIF, also known as cholinergic differentiation factor (CDF), DIA; HILDA; GenBank Accession Nos. NM_002309.3 (SEQ ID NO:12) and NP_002300.1 (SEQ ID NO:13)], and GMCSF [colony stimulating factor 2 (granulocyte-macrophage), also known as CSF2, MGC131935; MGC138897; GenBank Accession Nos. NM_000758.2 (SEQ ID NO:14) and NP_000749.2 (SEQ ID NO:15)].

According to some embodiments of the invention, the polypeptide-of-interest is a neurotrophic and/or a neuroprotective factor. Examples include, but are not limited to a neurotrophic Factor (NTF) such as nerve growth factor [NGF beta polypeptide; also known as NGFB, HSAN5, Beta-NGF, MGC161426, MGC161428; GenBank Accession Nos. NM_002506.2 (SEQ ID NO:121) and NP_002497 (SEQ ID NO:122)], neurotrophin-3 [NTF3; also known as HDNF, NGF2, NGF-2, MGC129711, NTF3; GenBank Accession NOs. NM_001102654.1 (SEQ ID NO:123) and NP_001096124.1 (SEQ ID NO:124); NM_002527.4 (SEQ ID NO:125) and NP_002518.1 (SEQ ID NO:126)], neurotrophin-4 [NTF-4; also known as NT4, NT5, NTF5, GLC10, GLC10, NT-4/5; GenBank Accession NOs. NM_006179.4 (SEQ ID NO:127) and NP_006170.1 (SEQ ID NO:128)], and brain-derived neurotrophic factor (BDNF) [e.g., for the repair of a neuronal net; GenBank Accession Nos. NM_170735.5 (SEQ ID NO:16) and NP_733931.1 (SEQ ID NO:17); NM_170734.3 (SEQ ID NO:18) and NP_733930.1 (SEQ ID NO:19); NM_170733.3 (SEQ ID NO:20) and NP_733929.1 (SEQ ID NO:21); NM_170732.4 (SEQ ID NO:22) and NP_733928.1 (SEQ ID NO:23); NM_170731.4 (SEQ ID NO:24) and NP_733927.1 (SEQ ID NO:25); NM_001709.4 (SEQ ID NO:26) and NP_001700.2 (SEQ ID NO:27); NM_001143816.1 (SEQ ID NO:28) and NP_001137288.1 (SEQ ID NO:29); NM_001143814.1 (SEQ ID NO:30) and NP_001137286.1 (SEQ ID NO:31); NM_001143813.1 (SEQ ID NO:32) NP_001137285.1 (SEQ ID NO:33); NM_001143812.1 (SEQ ID NO:34) and NP_001137284.1 (SEQ ID NO:35); NM_001143811.1

(SEQ ID NO:36) and NP_001137283.1 (SEQ ID NO:37); NM_001143810.1 (SEQ ID NO:38) and NP_001137282.1 (SEQ ID NO:39); NM_001143809.1 (SEQ ID NO:40) and NP_001137281.1 (SEQ ID NO:41); NM_001143808.1 (SEQ ID NO:42) and NP_001137280.1 (SEQ ID NO:43); NM_001143807.1 (SEQ ID NO:44) and NP_001137279.1 (SEQ ID NO:45); NM_001143806.1 (SEQ ID NO:46) and NP_001137278.1 (SEQ ID NO:47); NM_001143805.1 (SEQ ID NO:48) and NP_001137277.1 (SEQ ID NO:49)]; insulin-like growth factor 1 [IGF1, e.g., for re-myelination; GenBank Accession Nos. NM_001111285.1 (SEQ ID NO:50) and NP_001104755.1 (SEQ ID NO:51); NM_001111284.1 (SEQ ID NO:52) and NP_001104754 (SEQ ID NO:53); NM_001111283.1 (SEQ ID NO:54) and NP_001104753.1 (SEQ ID NO:55); NM_000618.3 (SEQ ID NO:56) and NP_000609.1 (SEQ ID NO:57)], basic fibroblast growth factor [bFGF, also known as FGF2 fibroblast growth factor 2 (basic); GenBank Accession Nos. NM_002006 (SEQ ID NO:58), and NP_001997 (SEQ ID NO:59)], and Ciliary neurotrophic factor [CNTF; GenBank Accession Nos. NM_000614.3 (SEQ ID NO:60) and NP_000605.1 (SEQ ID NO:61)].

According to some embodiments of the invention, the polypeptide-of-interest is a chemokine such as MCP-1 [chemokine (C-C motif) ligand 2, also known as HC11; MCAF; MCP1; MCP-1; SCYA2; GDCF-2; SMC-CF; HSMCR30; MGC9434; CCL2; GenBank Accession Nos. NM_002982.3 (SEQ ID NO:120) and NP_002973.1 (SEQ ID NO:62)], RANTES [chemokine (C-C motif) ligand 5, also known as SISd; SCYA5; RANTES; TCP228; D17S136E; MGC17164; CCL5; GenBank Accession Nos. NM_002985.2 (SEQ ID NO:63) and NP_002976.2 (SEQ ID NO:64)], IP-10 [chemokine (C-X-C motif) ligand 10; also known as C7; IFI10; INP10; IP-10; crg-2; mob-1; SCYB10; gIP-10; CXCL10; GenBank Accession NOs. NM_001565.2 (SEQ ID NO:65) and NP_001556.2 (SEQ ID NO:66)], and fractalkine [chemokine (C-X3-C motif) ligand 1; also known as NTN; NTT; CXC3; CXC3C; SCYD1; ABCD-3; C3Xkine; fractalkine; neurotactin; CX3CL1; GenBank Accession Nos. NM_002996.3 (SEQ ID NO:67) and NP_002987.1 (SEQ ID NO:68)].

According to some embodiments of the invention, the protein-of-interest is a transcription factor.

According to some embodiments of the invention, the transcription factor induces expression of interferon gamma from the T cell. Non-limiting examples of suitable transcription factors include, AP1 [C-fos; GenBank Accession Nos. NM_005252.3 (SEQ ID NO:69) and NP_005243.1 (SEQ ID NO:70)], STAT1 [signal transducer and activator of transcription 1-alpha/beta isoform alpha (GenBank Accession No. NM_007315.3 (SEQ ID NO:71), and NP_009330.1 (SEQ ID NO:72); Signal transducer and activator of transcription 1-alpha/beta isoform beta (GenBank Accession Nos. NM_139266.2 (SEQ ID NO:73) and NP_644671.1 (SEQ ID NO:74)]; Nuclear factor κB [nuclear factor of kappa light polypeptide gene enhancer in B-cells 1 (NFκB), also known as p50; KBF1; p105; EBP-1; MGC54151; NFKB-p50; NF-kappaB; NFKB-p105; NF-kappa-B; DKFZp686C01211; GenBank Accession Nos. NM_001165412.1 (SEQ ID NO:75) and NP_001158884.1 (SEQ ID NO:76); NM_003998.3 (SEQ ID NO:77) and NP_003989.2 (SEQ ID NO:78)]; nuclear factors of activated T-cells such as NFATC1 [nuclear factor of activated T-cells, cytoplasmic, calcineurin-dependent 1, also know as NFAT2; NFATc; NF-ATC; MGC138448; GenBank Accession NOs. NM_172390.1 (SEQ ID NO:79) and NP_765978.1 (SEQ ID NO:80); NM_006162.3 (SEQ ID NO:81) and NP_006153.2 (SEQ ID NO:82); NM_172387.1 (SEQ ID NO:83) and NP_765975.1 (SEQ ID NO:84); NM_172388.1 (SEQ ID NO:85) and NP_765976.1 (SEQ ID NO:86); NM_172389.1 (SEQ ID NO:87) and NP_765977.1 (SEQ ID NO:88)]; NFATC2 [nuclear factor of activated T-cells, cytoplasmic, calcineurin-dependent 2, also known as NFAT1; NFATP; GenBank Accession NOs. NM_001136021.1 (SEQ ID NO:89) and NP_001129493.1 (SEQ ID NO:90); NM_012340.3 (SEQ ID NO:91) and NP_036472.2 (SEQ ID NO:92); NM_173091.2 (SEQ ID NO:93) and NP_775114.1 (SEQ ID NO:94)]; NFATC3 [nuclear factor of activated T-cells, cytoplasmic, calcineurin-dependent 3; also known as NFAT4; NFATX; GenBank Accession Nos. NM_004555.2 (SEQ ID NO:95) and NP_004546.1 (SEQ ID NO:96); NM_173163.1 (SEQ ID NO:97) and NP_775186.1 (SEQ ID NO:98); NM_173164.1 (SEQ ID NO:99) and NP_775187.1 (SEQ ID NO:100); NM_173165.1 (SEQ ID NO:101) NP_775188.1 (SEQ ID NO:102)]; NFATC4 [nuclear factor of activated T-cells, cytoplasmic, calcineurin-dependent 4, also known as NFAT3; NF-ATc4; GenBank Accession NOs. NM_001136022.1 (SEQ ID NO:103) and NP_001129494.1 (SEQ ID NO:104); NM_004554.4 (SEQ ID NO:105) and NP_004545.2 (SEQ ID NO:106)] and NFAT5 [nuclear factor of activated T-cells 5, tonicity-responsive, also known as NFATZ; OREBP; NF-ATS; NFATL1; TONEBP; KIAA0827; GenBank Accession Nos. NM_173214.1 (SEQ ID NO:107) and NP_775321.1 (SEQ ID NO:108); NM_001113178.1 (SEQ ID NO:109) and NP_001106649.1 (SEQ ID NO:110); NM_006599.2 (SEQ ID NO:111) and NP_006590.1 (SEQ ID NO:112); NM_138713.2 (SEQ ID NO:113) and NP_619727.2 (SEQ ID NO:114); NM_138714.2 (SEQ ID NO:115) and NP_619728.2 (SEQ ID NO:116)].

According to some embodiments of the invention, the protein-of-interest is capable of treating the neurodegenerative disease.

In addition to administration of therapeutic polypeptides via the T-cells, the teachings of some embodiments of the invention can be used to deliver any polypeptide, including, for example, a toxic polypeptide [e.g., for treatment of cancer] or a diagnostic polypeptide [for in vivo diagnosis' (Kramm C M, et al. 1996. "Herpes vector-mediated delivery of marker genes to disseminated central nervous system tumors". Hum. Gene Ther. 7(3):291-300] into a brain of a subject in need-thereof.

As described, the activated T-cell is administered into the brain in a manner which prevents meningoencephalitis.

As used herein the term "meningoencephalitis" refers to a condition characterized by infection or inflammation of the brain meninges.

As described in the Background section above, prior attempts of treating acute brain injuries were based on immunization of the subject with an amyloid beta antigen and thereby induction of T-cells migration into the brain, which was occasionally associated with meningoencephalitis (Orgogozo, J. M., et al., 2003. Subacute meningoencephalitis in a subset of patients with AD after Abeta42 immunization. Neurology 61:46-54).

In contrast to the methods described in the art, the method according to some embodiments of the invention is based on intra-brain administration of T-cells in a manner which prevents meningoencephalitis.

According to some embodiments of the invention, the T-cells are administered directly into the central nervous system.

According to some embodiments of the invention, administration into the brain is effected by intracranial (IC), intracerebroventricular (ICV), intrathecal administration, and/or intraparenchymal administration (intra CSF) delivery.

The phrase "intracranial (IC) administration" as used herein refers to administration into the brain parenchyma.

As used herein the phrase "intracerebroventricular (ICV)" administration refers to administration into the lateral ventricles of the brain.

As used herein the phrase "intrathecal administration" refers to administration into the cererbrospinal fluid or into the cisterna magna (also referred to as the cerebellomedullary cistern) of the brain of a subject. It should be noted that intrathecal administration of T-cells can result in migration of the T-cells into the brain ventricles. For example, intrathecal administration can be into the spinal canal (intrathecal space surrounding the spinal cord) such as near the subject's waist.

Methods of intracranial, intracerebroventricular and/or intrathecal administration are known in the art and are described, for example, in Pathan S A, et al. 2009. "CNS drug delivery systems: novel approaches." Recent Pat. Drug Deliv. Formul. 3: 71-89; Geiger B M, et al., 2008. Survivable Stereotaxic Surgery in Rodents. J Vis Exp. 20, pii: 880. doi: 10.3791/880; Huang X, (2010). Intracranial Orthotopic Allografting of Medulloblastoma Cells in Immunocompromised Mice. J Vis Exp. 44, pii: 2153. doi: 10.3791/2153; Alam M I., et al. 2010. "Strategy for effective brain drug delivery". Review. European J. of Pharmaceutical Sciences, 40: 385-403; Bakhshi S., et al., 1995. "Implantable pumps for drug delivery to the brain". Journal of Neuro-Oncology 26:133-139; each of which is fully incorporated herein by reference.

For example, intracerebral delivery of the T cells of some embodiments of the invention into the parenchymal space of the brain can be achieved by directly injecting (using bolus or infusion) the T cells via an intrathecal catheter, or an implantable catheter essentially as described in Haugland and Sinkjaer, 1999 ["Interfacing the body's own sensing receptors into neural prosthesis devices". Technol. Health Care, 7: 393-399; Kennedy and Bakay, 1998. "Restoration of neural outpit from a paralyzed patient by a direct connection". Neuroreport, 9: 1707-1711; each of which is fully incorporated herein by reference]. For example, the catheter can be implanted by surgery into the brain where it releases the T-cells for a predetermined time period.

Intrabrain administration of the activated T-cell can be at a single injection, at a continuous infusion, or periodic administrations, and those of skills in the art are capable of designing a suitable treatment regime depending on the condition to be treated, and the treated subject.

According to some embodiments of the invention, the IC, ICV or intrathecal administration is performed by an injection or an infusion, using e.g., a needle, a syringe, a catheter, a pump, an implantable device (e.g., as is further described hereinunder) and/or any combination(s) thereof.

According to some embodiments of the invention, the IC, ICV or intrathecal administration is performed periodically.

According to some embodiments of the invention, the T cell accumulates in a hippocampus and/or cortex of the brain.

According to some embodiments of the invention, the T cell accumulates in brain regions affected with neuronal/glial damage.

According to an aspect of some embodiments of the invention, there is provided a method of administering a protein-of-interest into a brain of a subject, the method comprising administering a genetically modified T cell capable of expressing the protein-of-interest into the brain in a manner which prevents meningoencephalitis in the subject, thereby administering the protein-of-interest into the brain of the subject.

According to an aspect of some embodiments of the invention, there is provide a method of treating a pathology associated with neural damage, the method comprising administering the protein-of-interest according to the method of some embodiments of the invention into a brain of a subject in need thereof, wherein the protein-of-interest is capable of treating the pathology associated with nervous system damage, thereby treating the pathology associated with the neural damage.

The genetically modified T cell can be an activated or a non-activated T cell.

As used herein the phrase "non-activated T cell" refers to a T cell which is isolated from a subject and is not subject to stimulation in vitro.

According to some embodiments of the invention, the genetically modified T cell is activated.

Activation (e.g., stimulation) of the genetically modified T-cells can be an antigen-specific activation or a non-antigen specific polyclonal activation as described above.

As used herein the phrase "antigen-specific activated T-cell" refers to (i) a T-cell that has been activated by exposure to a cognate antigen or peptide derived therefrom or derivative thereof and (ii) a progeny of such activated T-cell.

As used herein the phrase "a cognate antigen" is an antigen that is specifically recognized by the T-cell antigen receptor of a T-cell.

Antigen-specific activation of T cells can be achieved by interacting (e.g., by incubation) of the T cells with antigen presenting cells (APCs) loaded with the specific antigenic peptide or with a functional equivalent thereof.

Non-limiting examples of specific antigens which can be used to activate the T-cells include nervous system antigens or brain-specific antigens such as amyloid beta, myelin basic protein (MBP), alpha-synuclein, hutingtin, and tau [for further examples of specific antigens see, e.g., Korn T, Magnus T, Jung S. "Autoantigen specific T cells inhibit glutamate uptake in astrocytes by decreasing expression of astrocytic glutamate transporter GLAST: a mechanism mediated by tumor necrosis factor-alpha". FASEB J. 2005; 19:1878-80, which is fully incorporated herein by reference in its entirety]; or non-nervous system antigens such as Ovalbumin (OVA) [e.g., as described in Li J, Bracht M, Shang X, Radewonuk J, Emmell E, Griswold D E, Li L. 2006. "Ex vivo activated OVA specific and non-specific CD4+CD25+ regulatory T cells exhibit comparable suppression to OVA mediated T cell responses". Cell Immunol. 241:75-84, which is fully incorporated herein by reference in its entirety].

Non-limiting examples of antigen presenting cells which can be used to activate the T cells include dendritic cells, macrophages and B-cells.

According to some embodiments of the invention, the antigen-presenting cells are loaded with the specific antigen (e.g., a nervous system specific antigen or a non-nervous system specific antigen as described above).

It should be noted that other cells, which are not naturally presenting antigens (non-APCs) can be also used, by genetically modifying them to recombinantly express MHC class II molecules (for CD4+ T cells) or MHC class I (for CD8+ T cells) [Hypertext Transfer Protocol://World Wide Web (dot) discoverymedicine (dot) com/Shuiping-Jiang/2009/07/28/adoptive-cell-therapy-using-regulatory-t-cells-as-individualized-medicine-to-promote-clinical-transplantation-tolerance/]. Once these cells express the respective MHC molecules they can be loaded with the antigenic peptide.

Alternatively or additionally, the non-APCs can be genetically modified to express molecules which cause co-stimulation of the T cells, such as CD80/CD86 which bind CD28 on the T-cell.

In addition, specific activation of T cells can be achieved by interacting the T cell with tetramers which include the MHC and the antigenic peptide [e.g., as described in J. Vis Exp. 2009; (25). pii: 1167. doi: 10.3791/1167. Visualizing antigen specific CD4+ T cells using MHC class II tetramers. James E A, LaFond R, Durinovic-Bello I, Kwok W, which is fully incorporated herein by reference in its entirety].

According to some embodiments of the invention, the antigen-specific activation further comprises incubation of the T cell with an anti CD3 antibody (which binds the CD3 unit of the TCR complex), an anti CD28 antibody (which binds the CD28 molecule on the membrane of the T cell providing $2^{nd}$ signal for T-cell activation), phytohaemagglutinin (PHA) and/or Concavalin A, and/or any combination thereof.

According to some embodiments of the invention, the activated T-cells are isolated as described below.

Circulating T-cells of a subject which recognize a specific antigen (e.g., a nervous system antigen or a non-nervous system antigen) are isolated and expanded using known procedures [e.g., as described in Burns et al., Cell Immunol. 81:435 (1983); Pette et al., Proc. Natl. Acad. Sci. USA 87:7968 (1990); Moran et al., J. Immunol. 145:540 (1990); Schluesener et al., J. Immunol. 135:3128 (1985); Suruhan-Dires Keneli et al., Euro. J. Immunol. 23:530 (1993) which are incorporated herein by reference in their entirety].

As mentioned, the T-cells according to some embodiments of the invention can be genetically modified to express a polynucleotide-of-interest (e.g., a polynucleotide encoding a polypeptide-of-interest).

The polynucleotide-of-interest can be ligated into a nucleic acid construct suitable for mammalian cell expression. Such a nucleic acid construct includes a promoter sequence for directing transcription of the polynucleotide sequence in the cell in a constitutive or inducible manner.

The nucleic acid construct of some embodiments of the invention includes additional sequences which render this vector suitable for replication and integration in prokaryotes, eukaryotes, or preferably both (e.g., shuttle vectors). In addition, a typical cloning vectors may also contain a transcription and translation initiation sequence, transcription and translation terminator and a polyadenylation signal. By way of example, such constructs will typically include a 5' LTR, a tRNA binding site, a packaging signal, an origin of second-strand DNA synthesis, and a 3' LTR or a portion thereof.

The nucleic acid construct of the some embodiments of the invention typically includes a signal sequence for secretion of the peptide from a host cell in which it is placed. Preferably the signal sequence for this purpose is a mammalian signal sequence or the signal sequence of the polypeptide variants of the some embodiments of the invention.

Eukaryotic promoters typically contain two types of recognition sequences, the TATA box and upstream promoter elements. The TATA box, located 25-30 base pairs upstream of the transcription initiation site, is thought to be involved in directing RNA polymerase to begin RNA synthesis. The other upstream promoter elements determine the rate at which transcription is initiated.

Preferably, the promoter utilized by the nucleic acid construct of the some embodiments of the invention is active in the specific cell population transformed. For example, neuron-specific promoters such as the neurofilament promoter [Byrne et al. (1989) Proc. Natl. Acad. Sci. USA 86:5473-5477] and neurofilament heavy chain gene (NFH) promoter, tyrosine hydroxlase (TH) promoter, NeuN promoter, and the doublecortin promoter).

Enhancer elements can stimulate transcription up to 1,000 fold from linked homologous or heterologous promoters. Enhancers are active when placed downstream or upstream from the transcription initiation site. Many enhancer elements derived from viruses have a broad host range and are active in a variety of tissues. For example, the SV40 early gene enhancer is suitable for many cell types. Other enhancer/promoter combinations that are suitable for some embodiments of the invention include those derived from polyoma virus, human or murine cytomegalovirus (CMV), the long term repeat from various retroviruses such as murine leukemia virus, murine or Rous sarcoma virus and HIV. See, Enhancers and Eukaryotic Expression, Cold Spring Harbor Press, Cold Spring Harbor, N.Y. 1983, which is incorporated herein by reference.

In the construction of the expression vector, the promoter is preferably positioned approximately the same distance from the heterologous transcription start site as it is from the transcription start site in its natural setting. As is known in the art, however, some variation in this distance can be accommodated without loss of promoter function.

Polyadenylation sequences can also be added to the expression vector in order to increase the efficiency of mRNA translation. Two distinct sequence elements are required for accurate and efficient polyadenylation: GU or U rich sequences located downstream from the polyadenylation site and a highly conserved sequence of six nucleotides, AAUAAA, located 11-30 nucleotides upstream. Termination and polyadenylation signals that are suitable for some embodiments of the invention include those derived from SV40.

In addition to the elements already described, the expression vector of some embodiments of the invention may typically contain other specialized elements intended to increase the level of expression of cloned nucleic acids or to facilitate the identification of cells that carry the recombinant DNA. For example, a number of animal viruses contain DNA sequences that promote the extra chromosomal replication of the viral genome in permissive cell types. Plasmids bearing these viral replicons are replicated episomally as long as the appropriate factors are provided by genes either carried on the plasmid or with the genome of the host cell.

The vector may or may not include a eukaryotic replicon. If a eukaryotic replicon is present, then the vector is amplifiable in eukaryotic cells using the appropriate selectable marker. If the vector does not comprise a eukaryotic replicon, no episomal amplification is possible. Instead, the recombinant DNA integrates into the genome of the engineered cell, where the promoter directs expression of the desired nucleic acid.

The expression vector of some embodiments of the invention can further include additional polynucleotide sequences that allow, for example, the translation of several proteins from a single mRNA such as an internal ribosome entry site (IRES) and sequences for genomic integration of the promoter-chimeric polypeptide.

Examples for mammalian expression vectors include, but are not limited to, pcDNA3, pcDNA3.1(+/−), pGL3, pZeoSV2(+/−), pSecTag2, pDisplay, pEF/myc/cyto, pCMV/ myc/cyto, pCR3.1, pSinRep5, DH26S, DHBB, pNMT1, pNMT41, pNMT81, which are available from Invitrogen, pCI which is available from Promega, pMbac, pPbac, pBK-RSV and pBK-CMV which are available from Strategene, pTRES which is available from Clontech, and their derivatives.

Expression vectors containing regulatory elements from eukaryotic viruses such as retroviruses can be also used. SV40 vectors include pSVT7 and pMT2. Vectors derived from bovine papilloma virus include pBV-1MTHA, and vectors derived from Epstein Bar virus include pHEBO, and p2O5. Other exemplary vectors include pMSG, pAV009/A$^+$, pMTO10/A$^+$, pMAMneo-5, baculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

As described above, viruses are very specialized infectious agents that have evolved, in many cases, to elude host defense mechanisms. Typically, viruses infect and propagate in specific cell types. The targeting specificity of viral vectors utilizes its natural specificity to specifically target predetermined cell types and thereby introduce a recombinant gene into the infected cell. Thus, the type of vector used by some embodiments of the invention will depend on the cell type transformed. The ability to select suitable vectors according to the cell type transformed is well within the capabilities of the ordinary skilled artisan and as such no general description of selection consideration is provided herein.

Recombinant viral vectors are useful for in vivo expression of the polynucleotide-of-interest since they offer advantages such as lateral infection and targeting specificity. Lateral infection is inherent in the life cycle of, for example, retrovirus and is the process by which a single infected cell produces many progeny virions that bud off and infect neighboring cells. The result is that a large area becomes rapidly infected, most of which was not initially infected by the original viral particles. This is in contrast to vertical-type of infection in which the infectious agent spreads only through daughter progeny. Viral vectors can also be produced that are unable to spread laterally. This characteristic can be useful if the desired purpose is to introduce a specified gene into only a localized number of targeted cells.

Various methods can be used to introduce the expression vector of some embodiments of the invention into stem cells. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et at. [Biotechniques 4 (6): 504-512, 1986] and include, for example, stable or transient transfection, lipofection, electroporation and infection with recombinant viral vectors. In addition, see U.S. Pat. Nos. 5,464,764 and 5,487,992 for positive-negative selection methods.

Introduction of nucleic acids by viral infection offers several advantages over other methods such as lipofection and electroporation, since higher transfection efficiency can be obtained due to the infectious nature of viruses.

Currently preferred in vivo nucleic acid transfer techniques include transfection with viral or non-viral constructs, such as adenovirus, lentivirus, Herpes simplex I virus, or adeno-associated virus (AAV) and lipid-based systems. Useful lipids for lipid-mediated transfer of the gene are, for example, DOTMA, DOPE, and DC-Chol [Tonkinson et al., Cancer Investigation, 14(1): 54-65 (1996)]. The most preferred constructs for use in gene therapy are viruses, most preferably adenoviruses, AAV, lentiviruses, or retroviruses. A viral construct such as a retroviral construct includes at least one transcriptional promoter/enhancer or locus-defining element(s), or other elements that control gene expression by other means such as alternate splicing, nuclear RNA export, or post-translational modification of messenger. Such vector constructs also include a packaging signal, long terminal repeats (LTRs) or portions thereof, and positive and negative strand primer binding sites appropriate to the virus used, unless it is already present in the viral construct. In addition, such a construct typically includes a signal sequence for secretion of the peptide from a host cell in which it is placed. Preferably the signal sequence for this purpose is a mammalian signal sequence or the signal sequence of the polypeptide variants of some embodiments of the invention. Optionally, the construct may also include a signal that directs polyadenylation, as well as one or more restriction sites and a translation termination sequence. By way of example, such constructs will typically include a 5' LTR, a tRNA binding site, a packaging signal, an origin of second-strand DNA synthesis, and a 3' LTR or a portion thereof. Other vectors can be used that are non-viral, such as cationic lipids, polylysine, and dendrimers.

A suitable viral expression vector may also be a chimeric adenovirus/retrovirus vector which combines retroviral and adenoviral components. Such vectors may be more efficient than traditional expression vectors for transducing tumor cells [Pan et al., Cancer Letters 184: 179-188 (2002)].

A specific example of a suitable viral vector for introducing and expressing the polynucleotide sequence of some embodiments of the invention in an individual is the adenovirus-derived vector Ad-TK. This vector expresses a herpes virus thymidine kinase (TK) gene for either positive or negative selection and includes an expression cassette for desired recombinant sequences. This vector can be used to infect cells that have an adenovirus receptor which includes most cancers of epithelial origin (Sandmair et al., 2000. Hum Gene Ther. 11:2197-2205).

Features that limit expression to particular cell types can also be included. Such features include, for example, promoter and regulatory elements that are specific for the desired cell type. Secretion signals generally contain a short sequence (7-20 residues) of hydrophobic amino acids. Secretion signals are widely available and are well known in the art, refer, for example to von Heijne [J. Mol. Biol. 184:99-105 (1985)] and Lej et al., [J. Bacteriol. 169: 4379 (1987)].

According to an aspect of some embodiments of the invention there is provided a method of treating a pathology associated with neural damage, the method comprising administering by intracerebroventricular (ICV) or intrathecal administration a polyclonal activated T cell into the brain, thereby treating the pathology associated with neural damage.

According to some embodiments of the invention, the polyclonal activated T cell is activated by antigen-specific activation.

According to some embodiments of the invention, the polyclonal activated T cell is activated by a brain antigen-specific activation.

According to some embodiments of the invention, the polyclonal activated T cell is activated by non-antigen-specific activation.

The T cells of some embodiments of the invention (e.g., the activated T cells (either by antigen-specific activation or by non-antigen specific activation), the genetically modified T cells, the genetically modified non-activated T-cell, or combination of both) can be administered to an organism per se, or in a pharmaceutical composition where it is mixed with suitable carriers or excipients.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the T cells of some embodiments of the invention (e.g., the activated T cells, the genetically modified T cells, the genetically modified non-activated T-cell, or combination of both) accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include intracranial, intraventricular and intrathecal.

Conventional approaches for drug delivery to the central nervous system (CNS) include neurosurgical strategies such as intracerebral injection or intracerebroventricular infusion.

Pharmaceutical compositions of some embodiments of the invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with some embodiments of the invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

Pharmaceutical compositions suitable for use in context of some embodiments of the invention include compositions wherein the active ingredients are contained in an amount effective to achieve the intended purpose. More specifically, a therapeutically effective amount means an amount of active ingredients (the T cells of some embodiments of the invention, e.g., the activated T cells, the genetically modified T cells, the genetically modified non-activated T-cell, or combination of both) effective to prevent, alleviate or ameliorate symptoms of a pathology (e.g., the pathology associated with neural damage such as a neurodegenerative disease, brain injury or stroke) or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide brain levels of the active ingredient are sufficient to induce or suppress the biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions of some embodiments of the invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert.

Compositions comprising a preparation of the invention formulated in a compatible pharmaceutical carrier may also be prepared, placed in an appropriate container, and labeled for treatment of an indicated condition, as is further detailed above.

According to an aspect of some embodiments of the invention, there is provided a device for intra brain administration, comprising a catheter and a non-antigen specific polyclonal activated T cell.

According to some embodiments of the invention the device comprising a catheter and a genetically modified T cell.

According to an aspect of some embodiments of the invention, there is provided a device for intracerebroventricular (ICV) or intrathecal administration, comprising a catheter and a polyclonal activated T cell.

According to some embodiments of the invention the device is for treating a pathology associated with neural damage.

According to some embodiments of the invention the device is for treating a neurodegenerative disease in a subject.

According to some embodiments of the invention, the device is an implantable device, wherein at least part of the device enters the brain.

FIG. 14A schematically illustrates a device according to some embodiments of the invention. Device 100 comprises catheter 120 for delivery of T cells 180 of some embodiments of the invention into brain 130 of a subject. According to some embodiments of the invention, catheter 120 is inserted into the lateral ventricle of brain 130, into parenchyma tissue of brain 130 or into the Cisterna magna of brain 130.

According to some embodiments of the invention, catheter 120 is implanted in brain 130. Implantation into the brain can be by placing the catheter under the scalp, with the catheter terminating in a hollow portion of the brain.

FIG. 14B schematically illustrates a device according to some embodiments of the invention. Device 400 comprises catheter 120 for delivery of T cells 180 of some embodiments of the invention intrathechally to cerebrospinal fluid (CSF) 190 of a subject. According to some embodiments of the invention, catheter 120 is inserted into CSF 190 via the spinal canal of the subject's waist.

According to some embodiments of the invention the device further comprises a reservoir which comprises T cells 180 of some embodiments of the invention.

FIG. 15 schematically illustrates a device according to some embodiments of the invention. Device 200 comprises catheter 120 for delivery of T cells 180 of some embodiments of the invention into brain 130 of a subject and reservoir 140 which comprises the T cells 180. Reservoir 140 is in fluid communication with catheter 120. Reservoir 140 can be implanted in brain 130 or can be attached to the outer side of the scalp of the subject. Reservoir 140 is replenishable.

According to some embodiments of the invention the device further comprises a pump for releasing the T cells of some embodiments of the invention from the reservoir.

FIG. 16 schematically illustrates a device according to some embodiments of the invention. Device 300 comprises catheter 120 for delivery of T cells 180 of some embodiments of the invention into brain 130 of a subject, reservoir 140 which comprises the T cells 180 and pump 160. Pump 160 is in contact with reservoir 140. Pump 160 dispenses T-cells 180 from reservoir 140. Pump 160 can be implanted into brain 130 or can be attached to the outer side of the scalp.

Pump 160 can be an electrical pump, battery operated pump, an osmotic pump, a vapour pressure-activated pump, aperistaltic pump, or any combination thereof.

According to some embodiments of the invention, pump 160 and reservoir 140 are implanted in brain 130 of the subject.

Non-limiting examples of suitable devices for intrabrain delivery of the T cells of the invention include the Ommaya® reservoir pump (Vygon Neuro, Norristown, USA; the Infusaid system MiniMed PIMS® system (MiniMed, Sylamar, CA, USA); or the DUROS™ (Durect, CA, USA).

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

General Materials and Experimental Methods

Mice—
C57BL6 and SJL mice were purchased from Harlan Israel. APP/PS1-Tg mice were kindly supplied by Dr. Mathias Jucker (Radde R, et al. 2006. Abeta42-driven cerebral amyloidosis in transgenic mice reveals early and robust pathology. EMBO Rep. 7: 940-6). Transgenic SJL mice expressing IFN-γ under the myelin basic protein promoter were kindly donated by Dr. Owens (Renno, T., Taupin, V., 1998. Interferon-γ in progression to chronic demyelination and neurological deficit following acute EAE. Mol. Cell. Neurosci. 12, 376-389). Homozygous IFN-γ-Tg mice were crossed with APP/PS1-Tg mice to generate APP/PS1/IFN-γ B6SJLF1 Tg mice, respectively. All surgical and experimental procedures were reviewed and approved by the Institutional Animal Care and Use Committee (IACUC) of Ben-Gurion University of the Negev (Approval number IL-610904). Both humanized Tg-mice model begin to develop plaques at 3 months of age.

Generation of Aβ-Specific Th1/Th2/Th17 Cells—
B6SJLF1 mice (3 months old) were immunized by injection into the flank with $A\beta_{1-42}$ (100 μg, GenScript Corp., Piscataway, N.J., USA) emulsified in complete Freund's adjuvant (CFA) H37Ra (Difco, Detroit, Mich., USA). Mice were sacrificed 10 days later and their popliteal, inguinal, renal and iliac lymph nodes were harvested. Cells ($5 \times 10^6$) were cultured in 24 wells (0.5 ml/well) culture dish in Biotarget medium supplemented with 1% Pen/Strep/Nystatin, 40 mM L-glutamine (Biological industries, Israel) and 10 μg/ml of $A\beta_{1-42}$ (DAEFRHDSGYEVHHQKLVFFAED-VGSNKGAIIGLMVGGVVIA (SEQ ID NO:117). To differentiate T cells into the different phenotypes, the following recombinant cytokines and antibodies were added at the time of cell seeding and 48 hours later:

(1) Th1 phenotype, recombinant Interleukin (IL)-12 (20 ng/ml, Biolegend, San Diego, USA) and anti-IL-4 (20 μg/ml, Biolegend);

(2) Th2 phenotype, recombinant IL-4 (4 ng/ml, Biolegend) and anti-IL12 (20 μg/ml, Biolegend);

(3) Th17 phenotype, recombinant IL-6 (20 ng/ml, Peprotec), TGF-β (5 ng/ml, Peprotec), IL-23 (20 ng/ml, eBioscience), anti-IFN-γ (10 μg/ml, Biolegend) and anti-IL-4 (10 μg/ml, Biolegend).

Two days following seeding, and there after, cells were supplemented with 0.5 ml of DMEM medium containing 10% fetal calf serum, 10 mM HEPES, 1 mM sodium pyruvate, 10 mM nonessential amino acids, 1% Pen/Strep, 50 μM β-mercaptoethanol and 20 u/ml of recombinant IL-2. Additional stimulations, were carried out by seeding T cells ($2 \times 10^5$ cells/ml) along with splenocytes ($5 \times 10^6$ cells/ml) from irradiated (6000 rad) B6SJLF1 mice spleens as previously described (Fitch F W, Gajewski T F, Hu-Li J. Curr. Protoc. Immunol. 2006; Chapter 3: Unit 3.13. Production of TH1 and TH2 cell lines and clones. Pappu B P, Dong C. 2007, Curr. Protoc. Immunol. Chapter 6: Unit 6.25. Measurement of interleukin-17). Stimulations were carried out at least twice before stable expression of phenotype specific-secreted cytokines was detected using ELISA assays.

Isolation of OVA-Specific T Cells—
Spleens from ovalbumin transgenic (OT-II Tg) mice were harvested and CD4+ cells were negatively selected (Stemcells) and isolated.

Non-Specific Activation of OVA-T Cells—

Enriched CD4+ cells (which were isolated from the OT-II Tg mice) were cultured for 48 hours in Biotarget culture medium (Catalogue number 05-080-1, Biological Industries, Beit-Haemek, Israel) supplemented with 1% Pen/Strep/Nystatin, 40 mM L-glutamine and Dynabeads™ (Invitrogen, Carlsbad, Calif., USA) mouse T-activator CD3/CD28 (Invitrogen, Carlsbad, Calif., USA) were added to the culture medium at a bead-to-cell ratio of 1:1 followed by the addition of 30 U/ml recombinant interleukin-2 (rIL-2) (Invitrogen, Carlsbad, Calif., USA). Supernatants from cultured cells were separated from the beads and analyzed using ELISA for IL2, IL10 and IFN-γ prior to injection into the brain.

Non-Antigen Specific Polyclonal Activation of T-Cells— was performed essentially as described in Li J et al. 2007 ["Transfer of in vitro expanded T lymphocytes after activation with dendritomas prolonged survival of mice challenged with EL4 tumor cells". Int. J. Oncol. 31:193-197, which is fully incorporated herein in its entirety). Briefly, purified T cells ($1-1.5 \times 10^6$) were placed in a 24 well tissue culture plate in the presence of the Biotarget culture medium (Catalogue number 05-080-1, Biological Industries, Beit-Haemek, Israel) supplemented with 1% Pen/Strep/Nystatin, 40 mM L-glutamine. Dynabeads™ (Invitrogen, Carlsbad, Calif., USA) mouse T-activator CD3/CD28 were added to the culture medium at a bead-to-cell ratio of 1:1 followed by the addition of 30 U/ml recombinant interleukin-2 (rIL-2). The T cells were then incubated in a humidified $CO_2$ incubator at 37° C., and were examined daily, noting cell size and shape. Cell shrinking and reduced proliferation rate is typically observed in exhausted cell cultures. When the cell density exceeded $2.5 \times 10^6$ cells/ml or when the medium turned yellow the cultures were split to a density of $0.5-1 \times 10^6$ cells/ml in Biotarget culture medium containing 30 U/ml rIL-2. Typically activation of the T-cells occurred within 2 days in the described culture conditions following which the activated T cells were injected into the brain.

Cytokine ELISA—

T cells ($2 \times 10^5$ cells/ml) and irradiated splenocytes ($5 \times 10^6$ cells/ml) were cultured in a U-shaped 96-well-plate culture dishes in Biotarget medium supplemented with 1% Pen/Strep/Nystatin, 40 mM L-glutamine. IL-2 and IL-4 were measured in the supernatant after 24 hours, IFN-γ and IL-10 after 48 hours, and IL-17A after 72 hours, in each case with a sandwich ELISA according to the manufacturer's instructions (Biolegend, San Diego, Calif., USA).

$^3$-[H]-Thymidine Incorporation Assay—

T cells ($2 \times 10^5$ cells/ml) and irradiated splenocytes ($5 \times 10^6$ cells/ml) were cultured in a U-shaped 96-well-plate culture dishes in Biotarget medium supplemented with 1% Pen/Strep/Nystatin, 40 mM L-glutamine. 1 µCi of $^3$-[H]-Thymidine was added after 72 hours and was left for 12 hours to allow the cells incorporate the labeled thymidine into their DNA. Cells were harvested and radioactivity levels were measured using a β-counter (Manu.).

T Cells Intracranial Injections—

For injection of non-activated cells, fresh cells from spleens of B6 mice were harvested and CD4 T cells were separated using a CD4 negative selection kit (R&D Systems). Cell were washed with PBS, counted using hemicytometer and re-suspended to the desired concentration in PBS. For the injection of activated Aβ-specific Th1 cells T cells, T cells were harvested and CD4 T cells were separated 48 hours after stimulation. In all experiments, 250,000 cells were injected stereotacticaly into the lateral ventricle (x—±1, y—−0.5, z—2.5) of C57BL6 WT or to one-year old APP/PS1 and APP/PS1/IFN-γ Tg mice.

Immunohistochemistry—

T cells-injected mice were sacrificed at different time points and their brains were removed. Brains were put in a 4% paraformaldehyde (PFA) solution for 24 hours followed with 48 hours in 30% sucrose solution. Finally, brains were placed in molds containing an OCT compound (Tissue-Tek, Torrance, Calif., USA) and frozen at −80° C. Serial free-floating sagital sections were cut using a cryostat (35 µm thick) to include a full representation of the hippocampus. Sections were washed 2 times with PBS/Tween (0.05%) and incubated 1 hour at room temperature (RT) with primary antibody diluting buffer (Biomeda Corp.) to block non-specific staining. Sections were incubated with primary antibodies overnight at 4° C. The following primary antibodies were used: αCD4 (at a dilution of 1:50, Biolegend), αIBA-1 (at a dilution of 1:750, Wako), αAβ (at a dilution of 1:500, generated at our animal facility). Sections were washed and incubated for 1 hour at RT with the appropriate secondary fluorescent antibodies (at a dilution of 1:500, AlexaFluor 488, 546 or 647, Molecular Probes). TO-PRO3 (at a dilution of 1:3000, Invitrogen, Carlsbad, Calif., USA) was used to view nuclei of cells. Finally, sections were loaded onto slides, cleared, mounted with VectaMount (Vector Labs) and viewed under an Olympus Fluoview FV1000 laser scanning confocal microscope.

Amyloid Plaque Load Quantification—

One-year old APP/PS1/IFN-γ Tg-mice were injected with 250,000 Aβ-specific (n=5) or OVA-specific (n=2) Th1 cells into the lateral ventricle and sacrificed 28 days later. Mice brains were removed and sections were stained for Aβ. At least 4 sections per brain were stained and amyloid load was quantified using Volocity image analysis software.

Example 1

Naïve T Cells do not Penetrate the Parenchymal Tissue of the Brain

The present inventors have tested the use of ICV and IC injection of T-cells for therapeutic applications.

As shown in FIGS. 1A-D, injection of naïve CD4 T-cells into the CNS results in rapid clearance of the cells with no migration of the cells into the tissue. Cells are present in the injection area and at the dentate gyrus 3 hours after administration (FIGS. 1A-C). These cells do not penetrate the parenchymal tissue of the brain and apparently do not cross the perivascular space.

Example 2

Stimulated T Cells Enter Parenchymal Tissue of the Brain More Efficiently than Naïve T Cells The present inventor has uncovered that activated T cells can penetrate the brain as follows.

Non-specific stimulation of T cells (OVA-specific CD4 T-cells or A-β-specific CD4 T-cells) enables their migration in the brain—OVA-specific CD4 T-cells were stimulated by polyclonal stimulation with αCD3 and αCD28 antibodies. Upon polyclonal stimulation, the OVA-specific CD4 T cells enter the brain parenchyma and reside for several days (FIGS. 2A-C) around the injection site. Similarly, Aβ-specific T cells stimulated ex-vivo by αCD3 and αCD28 antibodies (polyclonal stimulation) penetrate the parenchyma as observed at 5 days post injection (FIGS. 4A-B).

The cells were detected throughout the brain, with higher numbers in the hippocampus and cortex. At 14 days post injection (dpi), residual numbers of CD4 T-cells were detected mainly at the ventricle and meningeal regions (FIGS. 4C-D). 27 dpi the brain parenchyma, ventricle and meningial region were devoid of CD4 T cells (FIG. 4E). This time-dependent distribution of CD4 T-cells in the brain correlated with the CD4 marker detected by RT-PCR analysis (FIG. 4F). It is shown that at 5 dpi high levels of CD4 could be detected relative to PBS-injected mouse. The levels of CD4 sharply decreases at 14 and 27 dpi (FIGS. 4C-E shown by immuno-histochemistry, and FIG. 4F shown by RT-PCR) which indicates that the cells migrated out of the brain or underwent apoptosis. Additionally, analysis of the brains by RT-PCR also revealed high expression of MHC class II (detected by CD74) at 5 dpi (FIG. 4G). Similar to CD4, the expression of MHC class II decreased by 14 and 27 dpi (FIG. 4G). This pattern of MHC class II expression could be attributed to the effect of IFN-γ secreted by the injected T cells (FIG. 4H).

These results indicate that in contrast to naïve T cells, stimulated T-cells enter the parenchymal tissue of the brain more efficiently. Stimulation can be carried out by various strategies such as using endogenous CNS antigen such as Aβ or by polyclonal induction of naïve T-cells with αCD3 and αCD28 antibodies. The use of specific antigen requires several rounds of T-cells stimulation by antigen presenting cells (APCs). Polyclonal stimulation is a shorter approach which can be carried out by several methods that are currently approved for clinical trials.

Altogether, these results indicate that the polyclonal activation is sufficient for antigen-specific CD4 T cells to cross the perivascular space and enter the brain parenchyma. In addition, the higher levels of MHC class II induced in the injected brain may serve to stimulate the T cells specifically, by surrounding antigen presenting cells, based on antigen recognition by the T-cell receptor (TCR).

Specific Stimulation of T Cells with an OVA Peptide, a Non-CNS Antigen Enables the Migration of T Cells in the Brain—

CD4 T-cells were isolated from C57BL/60T-II Tg mice by negative selection and were stimulated using 0.005, 0.05 or 2 µg/ml of an OVA peptide (SEQ ID NO:118). As shown in FIG. 3F, the CD4 T cells secreted interferon gamma in response to OVA antigen in a dose specific manner. When injected ICV to the brains of wild type C57BL/6 mice the activated T cells migrated from the site of injection into the hippocampus, cortex and meninges of the injected brains, in a manner which depended on the OVA activation performed in vitro prior to ICV administration. Thus, T cells which were stimulated with low concentrations of OVA, which were not sufficient for induction of interferon-γ secretion, failed to migrate and were absent from the brain parenchyma (FIG. 3A). In contrast, T cells which were stimulated in vitro by OVA concentrations sufficient to induce IFN-γ secretion were capable of migrating to the brain parenchyma (FIGS. 3B, 3C, 3D and 3E).

Altogether, these results demonstrate that stimulated T cells (which are stimulated either specifically or un-specifically) enter the brain parenchyma of wild type (WT) mice in a manner which depends on a sufficient level of IFN-γ secreted by the T cells.

Example 3

Generation of Specific T-Cells by Ex Vivo Stimulation

Specific T-cells can be generated using T-cells removed from a given individual followed by several rounds of ex-vivo stimulation using an endogenous antigen. The ex-vivo stimulation can result in generation of well characterized T-cell sub-populations, such as Th1, Th2 or Th17. Using a cocktail of antibodies and recombinant cytokines, it is possible to generate antigen-specific Th1, Th2 and Th17 T-cell lines for further usage in injection experiments (Fitch F W, Gajewski T F, Hu-Li J; Curr Protoc Immunol. 2007 November; Chapter 6: Unit 6.25. Measurement of interleukin-17. Pappu B P, Dong C. Curr. Protoc. Immunol. 2006; Chapter 3: Unit 3.13. Production of TH1 and TH2 cell lines and clones). A T-cell line secreting a mixed profile of Th1 or Th2 for example can also be generated. In addition, T-cells can be genetically manipulated by introducing foreign DNA by lentiviral transfection and express specific cytokine of neuronal growth factor.

The different stimulation strategies are illustrated in FIGS. 5A-E, 6A-E and 7A-F. Using cells originating from $A\beta_{1-42}$ vaccinated mice it is possible to direct them to either Th1 profile (FIGS. 5A-E) with high secretion of IFNγ and IL-2; or to Th2 profile with low IFNγ secretion but high IL-2, IL-4 and IL-10 (FIG. 6A-E); or Th17 cells secreting high levels of IL-17 (FIG. 7A-F).

Example 4

Stimulated T Cells can Migrate within the Brain and are Cleared after 28 Days from Injection Following ex-vivo stimulation of Aβ-specific T-cells (FIGS. 6A-E) towards Th1 profile, T-cells were injected into AD Tg mice (APP/PS1/IFN-γ mouse model of AD). IHC analysis revealed that the stimulated CD4 T-cells enter the parenchymal tissue of the brain (FIG. 8A-B). As soon as 5 dpi, cells are visualized primarily in the cortex and hippocampus of the brain tissue reflecting their ability to migrate within the CNS away from the injection site. A time scale analysis of the injected mice demonstrated that numerous CD4 T-cells can be detected 7 dpi (FIGS. 9A, 9B and 9C) and their number and distribution peaks at around 14 dpi (FIGS. 9D and 9E). However, 28 dpi (FIGS. 9F and 9G) there is an apparent decrease in the number of T-cells in the brain. The pattern of migration and the time-dependent distribution may reflect a clearance process of the cells from the CNS. This kinetics demonstrates the effectiveness of this system so that the T cells reside in the CNS for only a limited amount of time. Thus, any prolong adverse immune response is prevented.

Example 5

Migration of T Cells in the Brain does not Require Endogenous Pre-Expression of Interferon Gamma in the Brain Similar cellular kinetics was demonstrated in a mouse model of AD which had no IFNγ expression in the brain (the APP/PS1 mouse model; FIGS. 12A, 12B and 12C). In previous studies the present inventors demonstrated that migration of peripheral endogenous T-lymphocytes into the brain of APP Tg-mice was dependent on Aβ immunization and on the expression of IFNγ in the brain under the MBP promoter (Monsonego A., et al., 2006, Proc. Natl. Acad. Sci. U.S.A. 103:5048-53. Abeta-induced meningoencephalitis is IFN-gamma-dependent and is associated with T cell-dependent clearance of Abeta in a mouse model of Alzheimer's disease). The results presented herein show that the migration of T-cells within the brain following their ICV injection does not require pre-expression of IFNγ by brain-endogenous cells.

Example 6

Injected T Cells Associate with Amyloid Plaques and Microglia

A more detailed IHC was carried out to further characterize the association of the ICV injected CD4 T-cells with the endogenous CNS components. The Tg-mouse models of AD begin to accumulate amyloid plaques at 3 months of age. Thus, by the time of injection (one-year-old animals) there is a wide distribution of plaques in the hippocampus and cortex regions. Injection of stimulated CD4 Th1 cells into these mouse models resulted in specific localization of the cells around the amyloid plaques during the entire length of the experiment (FIGS. 10A-C). This close association is depicted 7 dpi where the CD4 T-cells can be seen around the core of the Aβ plaques (FIGS. 10D-F). A more discrete analysis indicated that the co-localization of the CD4 T-cells with Ab plaques is not accidental and it is mediated by the presence of microglia. Microglial cells, identified by IBA-1 staining were present around the amyloid plaques and CD4 T-cells (FIGS. 11A-C). This association may reflect the MHC II presentation of Aβ to the injected CD4 T cells and activation of their effector function.

Example 7

ICV and IC Injection of T-Cells for Therapeutic Applications

Another indication for the therapeutic effect of the injected CD4 T-cells is demonstrated in FIG. 13. Comparison of plaques area in a Tg-mouse model (APP/PS1/IFNγ) 28 dpi shows a 31% reduction in the Aβ plaque area relative to plaques in the same mouse model following injection of CD4 T-cells with unrelated specificity.

Altogether, these data suggest that antigen-specific T cells are required for the effective plaque removal, recognizing their antigen on APCs at sites of Aβ plaques.

In summary, a new approach for the treatment of chronic neurological conditions and AD is suggested by these results. The direct administration of activated specific T-cells into the CNS may overcome some of the major limitations that were observed following active immunization. Moreover, it allows efficient targeting of damaged areas in the brain by CD4 T-cells which then release their therapeutics specifically at places of need, while avoiding peripheral and meninginal side effects.

Analysis and Discussion

In chronic situations when the blood brain barrier (BBB) is only slightly compromised, it is important to control the infiltration of immune components eliciting neuro-protective responses. The results presented herein demonstrate that administration of T-cells derived from the patient's immune system into the CNS can be beneficial to patients suffering from slowly progressing neurological disorders. The T cells can be genetically manipulated to carry drugs such as neurotrophic factors (NTFs), cytokines and chemokines and targeted to the damage site in the brain based on antigen specificity.

The effect of T-cell administration into the brain was examined in two AD mouse models carrying the human mutated APP and PS1 genes, both accumulate Aβ plaques in the brain followed by cognitive impairments. In one of the models small amounts of IFN-γ are produced in the brain but do not cause spontaneous infiltration of bone-marrow derived cells or abnormal glial activation. Antigen specific T-cell lines were generated ex-vivo by either antigen-specific or polyclonal stimulation. Following induction, T-cells are injected intracranialy (IC) or intracerebroventricular (ICV) and visualized by specific cellular staining. Following ex-vivo activation and IC injection it is possible to visualize the cells in different parts of the brain even 28 days post injection. This demonstrates the ability of the T-cells not only to reside in the CNS but also to migrate to various sites. Notably, kinetic analysis indicated that IC-injected cells eventually leave the CNS. In addition, IC-injected animals had completely normal behavior and normal activity 28 days post injection (until experiments termination). Ex-vivo activated T-cells, IC injected to old APP Tg mice, migrated to sites of Aβ plaques, and enhanced the recruitment of microglial cells. Furthermore, the presence of specifically activated CD4 T-cells inside the CNS of an AD mouse model, resulted in reduction in the amyloid plaque load in the brain. When none-activated T-cells were IC-injected, the majority of the cells left the brain shortly after injection. This short presence of none specific T-cells in the CNS is another important feature, and indicates the safety of this approach. Taken together, IC injection of antigen or polyclonal stimulated T-cells clearly demonstrates a novel therapeutic strategy for chronically progressing neurological diseases.

Example 8

In Vitro Differentiation of Primary Splenocytes into $T_H1$ and $T_H2$ Phenotypes $T_H$ (helper) cells are essential regulators of immune responses. These cells can be divided into several subtypes, among them the well characterized $T_H1$ and $T_H2$ and the $T_H17$ cells which have been associated with autoimmunity. Splenocytes were isolated in order to differentiate the naïve $T_H$ population into $T_H1$ or $T_H2$ subtypes following polyclonal stimulation by anti CD3 antibody, as follows.

Differentiation of Naïve TH Population from Splenocytes into $T_H1$ and $T_H2$ Cells—

In order to obtain $T_H1$ and $T_H2$ T cells, isolated primary splenocytes were seeded ($2.5 \times 10^6$/ml) in 24-well tissue culture plates (at a cell density of about $0.5 \times 10^6$/cm$^2$) coated with 0.5 μg/ml anti-CD3 antibody for one week. The cells were cultured in the presence of the DMEM culture medium containing 10% fetal calf serum, 10 mM HEPES, 1 mM sodium pyruvate, 10 mM nonessential amino acids, 1% Pen/Strep and 50 μM β-mercaptoethanol. Differentiation of the cells into $T_H1$ or $T_H2$ was induced by addition of 20 ng/ml IL-12 and 20 μg/ml anti-IL-4 antibody (for induction of differentiation into $T_H1$ cells) or 4 ng/ml IL-4 and 20 μg/ml anti-IL-12 antibody (for induction into differentiation into $T_H2$ cells) to the culture medium for two days. After one week the cells were collected and seeded in tissue culture wells coated with 0.1 μg/ml anti-CD3 antibody. Supernatants were collected after 24, 48 and 72 hours for analysis of IL-2, IL-4, IFN-γ, IL-10 and IL-17A secretion by ELISA. The results are presented in FIGS. 17A-E. Note that undifferentiated and differentiated cells express IL-2. $T_H1$ cells express high levels of IFN-γ and very low levels of IL-10 and IL-17A, while $T_H2$ cells express high levels of the $T_H1$ cytokine, IFN-γ, and the $T_H2$ cytokines IL-10 and IL-4 and very low levels of IL-17A.

Example 9

Genetic Modification of T Cells by Lentiviral Infection in Order to Induce Expression of Neurotrophic Factors Experimental Methods Cloning of Brain-Derived Neurotrophic Factor (BDNF) for Production in Recombinant Lentiviral Vector—

Total mRNA from the brain of C57BL6 wild-type mouse was reverse transcribed by reverse transcriptase (from Biolab, Isreal). cDNA was used as a template to amplify BDNF with BDNF-specific primers [Forward: TCCACCGCGGC-CGCGCCACCATGACCATCCTTTTCCTTAC (SEQ ID NO:129) and Reverse: CTATACGGATCCAATCCAC-TATCTTCCCCTTTTAATG (SEQ ID NO:130)] including Kozak sequence and BamHI and NotI restriction sequences. The amplified BDNF sequence was cut by BamHI and NotI and cloned into the pHAGE-CMV-eGFP-W transfer vector of the lenti virus production system (kindly provided by Dr. Ran Taube) under the CMV promoter together with Green Fluorescence Protein (GFP) separated by IRES sequence for simultaneous production of BDNF and GFP. The cloned BDNF was sequenced and blasted to confirm the BDNF sequence.

Production of Recombinant Lentiviral Vectors by Calcium Phosphate Transfection—

Recombinant lentiviral vector for BDNF expression was produced in 293T cells. 293T cells are human embryonic kidney epithelial cells transformed with adenovirus E1A/E1B oncoproteins and transfected with SV40 large T antigen and a G418 selection plasmid. 293T cells are known to be highly transfectable. 293T cells were grown in DME+10% fetal calf serum (heat-inactivated)+Pen/Strept medium. $4.5 \times 10^6$ 293T cells were seeded 20-24 hours before transfection in 10 ml media in 10 cm plates. For calcium phosphate transfection the following mix was prepared: DNA/Calcium mix (5 µg HIV gag-pol expression plasmid), 5 µg pRC/CMV-Rev 1b (accessory protein rev), 3 µg pHDM-Tat 1b (accessory protein tat), 20 µg pHAGE-CMV-eGFP-W (transfer vector), 6 µg pHDM.G (env, VSVG pseudotype), 50 µl cold 2M $CaCl_2$, $dH_2O$ (to 500 µl). Then 500 µl of sterile HEPES buffered saline (2×HBS) that contains 281 mM NaCl, 100 mM HEPES and 1.5 mM $Na_2HPO_4$ (pH 7.12) was added slowly. The tube was flicked several times to mix well and let to sit at room temperature for about 20 minutes. Then the mix was slowly added to the cells. 12-16 hours after transfection, the media was replaced with growth media with 25 mM HEPES buffer. 40-48 hours after transfection, the supernatant was harvested, centrifuged 5 min at 1000 rpm at 4° C. and passed through 0.45 µm membrane. The supernatant can directly be used for infection or frozen and stored at −80° C. for an extended period of time.

Titrating of Virus by Infection of 293T Cells—

293T cells were plated ($0.7 \times 10^5$ cells/ml/well) in 24-well plate. The virus titer generated is normally in the range of $10^6$/ml. The supernatant containing the virus was added at proper serial dilutions to obtain an appropriate level of infection (the percentage of infection is preferably between 1-10%). 14 hours later the supernatant was discarded and replaced with a fresh media. The cells were then incubated for another 34 hours, harvested and analyzed by FACS for percentage of GFP producing cells. The virus titer is calculated as follows:

[Cell number at the time of infection×percentage of cells that are GFP(+)]/the volume of virus supernatant used in the infection(in ml).

For instance, if one gets 20% GFP(+) cells after infecting $10^6$ cells with 0.1 ml virus, the virus titer would be $2 \times 10^6$/ml.

Coating Plates with Poly-L-Lysine and Lenti Vector—

24-well plates were coated for 2 hours at room temperature with 0.5 ml of 50 µg/ml of Poly L-Lysine in PBS. The final concentration of lysine should be 0.25 µg/cm$^2$. The plate was blocked for 30 minutes with 2% BSA in PBS. Afterwards the plates were centrifuged twice for 1 hour at 16° C. at 4000 rpm with 1 ml of retrovirus containing supernatant (non-concentrated) and CD4 T cells were placed at final concentration of $0.5 \times 10^6$ cell/ml for 48 hours infection.

Viral-Induced BDNF Expression—

The expression of BDNF in 293T cells infected by the virus was evaluated by immunoblot analysis. Non-infected and viral infected cells were lysed in ice-cold lysis buffer (50 mM HEPES (pH 7.3, 150 mM NaCl, 1 mM EDTA, 1 mM EGTA, 10% glycerol, 10 µM $MgCl2$, 2% Triton X-100) containing protease inhibitor cocktail (Sigma-Aldrich, MO, USA). Cell lysates (50 and 100 µg proteins) were separated by SDS-PAGE and the resolved proteins were transferred to nitrocellulose membrane. Membranes were then blocked in 5% BSA in TBS-T (10 mM Tris, 135 mM NaCl, pH 7.4, 0.05% Tween 20), incubated overnight at 4° C. with anti-BDNF (from Santa cruz Biotechnology, INC, CA, USA) followed by peroxidase-conjugated secondary antibody (GE Healthcare, UK). Detection of immunoreactive bands was carried out using enhanced chemiluminescence. FIG. 21 shows the results of the immunoblotting.

Stimulation of T cells was performed as described in Example 8 above.

Experimental Results

T Cells are Genetically Modified to Express BDNF/GFP—

In order to test the ability to generate T cells which are genetically modified to express a neurotrophic factor, such as BDNF, resting T cells (i.e., non-activated T cells) were stimulated with coated anti-CD3 or beads coated with anti-CD3 and anti-CD28 and were then infected with lentivirus producing GFP/BDNF (FIGS. 18A-D-19A-B). 48 hours after infection the cells were analyzed by FACS and confocal microscopy for GFP expression. FIGS. 18B and 18D show infection efficiency of 75% and 87% for anti-CD3 and anti-CD3/CD28 beads, respectively. FIGS. 19A-B show GFP+ T cells stimulated with anti-CD3/CD28 beads and infected with BDNF-encoding lentivirus. T cells are thus genetically manipulated at a high efficiency to express a key neurotrophic factor such as BDNF.

Altogether, these results conclusively show the genetic modification of T cells to express a protein of interest such as a neurotrophic factor.

Example 10

Influence of Brain-Specific Th1 T Cells on Neurogenesis in the Brain

DCX is a protein expressed when immature neurons begin to migrate into the granular layer. It allows the detection of proliferating and differentiating neuronal progenitor cells (NPCs), by their morphology, to neuroblasts in the subgranular zone and non-proliferating immature cells extending neurites into the granular layer. Neuroblast cells can be divided into two stages of differentiating cells: neuroblasts 1 (dcx1, proliferating cells) and neuroblasts 2 (granular, differentiating cells).

Experimental Methods

Preparation of Th1 T-Cell Line—

C57BL/6J wild type (WT) mice were immunized with A-beta 1-42 peptide (SEQ ID NO:117) emulsified in Complete Frends Adjuvant (CFA) to evoke an immune response Th1 T-cells were isolated from the lymph nodes of the immunized WT mice and cells were then stimulated in vitro with A-beta and differentiated towards Th1 line using a cocktail of cytokines and antibodies (a cocktail of 20 ng/ml IL-12 and 20 µg/ml anti-IL-4 antibody) which was added to the culture medium for two days.

Injection of Th1 T-Cells to Mice—

Two month old C57BL6 mice were used in the experiment. Each group, the treated mice and the untreated mice, included 3-4 mice. The U.T. (untreated) group, which included age-matched control mice, reflects neurogenesis in the intact brain, and the group of treated mice reflects neurogenesis following injection of Th1 cells. The Th1 cell line was injected to the mice 48 hours post in-vitro stimulation, when cells were most active. Injection was performed using a stereotaxic (ST) surgery technique, Th1 T-cells were injected into the lateral ventricle (i.e., ICV injection).

Antibodies Used for Immunostaining— anti-doublecortin (specifically labels neuronal precursors) obtained from Santa Cruz Biotechnology, Inc.

Experimental Results

The Influence of Brain-Specific Th1 T Cells on Neurogenesis in the Mouse Brain—

Neurogenesis was examined 14 days post injection by immunostaining of doublecortin (DCX) and subsequently confocal microscopy analysis using the Volocity software (PerkinElmer) to enable 3D image (z-stack) analysis.

For quantification the present inventors have analyzed three different areas: the total cells in the dentate gyrus (DG) area, the cells in neuroblasts 1, and the cells in neuroblasts 2, per mouse, representing DG neurogenesis.

Administration of Th1 T Cells into the Brain Results in Increased Neurogenesis—

The results presented in FIG. 20 show increased DG neurogenesis in mice injected ICV with stimulated T cells (total cells in the DG), and in particular, increased number of differentiating neuroblasts in the neuroblasts 2 (granular) area of the DG following injection of Th1 cells.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

REFERENCES

Additional References are Cited in Text

1. Selkoe, D. J. 2001. Alzheimer's disease: genes, proteins, and therapy. Physiol Rev 81:741-766.
2. McGeer, P. L., and E. G. McGeer. 2006. NSAIDs and Alzheimer disease: Epidemiological, animal model and clinical studies. Neurobiol Aging.
3. McGeer, P. L., J. Rogers, and E. G. McGeer. 2006. Inflammation, anti-inflammatory agents and Alzheimer disease: the last 12 years. J Alzheimers Dis 9:271-276.
4. Shechter, R., A. London, C. Varol, C. Raposo, M. Cusimano, G. Yovel, A. Rolls, M. Mack, S. Pluchino, G. Martino, S. Jung, and M. Schwartz. 2009. Infiltrating blood-derived macrophages are vital cells playing an anti-inflammatory role in recovery from spinal cord injury in mice. PLoS Med 6:e1000113.
5. Monsonego, A., J. Imitola, S. Petrovic, V. Zota, A. Nemirovsky, R. Baron, Y. Fisher, T. Owens, and H. L. Weiner. 2006. Abeta-induced meningoencephalitis is IFN-{gamma}-dependent and is associated with T cell-dependent clearance of Abeta in a mouse model of Alzheimer's disease. Proc Natl Acad Sci USA 103:5048-5053.
6. Fisher, Y., A. Nemirovsky, R. Baron, and A. Monsonego. T cells specifically targeted to amyloid plaques enhance plaque clearance in a mouse model of Alzheimer's disease. PLoS One 5:e10830.
7. Orgogozo, J. M., S. Gilman, J. F. Dartigues, B. Laurent, M. Puel, L. C. Kirby, P. Jouanny, B. Dubois, L. Eisner, S. Flitman, B. F. Michel, M. Boada, A. Frank, and C. Hock. 2003. Subacute meningoencephalitis in a subset of patients with AD after Abeta42 immunization. Neurology 61:46-54.
8. Gandy, S., and L. Walker. 2004. Toward modeling hemorrhagic and encephalitic complications of Alzheimer amyloid-beta vaccination in nonhuman primates. Curr Opin Immunol 16:607-615.
9. Pfeifer, M., S. Boncristiano, L. Bondolfi, A. Stalder, T. Deller, M. Staufenbiel, P. M. Mathews, and M. Jucker. 2002. Cerebral hemorrhage after passive anti-Abeta immunotherapy. Science 298:1379.
10. Monsonego, A., V. Zota, A. Karni, J. I. Krieger, A. Bar-Or, G. Bitan, A. E. Budson, R. Sperling, D. J. Selkoe, and H. L. Weiner. 2003. Increased T cell reactivity to amyloid beta protein in older humans and patients with Alzheimer disease. J Clin Invest 112:415-422.
11. Moalem, G., A. Monsonego, Y. Shani, I. R. Cohen, and M. Schwartz. 1999. Differential T cell response in central and peripheral nerve injury: connection with immune privilege. Faseb J 13:1207-1217.
12. Alam M I., et al. 2010. "Strategy for effective brain drug delivery". Review. European J. of Pharmaceutical Sciences, 40: 385-403.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US10117895B2). An electronic copy of the "Sequence Listing" will also be available from the USPTO upon request and payment of the fee set forth in 37 CFR 1.19(b)(3).

What is claimed is:

1. A method of treating Alzheimer's disease in a subject in need thereof, the method comprising:
    (a) selecting non-cytotoxic CD4+ Abeta specific Th1 T cells from a pool of T cells,
    (b) ex-vivo stimulating said non-cytotoxic CD4+ Abeta specific Th1 T cells with an anti-CD3 and an anti-CD28 antibodies to thereby obtain activated non-cytotoxic Abeta specific CD4+ T cells that expresses interferon gamma, wherein said CD4+ T cells are autologous or allogeneic to the subject, and
    (c) intracerebroventricularly administering an effective amount of said activated non-cytotoxic Abeta specific CD4+ T cells into the brain of said subject, wherein said administration results in (i) reduction in amyloid-beta plaques in the brain of the subject, and (ii) increase in neurogenesis in the granular area of the dentate gyrus (DG) in the brain of the subject, while preventing meningoencephalitis in the subject, thereby treating the Alzheimer's disease in the subject in need thereof.

2. The method of claim 1, wherein said reduction in said amyloid beta plaques is of at least 30% as compared to administration of a control CD4+ T cells.

3. The method of claim 1, wherein said activated non-cytotoxic CD4+ T cells accumulate in a hippocampus and cortex of the brain.

4. The method of claim 1, wherein said intracerebroventricular administration is performed periodically.

5. The method of claim 1, wherein said CD4+ T cells are autologous T cell of the subject.

6. The method of claim 1, wherein said CD4+ T cells are allogeneic T cell.

7. The method of claim 1, wherein the subject is a human subject.

8. The method of claim 1, wherein said pool of T cells is comprised in a blood sample, a spleen sample or a lymph node sample.

* * * * *